United States Patent
Gotou et al.

(10) Patent No.: US 6,610,729 B1
(45) Date of Patent: Aug. 26, 2003

(54) HYDROXAMIC ACID DERIVATIVES AND MEDICINAL UTILIZATION THEREOF

(75) Inventors: Tomokazu Gotou, Hirakata (JP); Shinji Takeda, Fukuoka (JP); Kazuhiro Maeda, Hirakata (JP); Tomohiro Yoshida, Hirakata (JP); Naoki Sugiyama, Iruma (JP); Tadahiro Takemoto, Hirakata (JP)

(73) Assignee: Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 09/701,043

(22) PCT Filed: May 19, 1999

(86) PCT No.: PCT/JP99/02631
§ 371 (c)(1),
(2), (4) Date: Nov. 22, 2000

(87) PCT Pub. No.: WO99/61412
PCT Pub. Date: Dec. 2, 1999

(30) Foreign Application Priority Data

May 22, 1998 (JP) ............................................. 10-141304

(51) Int. Cl.$^7$ .................... C07C 259/06; C07D 209/46; C07D 209/48; A01K 31/16; A61P 19/02

(52) U.S. Cl. ..................... 514/419; 514/575; 546/315; 548/200; 548/236; 548/492; 548/540; 549/72; 549/478; 560/41; 562/444; 562/622

(58) Field of Search .......................... 546/315; 548/200, 548/236, 492, 540; 549/72, 478; 560/41; 562/444, 622; 514/419, 575

(56) References Cited

U.S. PATENT DOCUMENTS 5,985,911 A * 11/1999 Davidsen et al. ........... 562/623

FOREIGN PATENT DOCUMENTS

| JP | 8-505605 | 6/1996 |
|---|---|---|
| WO | 94/10990 | 5/1994 |
| WO | 98/30541 | 7/1998 |

OTHER PUBLICATIONS

Graninger et al. Curr. Opin. Rhematol. 13(3) 209–13, 2001 (PubMed Abstract provided).*
Shaw et al. Expert Opin. Investig. Drugs 9(7) 1469–1478, 2000 (PubMed Abstract provided).*
McGeehan, G.M. et al., "Regulation of tumour necrosis factor–α processing by a metalloproteinase inhibitor", Nature, vol. 370, pp. 558–561 (1994).

* cited by examiner

Primary Examiner—Richard L. Raymond
Assistant Examiner—Venkataraman Balasubramanian
(74) Attorney, Agent, or Firm—Wenderoth, Lind & Ponack, L.L.P.

(57) ABSTRACT

The present invention relates to a hydroxamic acid derivative of the formula (I)

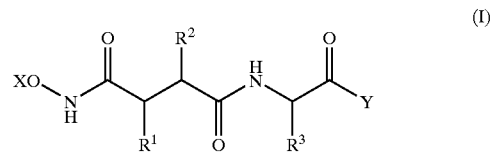

wherein each symbol is as defined in the specification, a pharmacologically acceptable salt thereof, a pharmaceutical composition containing the derivative or a salt thereof, and to pharmaceutical use thereof. The hydroxamic acid derivative and a pharmacologically acceptable salt thereof of the present invention have an inhibitory activity of TNF α production, and are useful for, for example, the prophylaxis and treatment of the diseases such as autoimmune diseases and inflammatory diseases (e.g., sepsis, MOF, rheumatoid arthritis, Crohn's disease, cachexia, myasthenia gravis, systemic lupus erythematosus, asthma, I type diabetes, psoriasis and the like), and the like.

13 Claims, No Drawings

HYDROXAMIC ACID DERIVATIVES AND MEDICINAL UTILIZATION THEREOF

CROSS-REFERENCE

This application is a 371 of PCT/JP99/02631 filed May 19, 1999.

TECHNICAL FIELD

The present invention relates to a novel hydroxamic acid derivative and a pharmacologically acceptable salt thereof. More particularly, the present invention relates to a hydroxamic acid derivative or a pharmacologically acceptable salt thereof, which are useful as an inhibitor of TNF α (tumor necrosis factor α) production. The present invention also relates to a novel intermediate compound useful for the synthesis of the above-mentioned hydroxamic acid derivative.

BACKGROUND ART

TNF α is a cytokine known to be widely involved in the activation of biological defense and immune system during inflammation. On the other hand, it is known that a sustained and excessive production of TNF α causes various diseases associated with organ disorders represented by MOF (multiple organ failure), as well as aggravation thereof.

MOF is understood to be a functional failure that simultaneously or continuously emerges in-plural important organs, such as lung, heart, kidney, liver, central nervous system, blood coagulation system and the like, during progress of a major invasion (after major operation, after serious external injuries, burn, acute pancreatitis, severe infection and the like). MOF shows poor prognosis, which is in proportion to the number of dysfunctional organs, and an extremely high mortality.

Nevertheless, it is a representative intractable disease for which no cure has been established.

In recent years, a report has documented that an inhibitor of MMP (matrix metalloproteinase), which is an enzyme in charge of processing from membrane-bound TNF α to free TNF α, specifically suppresses the secretion of free TNF α, which is caused by the stimulation of endotoxin (LPS:lipopolysaccharide), and shows a life-saving effect [e.g., McGeehan, G. M. et al. Nature 370: p. 558–561 (1994)].

Given such finding, a wide range of investigations of prophylactic and therapeutic agents for various intractable diseases, inclusive of MOF where free TNF α increases, have been underway by inhibiting TNF α production by the use of a hydroxamic acid derivative that has heretofore been studied as an MMP inhibitor (e.g., WO94/10990). However, a satisfactory prophylactic and therapeutic agent has not been afforded.

DISCLOSURE OF THE INVENTION

The present invention has been made in the above-mentioned background and aims at providing a novel hydroxamic acid derivative or a pharmacologically acceptable salt thereof, which is useful as an inhibitor of TNF α production.

It is another object of the present invention to provide a novel intermediate compound useful for the synthesis of said compound.

A further object of the present invention is to provide a novel inhibitor of TNF α production, which is useful as a pharmaceutical agent.

Accordingly, the present invention provides the following (1) to (11).

(1) A hydroxamic acid derivative of the formula (I):

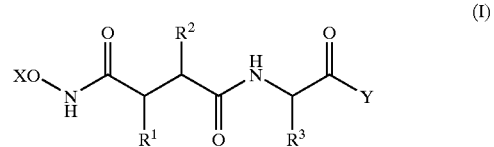

wherein

X is hydrogen or hydroxy-protecting group;

$R^1$ is hydrogen, alkyl, arylalkyl, heteroarylthioalkyl, arylthioalkyl, alkylthioalkyl, arylalkylthioalkyl, phthalimidoalkyl, alkenyl, or —$(CH_2)_l$—A wherein l is an integer of 1 to 4 and A is a 5- or 6-membered N-heterocycle
(a) which is bonded by N atom,
(b) which optionally has at least one atom selected from N, O and S as an additional heteroatom at a position not adjacent to the bonded N atom,
(c) in which one or both C atom(s) adjacent to said bonded N atom is(are) substituted by oxo, and
(d) which is benzo-fused, or one or more other C atom(s) is(are) substituted by lower alkyl or oxo, and/or a different N atom is optionally substituted by lower alkyl or phenyl;

$R^2$ is hydrogen, alkyl, arylalkyl, heteroarylalkyl, cycloalkyl, cycloalkylalkyl or aryl;

$R^3$ is hydrogen, alkyl or a group of the formula

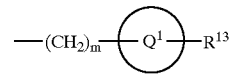

wherein $Q^1$ is an aromatic hydrocarbon ring or an aromatic heterocycle, m is an integer of 0 to 3, and R is hydrogen, halogen, hydroxy, nitro, cyano, trifluoromethyl, lower alkyl, alkoxy, alkylthio, formyl, acyloxy, phenyl, arylalkyl, carboxy, —COORa wherein Ra is lower alkyl, arylalkyl or aryl, carbamoyl, guanidino, hydroxysulfonyloxy, sulfo, arylalkyloxyalkyl or a group selected from

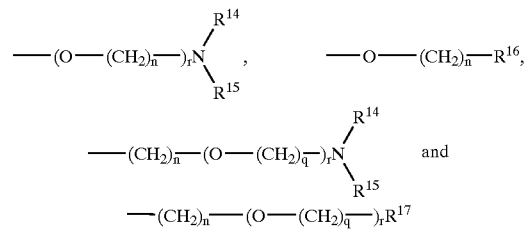

wherein n and q are the same or different and each is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, $R^{16}$ is aryl, heteroaryl, hydroxysulfonyloxy or sulfo and $R^{17}$ is hydroxy, hydroxysulfonyloxy, sulfo or carboxy; and Y is a group of the formula

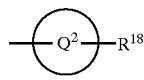

wherein $Q^2$ is an aromatic hydrocarbon ring or an aromatic heterocycle, and $R^1$ is hydrogen, halogen, hydroxy, nitro, cyano, trifluoromethyl, lower alkyl, alkoxy, alkylthio, formyl, acyloxy, phenyl, arylalkyl, carboxy, —COORa wherein Ra is lower alkyl, arylalkyl or aryl, carbamoyl, guanidino, hydroxysulfonyloxy, sulfo, arylalkyloxyalkyl or a group selected from

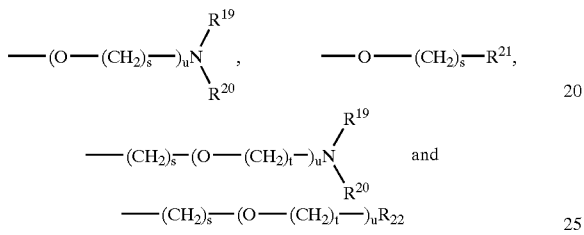

wherein s and t are the same or different and each is an integer of 1 to 5, u is an integer of 0 to 2, $R^{19}$ and $R^{20}$ are the same or different and each is hydrogen, alkyl, arylalkyl, heteroarylalkyl or aryl, or $R^{19}$ and $R^{20}$ may form, together with the adjacent nitrogen atom, an optionally substituted heterocycle, $R^{21}$ is aryl, heteroaryl, hydroxysulfonyloxy, sulfo or carboxy, and $R^{22}$ is hydroxy, hydroxysulfonyloxy, sulfo or carboxy;

provided that (i) $R^3$ is a group of the formula (A)

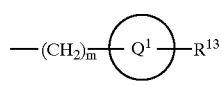

wherein $Q^1$ is a benzene ring, m is an integer of 0 to 3, and $R^{13}$ is guanidino, hydroxysulfonyloxy, sulfo or a group selected from

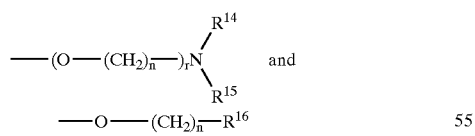

wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, or (ii) when $R^3$ is a group other than the aforementioned formula (A), Y should be a group of the formula (B)

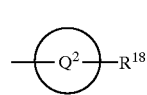

wherein $Q^2$ is a benzene ring, and $R^{18}$ is a group selected from

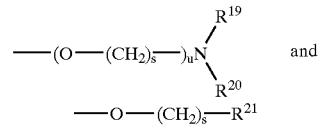

wherein s is an integer of 1 to 5, u is an integer of 1 or 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{21}$ is aryl, heteroaryl, hydroxysulfonyloxy, sulfo or carboxy, or $Q^2$ is a furan ring, and $R^{18}$ is arylalkyloxyalkyl or a group selected from

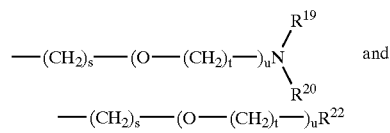

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy, wherein the aforementioned arylalkyl, heteroarylthioalkyl, arylthioalkyl, arylalkylthioalkyl, phthalimidoalkyl, aryl, heteroaryl and heteroarylalkyl may have a substituent, or a pharmacologically acceptable salt thereof.

(2) The hydroxamic acid derivative of the aforementioned (1) wherein (i) $R^3$ is a group of the formula (A)

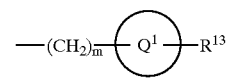

wherein $Q^1$ is a benzene ring, m is an integer of 0 to 3, and $R^{13}$ is guanidino, hydroxysulfonyloxy, sulfo or a group selected from

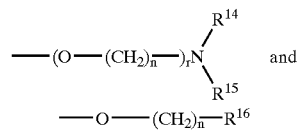

wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, and Y is furyl, thienyl, pyrrolyl, pyridyl, thiazolyl, phenyl, alkoxyphenyl, or phenyl substituted by —$NR^{19}R^{20}$ wherein $R^{19}$ and $R^{20}$ are the same or different and each is alkyl, or (ii) $R^3$ is alkyl or a group of the formula

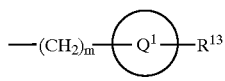

wherein $Q^1$ is a benzene ring, m is an integer of 0 to 3, and $R^{13}$ is hydrogen, and Y is a group of the formula (B)

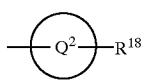

(B)

wherein $Q^2$ is a benzene ring, and $R^{18}$ is a group selected from

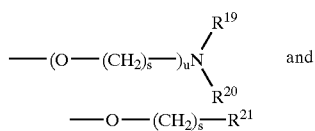

and wherein s is an integer of 1 to 5, u is an integer of 1 or 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{21}$ is aryl, heteroaryl, hydroxysulfonyloxy, sulfo or carboxy, or $Q^2$ is a furan ring, and $R^{18}$ is arylalkyloxyalkyl or a group selected from

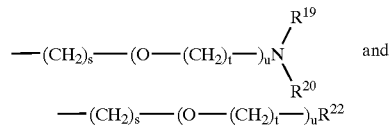

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy, or a pharmacologically acceptable salt thereof.

(3) The hydroxamic acid derivative of the aforementioned (2), wherein $R^{13}$ in the formula (A) is guanidino, hydroxysulfonyloxy or a group of the formula

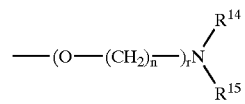

wherein each symbol is as defined in the aforementioned (2) or a pharmacologically acceptable salt thereof.

(4) The hydroxamic acid derivative of the aforementioned (2) or a pharmacologically acceptable salt thereof, which is a member selected from the group consisting of 5-methyl-3(R)-[1(S)-[4-[2-[1-(4-methyl)piperazinyl] ethoxy]benzoyl]-2-phenyl]ethylcarbamoyl-2(R or S)-phthalimidomethylhexanohydroxamic acid dihydrochloride, 3(R)-[1(S)-[4-(2-dimethylaminoethoxy)benzoyl]-2-phenyl]ethylcarbamoyl-5-methyl-2(R or S)-phthalimidomethylhexanohydroxamic acid hydrochloride, 3(R)-[1(S)-(2-furyl)carbonyl-2-(4-guanidinophenyl)] ethylcarbamoyl-5-methyl-2(R or S)-phthalimidomethylhexanohydroxamic acid hydrochloride, 3(R)-[1(S)-[2-[5-(2-dimethylaminoethoxy)methyl]furyl] carbonyl-2-phenyl]ethylcarbamoyl-5-methyl-2(R or S)-phthalimidomethylhexanohydroxamic acid hydrochloride, 3(R)-[2-[4-(2-dimethylaminoethoxy)phenyl]-1(S)-(2-furyl)carbonyl]ethylcarbamoyl-5-methyl-2(R or S)-(2, 5-dioxo-3,4,4-trimethyl-1-imidazolidinyl) methylhexanohydroxamic acid hydrochloride, sodium salt of 3(R)-[1(S)-(2-furyl)carbonyl-2-[4-(hydroxysulfonyloxy)phenyl]]ethylcarbamoyl-5-methyl-2(R or S)-phthalimidomethylhexanohydroxamic acid, sodium salt of 3(R)-[1(S)-(2-furyl)carbonyl-2-(4-sulfophenyl)ethylcarbamoyl]-5-methyl-2(R or S)-(2-naphthylmethyl)hexanohydroxamic acid, sodium salt of 3(R)-[1(S)-(2-furyl)carbonyl-2-(4-sulfophenyl)ethylcarbamoyl]-5-methyl-2(R or S)-(1-naphthylmethyl)hexanohydroxamic acid, sodium salt of 2(R or S)-benzyl-3(R)-[1(S)-(2-furyl) carbonyl-2-(4-sulfophenyl)ethylcarbamoyl]-5-methylhexanohydroxamic acid, sodium salt of 3(R)-[1(S)-(2-furyl)carbonyl-2-(4-sulfophenyl)-ethylcarbamoyl]-5-methyl-2(R or S)-phthalimidomethylhexanohydroxamic acid, sodium salt of 3(R)-[1(S)-(2-furyl)carbonyl-2-(4-sulfophenyl)ethylcarbamoyl]-5-methyl-2(R or S)-(1-oxoisoindolin-2-ylmethyl)hexanohydroxamic acid, 3(R)-[2-(4-aminophenyl)-1(S)-(2-furyl)carbonyl] ethylcarbamoyl-5-methyl-2(R or S)-phthalimidomethylhexanohydroxamic acid hydrochloride, 5-methyl-3(R)-[2-phenyl-1(S)-[4-(2-piperidinoethoxy) benzoyl]]ethylcarbamoyl-2(R or S)-phthalimidomethylhexanohydroxamic acid hydrochloride, 3(R)-[1(S)-[2-(5-dimethylaminomethyl)furyl]carbonyl-2-phenyl]ethylcarbamoyl-5-methyl-2(R or S)-phthalimidomethylhexanohydroxamic acid hydrochloride, 3(R)-[2-[4-(2-dimethylaminoethoxy)phenyl]-1(S)-(2-furyl)carbonyl]ethylcarbamoyl-5-methyl-2(R or S)-phthalimidomethylhexanohydroxamic acid hydrochloride, 3(R)-[1(S)-[2-(5-hydroxymethyl)furyl]carbonyl-2-phenyl]ethylcarbamoyl-5-methyl-2(R or S)-phthalimidomethylhexanohydroxamic acid, 2(R or S),5-dimethyl-3(R)-[1(S)-[4-(2-dimethylaminoethoxy)benzoyl]-2-phenyl]ethylcarbamoylhexanohydroxamic acid hydrochloride, 3(R)-[1(S)-[4-(2-dimethylaminoethoxy)benzoyl]-2-phenyl]ethylcarbamoyl-5-methyl-2(R or S)-(3-phenylpropyl)hexanohydroxamic acid hydrochloride, 3(R)-[1(S)-[4-(2-dimethylaminoethoxy)benzoyl]-2-phenyl]ethylcarbamoyl-5-methyl-2(R or S)-(2,5-dioxo-3,4,4-trimethyl-1-imidazolidinyl)methylhexanohydroxamic acid hydrochloride, 3(R)-[2,2-dimethyl-1(S)-[4-(2-dimethylaminoethoxy)benzoyl]]propylcarbamoyl-5-methyl-2(R or S)-phthalimidomethylhexanohydroxamic acid hydrochloride, 3(R)-[1(S)-[4-(2-dimethylaminoethoxy)benzoyl]-2-phenyl]ethylcarbamoyl-5-methyl-2(R or S)-(2-propenyl)hexanohydroxamic acid hydrochloride, 3(R)-[2-[4-(2-dimethylaminoethoxy)phenyl]-1(S)-(2-furyl)carbonyl]ethylcarbamoyl-5-methyl-2(R or S)-(3-phenylpropyl)hexanohydroxamic acid hydrochloride, sodium salt of 3(R)-[1(S)-(2-furyl)carbonyl-2-[4-(hydroxysulfonyloxy)phenyl]]ethylcarbamoyl-5-methyl-2(R or S)-(2,5-dioxo-3,4,4-trimethyl-1-imidazolidinyl)methylhexanohydroxamic acid, 3(R)-[2,2-dimethyl-1(S)-[4-(2-dimethylaminoethoxy)benzoyl]]propylcarbamoyl-5-methyl-2(R or S)-(3-phenylpropyl)hexanohydroxamic acid hydrochloride, sodium salt of 3(R)-[1(S)-(2-furyl)carbonyl-2-[4-(hydroxysulfonyloxy)phenyl]]ethylcarbamoyl-5-methyl-2(R or S)-(3-phenylpropyl)hexanohydroxamic acid, 3(R)-[1(S)-[4-(2-dimethylaminoethoxy)benzoyl]-2-phenyl]ethylcarbamoyl-5-methyl-2(R or S)-(2-naphthylmethyl)hexanohydroxamic acid hydrochloride, 3(R)-[1(S)-[4-(2-dimethylaminoethoxy)benzoyl]-2-phenyl]ethylcarbamoyl-5-methyl-2(R or S)-(1-oxoisoindolin-2-ylmethyl)hexanohydroxamic acid hydrochloride, 3(R)-[2-[4-(2-dimethylaminoethoxy)phenyl]-1(S)-(2-furyl)carbonyl]ethylcarbamoyl-5-methyl-2(R or S)-(2-naphthylmethyl)-hexanohydroxamic acid hydrochloride, 3(R)-[2-[4-(2-dimethylaminoethoxy)phenyl]-1(S)-(2-furyl)carbonyl]ethylcarbamoyl-5-methyl-2(R or S)-(1-oxoisoindolin-2-ylmethyl)hexanohydroxamic acid hydrochloride, 3(R)-[2,2-dimethyl-1(S)-[4-(2-dimethylaminoethoxy)benzoyl]]propylcarbamoyl-5-methyl-2(R or S)-(2,5-dioxo-3,4,4-trimethyl-1-imidazolidinyl)methylhexanohydroxamic acid hydrochloride, sodium salt of 3(R)-[1(S)-(2-furyl)carbonyl-2-[4-(hydroxysulfonyloxy)phenyl]]ethylcarbamoyl-5-methyl-2(R or S)-(2-naphthylmethyl)hexanohydroxamic acid, sodium salt of 3(R)-[1(S)-(2-furyl)carbonyl-2-[4-(hydroxysulfonyloxy)phenyl]]ethylcarbamoyl-5-methyl-2(R or S)-(1-oxoisoindolin-2-ylmethyl)hexanohydroxamic acid, sodium salt of 3(R)-[1(S)-(2-furyl)carbonyl-2-(4-sulfophenyl)ethylcarbamoyl]-5-methyl-2(R or S)-(3-phenylpropyl)hexanohydroxamic acid, sodium salt of 3(R)-[1(S)-(2-furyl)carbonyl-2-(4-sulfophenyl)ethylcarbamoyl]-5-methyl-2(R or S)-(2,5-dioxo-3,4,4-trimethyl-1-imidazolidinyl)methylhexanohydroxamic acid, and 3(R)-[1(S)-[2-(5-hydroxymethyl)furyl]carbonyl-2-phenyl]-ethylcarbamoyl-5-methyl-2(R or S)-(2,5-dioxo-3,4,4-trimethyl-1-imidazolidinyl)methylhexanohydroxamic acid.

(5) The hydroxamic acid derivative of the aforementioned (1) or (2), wherein $R^1$ is phthalimidomethyl, or a pharmacologically acceptable salt thereof.

(6) The hydroxamic acid derivative of the aforementioned (1) or (2), wherein $R^2$ is isobutyl, or a pharmacologically acceptable salt thereof.

(7) The hydroxamic acid derivative of the aforementioned (1) or (2), wherein $R^3$ is benzyl optionally substituted by a substituent selected from guanidino, hydroxysulfonyloxy, sulfo,

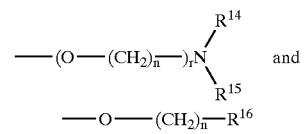

and wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, or a pharmacologically acceptable salt thereof.

(8) A compound of the formula (II):

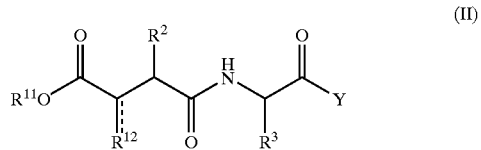

(II)

wherein $R^{11}$ is hydrogen, alkyl, arylalkyl, heteroarylalkyl or aryl,

----- is a single bond or a double bond, when

----- is a single bond, $R^{12}$ is hydrogen, alkyl, arylalkyl, heteroarylthioalkyl, arylthioalkyl, alkylthioalkyl, arylalkylthioalkyl, phthalimidoalkyl, alkenyl, —(CH$_2$)$_l$—A wherein l is an integer of 1 to 4, A is a 5- or 6-membered N-heterocycle
  (a) which is bonded by N atom,
  (b) which optionally has at least one atom selected from N, O and S as an additional heteroatom at a position not adjacent to the bonded N atom, (c) in which one or both C atom(s) adjacent to said bonded N atom is(are) substituted by oxo, and
(d) which is benzo-fused, or one or more other C atom(s) is(are) substituted by lower alkyl or oxo, and/or a different N atom is optionally substituted by lower alkyl or phenyl, or —COOR$^{23}$ wherein R$^{23}$ is hydrogen, alkyl, arylalkyl, heteroarylalkyl or aryl, or when

----- is a double bond, R$^{12}$ is CH$_2$;

R$^2$ is hydrogen, alkyl, arylalkyl, heteroarylalkyl, cycloalkyl, cycloalkylalkyl or aryl;

R$^3$ is hydrogen, alkyl or a group of the formula

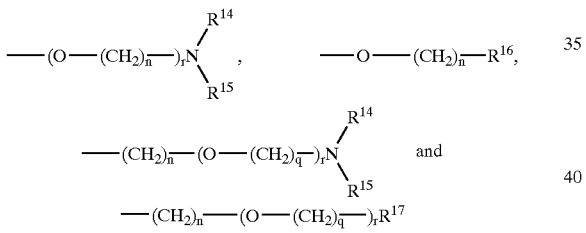

wherein Q$^1$ is an aromatic hydrocarbon ring or an aromatic heterocycle, m is an integer of 0 to 3, and R$^{13}$ is hydrogen, halogen, hydroxy, nitro, cyano, trifluoromethyl, lower alkyl, alkoxy, alkylthio, formyl, acyloxy, phenyl, arylalkyl, carboxy, —COORa wherein Ra is lower alkyl, arylalkyl or aryl, carbamoyl, guanidino, hydroxysulfonyloxy, sulfo, arylalkyloxyalkyl or a group selected from

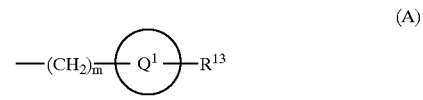

wherein n and q are the same or different and each is an integer of 1 to 5, r is an integer of 0 to 2, R$^{14}$ and R$^{15}$ are the same or different and each is hydrogen, alkyl, arylalkyl, heteroarylalkyl or aryl, or R$^{14}$ and R$^{15}$ may form, together with the adjacent nitrogen atom, an optionally substituted heterocycle, R$^{16}$ is aryl, heteroaryl, hydroxysulfonyloxy or sulfo, and R$^{17}$ is hydroxy, hydroxysulfonyloxy, sulfo or carboxy;

Y is a group of the formula

wherein Q$^2$ is an aromatic hydrocarbon ring or an aromatic heterocycle, and R$^{18}$ is hydrogen, halogen, hydroxy, nitro, cyano, trifluoromethyl, lower alkyl, alkoxy, alkylthio, formyl, acyloxy, phenyl, arylalkyl, carboxy, —COORa wherein Ra is lower alkyl, arylalkyl or aryl, carbamoyl, guanidino, hydroxysulfonyloxy, sulfo, arylalkyloxyalkyl or a group selected from

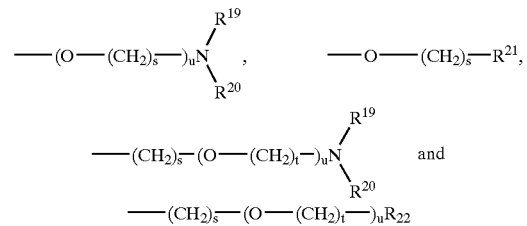

wherein s and t are the same or different and each is an integer of 1 to 5, u is an integer of 0 to 2, R$^{19}$ and R$^{20}$ are the same or different and each is hydrogen, alkyl, arylalkyl, heteroarylalkyl or aryl, or R$^{19}$ and R$^{20}$ may form, together with the adjacent nitrogen atom, an optionally substituted heterocycle, R$^{21}$ is aryl, heteroaryl, hydroxysulfonyloxy, sulfo or carboxy, and R$^{22}$ is hydroxy, hydroxysulfonyloxy, sulfo or carboxy;

provided that (i) R$^3$ is a group of the formula (A)

(A)

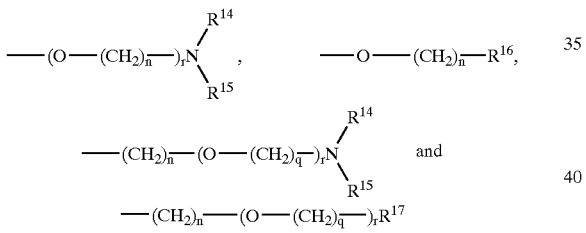

wherein Q$^1$ is a benzene ring, m is an integer of 0 to 3, and R$^{13}$ is guanidino, hydroxysulfonyloxy, sulfo or a group selected from

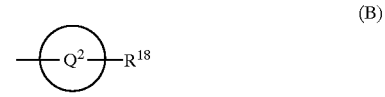

wherein n is an integer of 1 to 5, r is an integer of 0 to 2, R$^{14}$ and R$^{15}$ are the same or different and each is hydrogen, alkyl, arylalkyl, heteroarylalkyl or aryl, or R$^{14}$ and R$^{15}$ may form, together with the adjacent nitrogen atom, an optionally substituted heterocycle, and R$^{16}$ is hydroxysulfonyloxy or sulfo, or (ii) when R$^3$ is a group other than the aforementioned formula (A), Y should be a group of the formula (B)

(B)

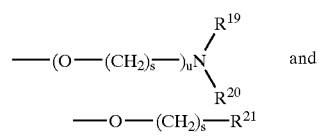

wherein Q$^2$ is a benzene ring, and R$^{18}$ is a group selected from

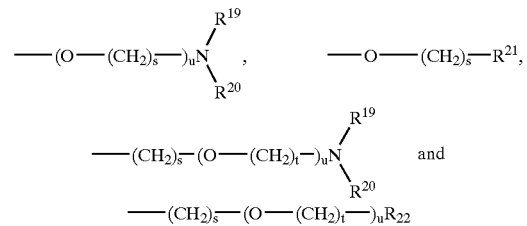

wherein s is an integer of 1 to 5, u is an integer of 1 or 2, R$^{19}$ and R$^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{21}$ is aryl, heteroaryl, hydroxysulfonyloxy, sulfo or carboxy, or $Q^2$ is a furan ring, and $R^{18}$ is arylalkyloxyalkyl or a group selected from

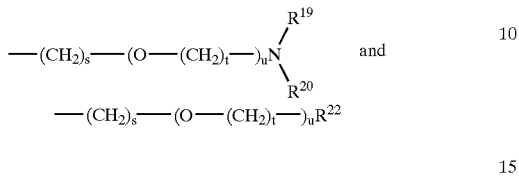

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy, wherein the aforementioned arylalkyl, heteroarylthioalkyl, arylthioalkyl, arylalkylthioalkyl, phthalimidoalkyl, aryl, heteroaryl and heteroarylalkyl may have a substituent [hereinafter to be referred to as intermediate compound (II)].

(9) The compound of the aforementioned (8) wherein (i) $R^3$ is a group of the formula (A)

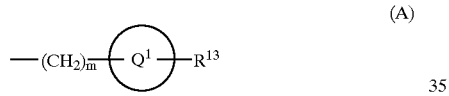

wherein $Q^1$ is a benzene ring, m is an integer of 0 to 3, and $R^{13}$ is guanidino, hydroxysulfonyloxy, sulfo or a group selected from

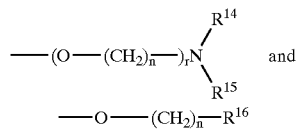

wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, and Y is furyl, thienyl, pyrrolyl, pyridyl, thiazolyl, phenyl, alkoxyphenyl, or phenyl substituted by $-NR^{19}R^{20}$ wherein $R^{19}$ and $R^{20}$ are the same or different and each is alkyl, or (ii) $R^3$ is alkyl or a group of

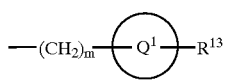

wherein $Q^1$ is a benzene ring, m is an integer of 0 to 3, and $R^{13}$ is hydrogen, and Y is a group of the formula (B)

wherein $Q^2$ is a benzene ring, and $R^{18}$ is a group selected from

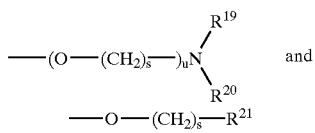

wherein s is an integer of 1 to 5, u is an integer of 1 or 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{21}$ is aryl, heteroaryl, hydroxysulfonyloxy, sulfo or carboxy, or $Q^2$ is a furan ring, and $R^{18}$ is arylalkyloxyalkyl or a group selected from

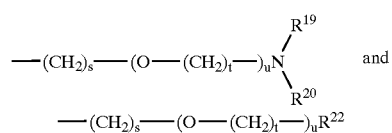

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy.

(10) A pharmaceutical composition comprising a hydroxamic acid derivative of any of the aforementioned (1) to (7) or a pharmacologically acceptable salt thereof, and a pharmacologically acceptable carrier.

(11) The pharmaceutical composition of the aforementioned (10), which is an inhibitor of TNF α production.

The symbols used in the present specification are explained in the following.

The alkyl at $R^1$, $R^2$, $R^3$, $R^{11}$, $R^{12}$, $R^{14}$, $R^{15}$, $R^{19}$, $R^{20}$ and $R^{23}$ may be a linear or branched chain preferably having 1 to 10 carbon atoms. Examples thereof include methyl, ethyl, n-propyl, isopropyl, n-butyl, isobutyl, sec-butyl, tert-butyl, n-pentyl, isopentyl, n-hexyl, n-octyl, n-decyl and the like.

The arylalkyl at $R^1$, $R^2$, $R^{11}$, $R^{12}$, $R^{14}$, $R^{15}$, $R^{19}$, $R^{20}$ and $R^{23}$ is that wherein the alkyl moiety may be a linear or branched chain preferably having 1 to 6 carbon atoms, and the aryl moiety is preferably a phenyl, naphthyl or ortho-fused bicyclic group having 8 to 10 ring-forming atoms, wherein at least one ring is an aromatic ring (e.g., indenyl and the like). Examples thereof include benzyl, phenethyl, 3-phenylpropyl, 1-naphthylmethyl, 2-naphthylmethyl, 2-(1-naphthyl)ethyl, 2-(2-naphthyl)ethyl, 3-(1-naphthyl)propyl, 3-(2-naphthyl)propyl and the like.

The heteroarylthioalkyl at $R^1$ and $R^{12}$ is that wherein the alkyl moiety may be a linear or branched chain preferably having 1 to 6 carbon atoms, and the heteroaryl moiety is a 5- or 6-membered cyclic group preferably having a carbon atom and 1 to 4 heteroatoms (e.g., oxygen, sulfur or nitrogen), or an ortho-fused bicyclic heteroaryl derived therefrom, which has 8 to 10 ring-forming atoms, particularly a benzo derivative wherein the heterocycle is fused with benzene ring, or a derivative wherein the heterocycle is fused with propenylene, trimethylene or tetramethylene, a stable N-oxide thereof and the like. Examples of the heteroaryl moiety include pyrrolyl, pyrrolinyl, furyl, thienyl, oxazolyl, isoxazolyl, imidazolyl, thiazolyl, isothiazolyl, pyrazolyl, 1,2,3-triazolyl, 1,2,4-triazolyl, tetrazolyl, 1,3,4-oxadiazolyl, 1,2,4-oxadiazolyl, 1,3,4-thiadiazolyl, 1,2,4-thiadiazolyl, pyridyl, pyranyl, pyrazinyl, pyrimidinyl, pyridazinyl, 1,2,4-triazinyl, 1,2,3-triazinyl, 1,3,5-triazinyl, 1,2,5-oxathiazinyl, 1,2,6-oxathiazinyl, benzoxazolyl, benzothiazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl, benzoxazinyl and the like.

Examples of heteroarylthioalkyl include 2-pyrrolylthiomethyl, 2-pyridylthiomethyl, 3-pyridylthiomethyl, 4-pyridylthiomethyl, 2-thienylthiomethyl and the like.

The arylthioalkyl at $R^1$ and $R^{12}$ is that wherein the alkyl moiety may be a linear or branched chain preferably having 1 to 6 carbon atoms, and the aryl moiety is the same as the aryl moiety of the above-mentioned arylalkyl. Examples thereof include phenylthiomethyl, 1-naphthylthiomethyl, 2-naphthylthiomethyl and the like.

The alkylthioalkyl at $R^1$ and $R^{12}$ is that wherein the alkyl moiety of alkylthio moiety is the same as the above-mentioned alkyl, and the remaining alkyl moiety may be a linear or branched chain preferably having 1 to 6 carbon atoms. Examples thereof include methylthiomethyl, ethylthiomethyl, n-propylthiomethyl, isopropylthiomethyl, n-butylthiomethyl, isobutylthiomethyl, sec-butylthiomethyl, tert-butylthiomethyl and the like.

The arylalkylthioalkyl at $R^1$ and $R^{12}$ is that wherein the arylalkyl moiety is the same as the above-mentioned arylalky. The remaining alkyl moiety may be a linear or branched chain preferably having 1 to 6 carbon atoms. Examples thereof include benzylthiomethyl, phenethylthiomethyl and the like.

The alkyl moiety of phthalimidoalkyl at $R^1$ and $R^{12}$ may be a linear or branched chain preferably having 1 to 6 carbon atoms. Examples thereof include phthalimidomethyl, 2-phthalimidoethyl and the like.

The alkenyl at $R^1$ and $R^{12}$ preferably has 2 to 6 carbon atoms, and examples thereof include vinyl, allyl, 3-butenyl, 5-hexenyl and the like.

The aryl at $R^2$, $R^{11}$, $R^{14}$, $R^{15}$, $R^{19}$, $R^{20}$, $R^{21}$ and $R^{23}$ the same as the aryl moiety of the above-mentioned arylalkyl, which is preferably phenyl.

The "A" in "—$(CH_2)_l$—A" at $R^1$ and $R^{12}$ is an N-heterocycle bonded by an N atom, which is exemplified by the following groups.

(i)
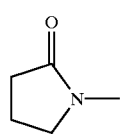

-continued (ii)
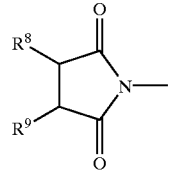

(iii)
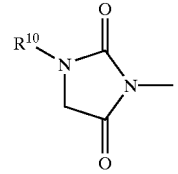

(iv)
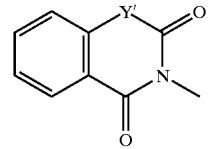

(v)
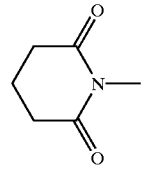

(vi)
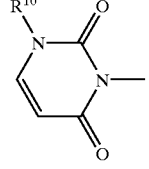

(vii)
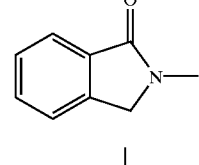

(viii)
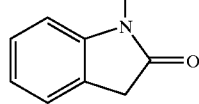

wherein $R^8$ and $R^9$ are each hydrogen or show, in combination, a different bond, to form a double bond, $R^{10}$ is hydrogen, lower alkyl or phenyl, X' is —CO—, —$CH_2$—, —CH(lower alkyl)—, —C(lower alkyl)$_2$—, —NH—, —N(lower alkyl)— or —O—, and Y' is —O—, —NH— or —N(lower alkyl)—.

As used herein, the lower alkyl has 1 to 6 carbon atoms and may be a linear or branched chain. Examples thereof include methyl, ethyl, n-propyl, isopropyl, n-butyl, isobutyl, sec-butyl, tert-butyl, n-pentyl, isopentyl, n-hexyl and the like.

Examples of the N-heterocycle include 2-oxo-1-pyrrolidinyl, 1-oxoisoindolin-2-yl, 2-oxoindolin-1-yl, 2,5-dioxo-1-pyrrolidinyl, 1,2-dimethyl-3,5-dioxo-1,2,4-triazolidin-4-yl, 2,5-dioxo-3-methyl-1-imidazolidinyl, 2,5-dioxo-3,4,4-trimethyl-1-imidazolidinyl, 3,5-dioxo-2-methyl-1,2,4-oxadiazolidin-4-yl, 3-methyl-2,4,5-trioxo-1-imidazolidinyl, 2,5-dioxo-3-phenyl-1-imidazolidinyl, 2,6- dioxopiperidino and the like. Preferred are the rings of the formulas (ii), (iii), (vii) and (viii), such as 1-oxoisoindolin-2-yl, 2-oxoindolin-1-yl, 1,2-dimethyl-3,5-dioxo-1,2,4-triazolidin-4-yl, 2,5-dioxo-3-methyl-1-imidazolidinyl, 2,5-dioxo-3,4,4-trimethyl-1-imidazolidinyl, more preferred are the rings of the formulas (ii) and (iii), such as 1,2-dimethyl-3,5-dioxo-1,2,4-triazolidin-4-yl, 2,5-dioxo-3-methyl-1-imidazolidinyl and 2,5-dioxo-3,4,4-trimethyl-1-imidazolidinyl.

The heteroarylalkyl at $R^2$, $R^{11}$, $R^{14}$, $R^{15}$, $R^{19}$, $R^{20}$, $R^{21}$ and $R^{23}$ is that wherein the alkyl moiety may be a linear or branched chain preferably having 1 to 6 carbon atoms, and the heteroaryl moiety is the same as the heteroaryl moiety of the above-mentioned heteroarylthioalkyl. Examples thereof include 2-pyrrolylmethyl, 2-pyridylmethyl, 3-pyridylmethyl, 4-pyridylmethyl, 2-thienylmethyl, 2-(2-pyridyl)ethyl, 2-(3-pyridyl)ethyl, 2-(4-pyridyl)ethyl, 3-(2-pyrrolyl)propyl and the like.

The cycloalkyl at $R^2$ preferably has 3 to 7 carbon atoms. Examples thereof include cyclopropyl, cyclobutyl, cyclopentyl, cyclohexyl, cycloheptyl and the like.

The cycloalkylalkyl at $R^2$ is that wherein the alkyl moiety may be a linear or branched chain preferably having 1 to 6 carbon atoms, and the cycloalkyl moiety is the same as the above-mentioned cycloalkyl. Examples thereof include cyclopropylmethyl, 2-cyclobutylethyl, cyclopentylmethyl, 3-cyclopentylpropyl, cyclohexylmethyl, 2-cyclohexylethyl, cycloheptylmethyl and the like.

The aromatic hydrocarbon ring at $Q^1$ and $Q^2$ is exemplified by a benzene ring, a naphthalene ring, or an ortho-fused bicyclic hydrocarbon ring having 8 to 10 ring-forming atoms, wherein at least one ring is an aromatic ring (e.g., indene and the like). Preferred is a benzene ring.

The aromatic heterocycle at $Q^1$ and $Q^2$ is exemplified by 5- or 6-membered ring having a carbon atom and 1 to 4 heteroatoms (e.g., oxygen, sulfur or nitrogen), an ortho-fused bicyclic aromatic heterocycle having 8 to 10 ring-forming atoms derived therefrom, particularly, a benzo derivative wherein the heterocycle is fused with benzene ring. Examples of aromatic heterocycle include pyrrole, furan, thiophene, oxazole, isoxazole, imidazole, thiazole, isothiazole, pyrazole, 1,2,3-triazole, 1,2,4-triazole, tetrazole, 1,3,4-oxadiazole, 1,2,4-oxadiazole, 1,3,4-thiadiazole, 1,2,4-thiadiazole, pyridine, pyrazine, pyrimidine, pyridazine, 1,2,4-triazine, 1,2,3-triazine, 1,3,5-triazine, 1,2,5-oxathiazine, 1,2,6-oxathiazine, benzoxazole, benzothiazole, benzimidazole, thianaphthene, isothianaphthene, benzofuran, isobenzofuran, chromene, isoindole, indole, indazole, isoquinoline, quinoline, phthalazine, quinoxaline, quinazoline, cinnoline, benzoxazine and the like. Preferred are pyrrole, furan, thiophene, thiazole and pyridine.

The heteroaryl at $R^{16}$ and $R^{21}$ is the same as the heteroaryl moiety of the above-mentioned heteroarylthioalkyl, which is preferably pyridyl.

The above-mentioned arylalkyl, heteroarylthioalkyl, arylthioalkyl, arylalkylthioalkyl, phthalimidoalkyl, aryl, heteroaryl and heteroarylalkyl are optionally substituted by one or more substituents selected from halogen (e.g., fluorine, chlorine, bromine and iodine), hydroxy, nitro, cyano, trifluoromethyl, lower alkyl (provided that the lower alkyl does not substitute at the alkyl moiety of arylalkyl, heteroarylthioalkyl, arylthioalkyl, arylalkylthioalkyl and phthalimidoalkyl), alkoxy, alkylthio, formyl, acyloxy, oxo, phenyl, arylalkyl, carboxyl, a group of the formula: —COORa wherein Ra is lower alkyl, arylalkyl or aryl, carbamoyl, amino, (lower alkyl)amino, di(lower alkyl) amino, guanidino, hydroxysulfonyloxy, sulfo, arylalkyloxyalkyl and the like.

As used herein, lower alkyl, arylalkyl and aryl are the same as those mentioned above. Alkoxy may be a linear or branched chain preferably having 1 to 6 carbon atoms. Examples thereof include methoxy, ethoxy, n-propoxy, isopropoxy, n-butoxy, tert-butoxy and the like. Alkylthio is that wherein the alkyl moiety may be a linear or branched chain preferably having 1 to 6 carbon atoms. Examples thereof include methylthio, ethylthio, n-propylthio, isopropylthio and the like. Acyloxy is alkanoyloxy which may be a linear or branched chain preferably having 2 to 6 carbon atoms. Examples thereof include acetyloxy, propionyloxy, butyryloxy, valeryloxy, pivaloyloxy, hexanoyloxy and the like. Arylalkyloxyalkyl is that wherein the arylalkyl moiety is the same as the above-mentioned arylalkyl, and the remaining alkyl moiety may be a linear or branched chain preferably having 1 to 6 carbon atoms. Examples thereof include benzyloxymethyl, phenethyloxymethyl and the like. The lower alkyl moiety of (lower alkyl)amino and di(lower alkyl)amino may be a linear or branched chain having 1 to 6 carbon atoms. Examples of (lower alkyl)amino include methylamino, ethylamino, propylamino, isopropylamino, butylamino, isobutylamino, sec-butylamino, tert-butylamino, pentylamino, hexylamino and the like. Examples of di(lower alkyl)amino include dimethylamino, diethylamino, dipropylamino, diisopropylamino, dibutylamino, diisobutylamino, di-sec-butylamino, di-tert-butylamino, dipentylamino, dihexylamino, ethylmethylamino, methylpropylamino, butylmethylamino, ethylpropylamino, ethylbutylamino and the like.

The halogen, lower alkyl, alkoxy, alkylthio, acyloxy, arylalkyl, —COORa (Ra is as defined above) and arylalkyloxyalkyl at $R^{13}$ and $R^{16}$ are as defined above.

The optionally substituted heterocycle formed by $R^{14}$ and $R^{15}$ together with the adjacent nitrogen atom, and the optionally substituted heterocycle formed by $R^{19}$ and $R^{20}$ together with the adjacent nitrogen atom is a 4 to 7-membered ring having a carbon atom and at least one nitrogen atom, which may have, in the ring, at least one atom selected from nitrogen, oxygen and sulfur, as a further heteroatom, wherein the carbon atom constituting the ring is optionally substituted by oxo. In addition, an aromatic ring, such as benzene ring and the like, may be fused therewith utilizing the adjacent two carbon atoms constituting these heterocycles. Examples thereof include azetidino, 1-pyrrolidinyl, piperidino, 1-piperazinyl, morpholino, thiomorpholino, oxothiomorpholino, dioxothiomorpholino, 2-oxo-1-quinazolinyl and the like.

When the heterocycle has a nitrogen atom as a further heteroatom in the ring, such as 1-piperazinyl, lower alkyl (as defined above), arylalkyl (as defined above), and heteroarylalkyl (as defined above), aryl (as defined above), heteroaryl (as defined above), a group of the formula: —COORa (Ra is as defined above) or acyl may be substituted on the nitrogen atom. As used herein, acyl is expressed by —CORa wherein Ra is as defined above.

Preferable examples of optionally substituted heterocycle include 1-pyrrolidinyl, piperidino, morpholino and 1-piperazinyl wherein the 4-position nitrogen atom is optionally substituted by lower alkyl.

With regard to the formula (I) and the formula (II) of the present invention, a preferable mode is as follows.

(i) $R^3$ is a group of the formula (A)

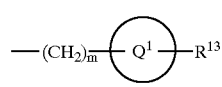
(A)

wherein $Q^1$ is a benzene ring, m is an integer of 0 to 3, and $R^{13}$ is guanidino, hydroxysulfonyloxy, sulfo or a group selected from

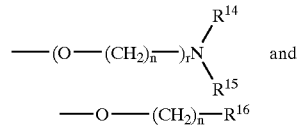
and wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, or (ii) when $R^3$ is a group other than the aforementioned formula (A),
Y should be a group of the formula (B)

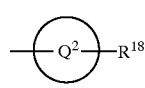
(B)

wherein $Q^2$ is a benzene ring, and $R^{18}$ is a group selected from

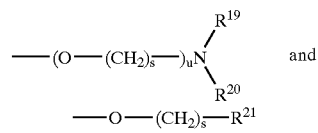
and wherein s is an integer of 1 to 5, u is an integer of 1 or 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{21}$ is aryl, heteroaryl, hydroxysulfonyloxy, sulfo or carboxy, or
$Q^2$ is a furan ring, and $R^{18}$ is arylalkyloxyalkyl or a group selected from

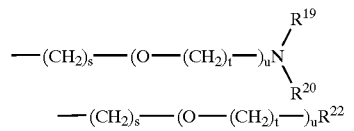
and wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy.

With regard to the formula (I) and the formula (II) of the present invention, a more preferable mode is as follows.

(i) $R^3$ is a group of the formula (A)

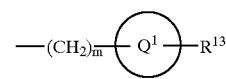
(A)

wherein $Q^1$ is a benzene ring, m is an integer of 0 to 3, and $R^{13}$ is guanidino, hydroxysulfonyloxy, sulfo or a group selected from

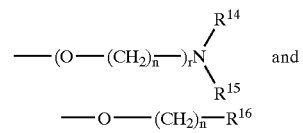
and wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, and Y is furyl, thienyl, pyrrolyl, pyridyl, thiazolyl, phenyl, alkoxyphenyl, or phenyl substituted by —$NR^{19}R^{20}$
wherein $R^{19}$ and $R^{20}$ are the same or different and each is alkyl, or (ii) $R^3$ is alkyl or a group of the formula

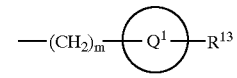

wherein $Q^1$ is a benzene ring, m is an integer of 0 to 3, and $R^{13}$ is hydrogen, and
Y is a group of the formula (B)

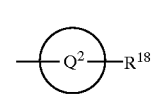
(B)

wherein $Q^2$ is a benzene ring, and $R^{18}$ is a group selected from

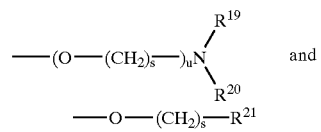
and wherein s is an integer of 1 to 5, u is an integer of 1 or 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{21}$ is aryl, heteroaryl, hydroxysulfonyloxy, sulfo or carboxy, or
$Q^2$ is a furan ring, and $R^{18}$ is arylalkyloxyalkyl or a group selected from $$-(CH_2)_s-(O-(CH_2)_t-)_u N \begin{matrix} R^{19} \\ \\ R^{20} \end{matrix}$$ and $$-(CH_2)_s-(O-(CH_2)_t-)_u R^{22}$$

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy.

With regard to the formula (I) and the formula (II) of the present invention, a particularly preferable mode is as follows.

(a) $R^3$ is a group of the formula $$-(CH_2)_m-\!\!\!\left(\!\!Q^1\!\!\right)\!\!-R^{13}$$

wherein $Q^1$ is a benzene ring, m is 1, and $R^{13}$ is guanidino, hydroxysulfonyloxy, sulfo or a group of the formula $$-(O-(CH_2)_n-)_r N \begin{matrix} R^{14} \\ \\ R^{15} \end{matrix}$$

wherein n is an integer of 1 to 5, r is an integer of 1 or 2, $R^{14}$ and $R^{15}$ are the same or different and each is hydrogen or alkyl, or $R^{14}$ and $R^{15}$ may form, together with the adjacent nitrogen atom, an optionally substituted heterocycle, and Y is furyl, thienyl, pyrrolyl, pyridyl, thiazolyl, phenyl, alkoxyphenyl, or phenyl substituted by $-NR^{19}R^{20}$ wherein $R^{19}$ and $R^{20}$ are the same or different and each is alkyl.

(b) $R^3$ is a group of the formula $$-(CH_2)_m-\!\!\!\left(\!\!Q^1\!\!\right)\!\!-R^{13}$$

wherein $Q^1$ is a benzene ring, m is 1, and $R^{13}$ is guanidino, hydroxysulfonyloxy, sulfo or a group of the formula $$-(O-(CH_2)_n-)_r N \begin{matrix} R^{14} \\ \\ R^{15} \end{matrix}$$

wherein n is an integer of 1 to 5, r is 1, $R^{14}$ and $R^{15}$ are the same or different and each is hydrogen or alkyl, and Y is furyl, thienyl, pyrrolyl, pyridyl, thiazolyl, phenyl, alkoxyphenyl, or phenyl substituted by $-NR^{19}R^{20}$ wherein $R^{19}$ and $R^{20}$ are the same or different and each is alkyl.

(c) $R^3$ is alkyl or benzyl and Y is a group of the formula $$-\!\!\!\left(\!\!Q^2\!\!\right)\!\!-R^{18}$$

wherein $Q^2$ is a benzene ring, and $R^{18}$ is a group selected from $$-(O-(CH_2)_s-)_u N \begin{matrix} R^{19} \\ \\ R^{20} \end{matrix}$$ and $$-O-(CH_2)_s-R^{21}$$

wherein s is an integer of 1 to 5, u is an integer of 1 or 2, $R^{19}$ and $R^{20}$ are the same or different and each is hydrogen or alkyl, or $R^{19}$ and $R^{20}$ may form, together with the adjacent nitrogen atom, an optionally substituted heterocycle, and $R^{21}$ is phenyl or pyridyl.

(d) $R^3$ is alkyl or benzyl and Y is a group of the formula $$-\!\!\!\left(\!\!Q^2\!\!\right)\!\!-R^{18}$$

wherein $Q^2$ is a benzene ring, and $R^{18}$ is a group selected from $$-(O-(CH_2)_s-)_u N \begin{matrix} R^{19} \\ \\ R^{20} \end{matrix}$$ and $$-O-(CH_2)_s-R^{21}$$

wherein s is an integer of 1 to 5, u is 1, $R^{19}$ and $R^{20}$ are the same or different and each is hydrogen or alkyl, or $R^{19}$ and $R^{20}$ may form, together with the adjacent nitrogen atom, a heterocycle selected from 1-pyrrolidinyl, piperidino, morpholino and 1-piperazinyl wherein the 4-position nitrogen atom is optionally substituted by lower alkyl, and $R^{21}$ is phenyl or pyridyl.

(e) $R^3$ is alkyl or benzyl and Y is a group of the formula $$-\!\!\!\left(\!\!Q^2\!\!\right)\!\!-R^{18}$$

wherein $Q^2$ is a furan ring, and $R^{18}$ is phenylalkyloxyalkyl or a group selected from $$-(CH_2)_s-(O-(CH_2)_t-)_u N \begin{matrix} R^{19} \\ \\ R^{20} \end{matrix}$$ and $$-(CH_2)_s-(O-(CH_2)_t-)_u R^{22}$$

wherein s and t are the same or different and each is an integer of 1 to 5, u is an integer of 0 to 2, $R^{19}$ and $R^{21}$ are the same or different and each is hydrogen or alkyl, or $R^{19}$ and $R^{20}$ may form, together with the adjacent nitrogen atom, an optionally substituted heterocycle, and $R^{22}$ is hydroxy.

(f) $R^3$ is alkyl or benzyl and Y is a group of the formula

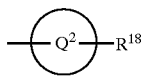

wherein $Q^2$ is a furan ring, and $R^{18}$ is benzyloxymethyl or a group selected from

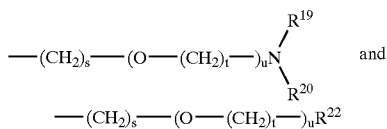

wherein s and t are the same or different and each is an integer of 1 to 5, u is an integer of 0 or 1, $R^{19}$ and $R^{21}$ are the same or different and each is hydrogen or alkyl, and $R^{22}$ is hydroxy.

Another preferable mode of the present invention is as follows.

A preferable example of a group of the formula

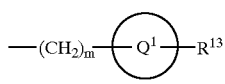

at $R^3$ is a group wherein $Q^1$ is a benzene ring, and $R^{13}$ is hydrogen, guanidino, hydroxysulfonyloxy or a group of the formula

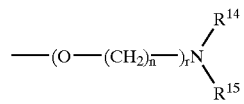

wherein n is an integer of 1 to 5, r is an integer of 0 to 2, $R^{14}$ and $R^{15}$ are the same or different and each is alkyl, or $R^{14}$ and $R^{15}$ may form, together with the adjacent nitrogen atom, an optionally substituted heterocycle.

More preferable example is a group wherein $Q^1$ is a benzene ring and $R^{13}$ is hydrogen.

A preferable example of a group of the formula

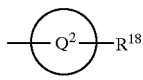

at Y is a group wherein $Q^2$ is a benzene ring or an aromatic heterocycle selected from pyrrole, furan, thiophene, thiazole and pyridine, and $R^{18}$ is hydrogen or a group selected from

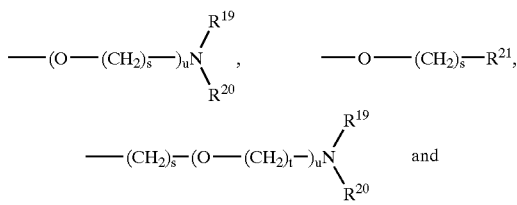

-continued
—(CH$_2$)$_s$—(O—(CH$_2$)$_t$—)$_u$R$_{22}$ wherein s and t are the same or different and each is an integer of 1 to 5, u is an integer of 0 to 2, $R^{19}$ and $R^{20}$ are the same or different and each is alkyl, or $R^{19}$ and $R^{20}$ may form, together with the adjacent nitrogen atom, an optionally substituted heterocycle, $R^{21}$ is aryl or heteroaryl phenyl, and $R^{22}$ is hydroxy.

More preferable example is a group wherein $Q^2$ is a benzene ring or an aromatic heterocycle selected from pyrrole, furan, thiophene, thiazole and pyridine, and $R^{18}$ is hydrogen or a group of the formula

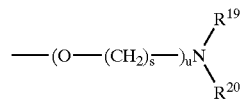

wherein s is an integer of 1 to 5, u is an integer of 0 to 2, $R^{19}$ and $R^{20}$ are the same or different and each is alkyl, or $R^{19}$ and $R^{20}$ may form, together with the adjacent nitrogen atom, an optionally substituted heterocycle.

The hydroxy-protecting group at X may be, for example, arylalkyl (as defined above), aryl (as defined above), heteroaryl (as defined above), silyl (e.g., trimethylsilyl, tert-butyldimethylsilyl, tert-butyldiphenylsilyl and the like), 2-tetrahydropyranyl, p-methoxybenzyl, tert-butyl and the like. The arylalkyl, aryl and heteroaryl may have one or more substituents exemplified above. The hydroxy-protecting group is preferably silyl, 2-tetrahydropyranyl, benzyl and the like.

The hydroxamic acid derivative and a pharmacologically acceptable salt thereof represented by the formula (I) may have an asymmetric carbon and can exist as an optically active compound and racemate. The racemate can be resolved into respective optically active compounds by a method known per se. When the hydroxamic acid derivative and a pharmacologically acceptable salt thereof have an additional asymmetric carbon, the compound can exist as a mixture of diastereomers or a single diastereomer, all of which can be separated into respective compounds by a method known per se.

The hydroxamic acid derivative and a pharmacologically acceptable salt thereof can show polymorphism, can exist as two or more tautomers, and can exist as a solvate (e.g., ketone solvate, hydrate and the like).

Therefore, the present invention encompasses all of the above-mentioned stereoisomers, optical isomers, polymorphs, tautomers, solvates, mixtures thereof and the like. The optically active compounds, racemates and diastereomers are also encompassed in the present invention.

The pharmacologically acceptable salts of the hydroxamic acid derivative may be, for example, alkali metal salts (e.g., salt with lithium, sodium, potassium and the like), alkaline earth metal salts (e.g., salt with calcium, magnesium and the like), aluminum salt, ammonium salt, salts with organic base (e.g., salt with triethylamine, morpholine, piperidine, triethanolamine and the like) and the like.

Other pharmacologically acceptable salts may be, for example, inorganic acid addition salts (e.g., salt with hydrochloric acid, hydrobromic acid, hydroiodic acid, sulfuric acid, phosphoric acid and the like), organic acid addition salts (e.g., salt with methanesulfonic acid, benzenesulfonic acid, p-toluenesulfonic acid, formic acid, acetic acid, trifluoroacetic acid, oxalic acid, citric acid, malonic acid, fumaric acid, glutaric acid, adipic acid, maleic acid, tartaric acid, succinic acid, mandelic acid, malic acid and the like), salt with amino acid (e.g., salt with glutamic acid, aspartic acid, hystidine, lysine, arginine and the like) and the like. For crystallization, oxalic acid can be used to give a salt.

The preferable modes of the hydroxamic acid derivative or a pharmacologically acceptable salt thereof of the formula (I) include a hydroxamic acid derivative or a pharmacologically acceptable salt thereof of the formula (I) wherein $R^1$ is phthalimidomethyl, a hydroxamic acid derivative or a pharmacologically acceptable salt thereof of the formula (I) wherein $R^2$ is isobutyl, a hydroxamic acid derivative or a pharmacologically acceptable salt thereof of the formula (I) wherein $R^3$ is benzyl optionally substituted by a substituent selected from guanidino, hydroxysulfonyloxy, sulfo,

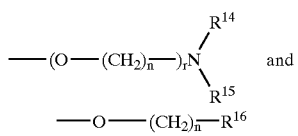

wherein n an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, and the like. The preferable compounds including these preferable modes are shown in Examples 1–11, 12, 18, 23, 25, 27, 33, 35, 37, 39, 40, 44, 84, 88, 91, 112, 115, 117, 120, 147, 152, 155, 191, 194 and 245 to be mentioned later.

The production methods of the hydroxamic acid derivative and a pharmacologically acceptable salt thereof of the present invention are shown in the following.

Scheme 1

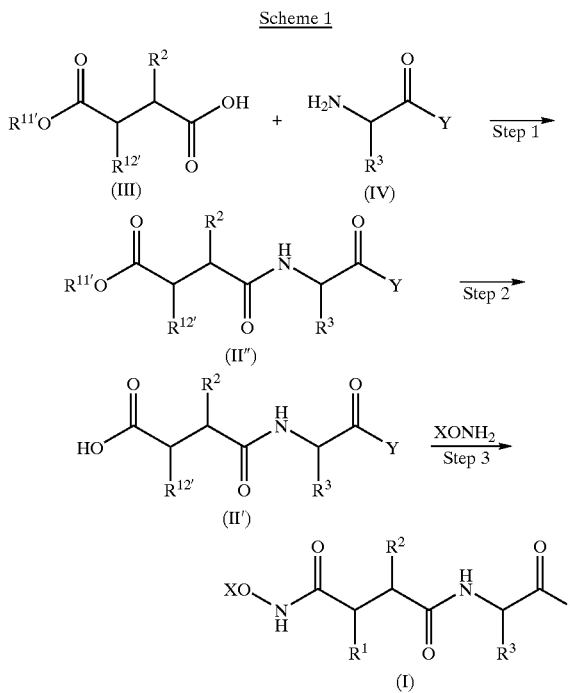

wherein $R^{11'}$ is the same as $R^{11}$ (except hydrogen), $R^{12'}$ is the same as $R^1$, and $R^1$, $R^2$, $R^3$, X and Y are as defined above.

As shown in the above-mentioned Scheme 1, the hydroxamic acid derivative and a pharmacologically acceptable salt thereof of the present invention can be basically prepared using carboxylic acid (III) as a starting compound and by using amino derivative (IV) to prepare an intermediate compound (II') according to the C end activation method in peptide synthesis (see Pepuchidogousei no kiso to jikken, Izumiya et al., Maruzen Shoten, p 91), converting the intermediate compound (II') to a succinic acid derivative (II'') and reacting the succinic acid derivative (II'') with hydroxylamine: $XONH_2$ wherein X is as defined above. The starting compound, carboxylic acid (III), is described in publications (Japanese Patent Application under PCT laid-open under Kohyo No. 6-506445, JP-A-4-352757, JP-A-7-157470, Japanese Patent Application under PCT laid-open under Kohyo No. 4-502008, JP-A-6-65196, WO96/33968, WO94/21625 and the like), and can be prepared according to a conventional method based on these publications.

The amino derivative (IV) can be produced, for example, by the method to be mentioned later.

Each step is explained in detail in the following.

Step 1

In Step 1, an intermediate compound (II') is prepared by reacting carboxylic acid (III) and amino derivative (IV). Typical methods are shown in the following.

Step 1-1) Method Using Mixed Acid Anhydride

The intermediate compound (II') can be obtained by reacting carboxylic acid (III) with isobutyl chlorocarbonate in the presence of an amine base, such as triethylamine, N-methylmorpholine and the like, and reacting the resulting compound with amino derivative (IV). The solvent used is an aprotic solvent such as tetrahydrofuran (THF), methylene chloride, ethyl acetate, N,N-dimethylformamide (DMF) and the like, and the reaction proceeds at a temperature of from −15° C. to room temperature.

Step 1-2) Method Using Acid Chloride

The carboxylic acid (III) is reacted with oxalyl chloride or thionyl chloride to give an acid chloride. The solvent used is methylene chloride, or a hydrocarbon solvent such as benzene, toluene and the like, and the reaction proceeds at a temperature of from −15° C. to room temperature or under heating. The intermediate compound (II') can be obtained by reacting the resulting acid chloride with amino derivative (IV) in the presence of an amine base such as triethylamine, pyridine and the like. The solvent used is an aprotic solvent such as THF, ethyl acetate, DMF, methylene chloride, benzene, toluene and the like, and the reaction proceeds at a temperature of from −15° C. to room temperature or under heating.

Step 1-3) Method Using DCC-HOBt Method (Coupling Method)

The intermediate compound (II') can be obtained by reacting carboxylic acid (III), amino derivative (IV) and 1-hydroxybenzotriazole (HOBt) with a condensing agent, such as 1,3-dicyclohexylcarbodiimide (DCC), benzotriazol-1-yloxytris(dimethylamino)phosphonium hexafluorophosphate (BOP reagent) and the like in the presence of an amine base, such as triethylamine, N-methylmorpholine and the like, at a temperature not higher than room temperature. The solvent used is an aprotic solvent such as THF, methylene chloride, ethyl acetate, DMF, pyridine and the like.

Step 1-4) Method Using Active Ester

The carboxylic acid (III) and a phenol derivative, such as pentafluorophenol and the like, or N-hydroxysuccinimide are reacted with a condensing agent, such as DCC and the like, to give an active ester. An amine base may be used as necessary, where examples thereof include triethylamine, N-methylmorpholine and the like. The solvent used is an aprotic solvent, such as THF, DMF, methylene chloride and the like, and the reaction proceeds at a temperature not higher than room temperature. The intermediate compound (II') can be obtained by reacting the resulting active ester with amino derivative (IV). An amine base may be used as necessary, where examples thereof include triethylamine, N-methylmorpholine and the like. The solvent used is an aprotic solvent, such as THF, DMF, methylene chloride and the like, and the reaction proceeds at a temperature not higher than room temperature.

Step 2

In Step 2, the intermediate compound (II') is converted to a succinic acid derivative (II"). For example, when $R^{11'}$ can be removed with an acid, such as tert-butyl, the intermediate compound (II') is reacted with a hydrogen chloride solution or trifluoroacetic acid to give succinic acid derivative (II"). The solvent used is an ether solvent, such as 1,4-dioxane and the like or methylene chloride and the like, and the reaction proceeds at a temperature not higher than room temperature.

Step 3

In Step 3, the succinic acid derivative (II") is reacted with hydroxylamine:$XONH_2$, wherein X is as defined above, with or without protection with silyl (e.g., trimethylsilyl, tert-butyldimethylsilyl, tert-butyldiphenylsilyl and the like), tert-butyl, benzyl, 2-tetrahydropyranyl (Chem. Pharm. Bull. Jpn. 23, 167, 1975) and the like. The reaction conditions are the same as in Step 1. When protected hydroxylamine is used, the hydroxylamine-protecting group can be eliminated, after reaction, under the same deprotection conditions as those generally employed for the deprotection of hydroxy-protecting group.

The intermediate compound (II') can be also produced by the method shown in the following Scheme 2.

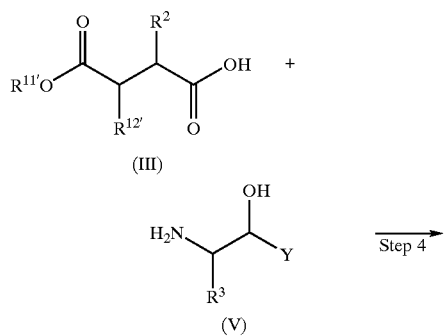

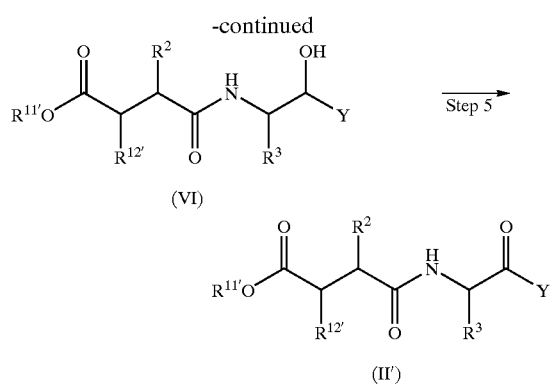

wherein $R^2$, $R^3$, $R^{11'}$, $R^{12'}$ and Y are as defined above.

Step 4

In Step 4, carboxylic acid (III) and an amino derivative (V) are reacted to give compound (VI). This step is carried out by a method similar to that used in Step 1.

The amino derivative (V) can be produced, for example, by the method to be mentioned later.

Step 5

In Step 5, compound (VI) is oxidized to give intermediate compound (II'). As the oxidation method, exemplified are preferably Moffatt oxidation, Swern oxidation, oxidation using Dess-Martin periodinane, Collins oxidation, oxidation using manganese dioxide and the like. The inert solvent to be used is preferably a halogenated hydrocarbon solvent, such as methylene chloride, chloroform and the like, or an aromatic hydrocarbon solvent, such as benzene, toluene, xylene and the like. While the reaction temperature varies depending on the starting compound, oxidation method and the like to be employed, it is generally from −78° C. to 50° C. While the reaction time varies depending on the starting compound, oxidation method and the like to be used, it is generally 30 minutes–24 hours.

A desired substituent $R^1$ can be introduced by the use of carboxylic acid (III) having this substituent, according to the method shown in the above-mentioned Scheme 1 or 2, without going through a specific step. In addition, for example, the following method shown in Scheme 3 can be employed.

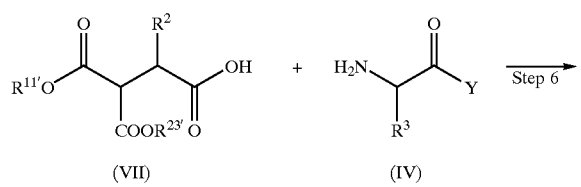

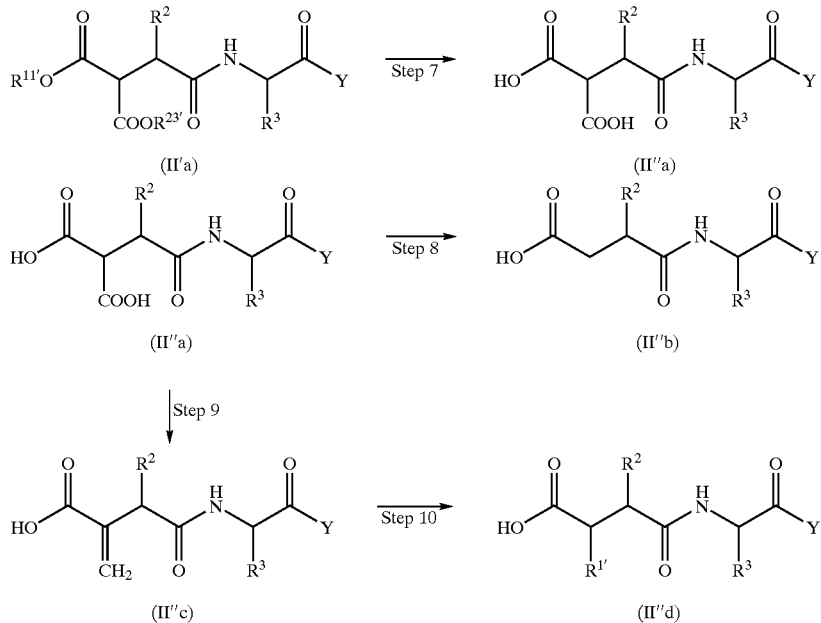

wherein $R^1$ is heteroarylthioalkyl, arylthioalkyl, alkylthioalkyl or arylalkylthioalkyl, $R^{23'}$ is the same as $R^{23}$ (except hydrogen), and $R^2$, $R^3$, $R^{11'}$ and Y are as defined above.

Step 6

In Step 6, carboxylic acid (VII) is used as a starting compound, and intermediate compound (II'a) is obtained by the method of Step 1 in the above-mentioned Scheme 1. The carboxylic acid (VII) to be the starting compound is described in a publication (JP-A-7-157470), and can be prepared by a conventional method based on this publication.

Step 7

In Step 7, the substituents $R^{11'}$ and $R^{23'}$ of intermediate compound (II'a) are removed to give a succinic acid derivative (II''a). For example, when $R^{11'}$ and $R^{23'}$ are benzyl, a general hydrogenation reaction is carried out in the presence of a metal catalyst at normal pressure or under pressurization. Examples of the metal catalyst include palladium carbon and palladium black and the like. The solvent may be an ether solvent, such as 1,4-dioxane and the like, an ester solvent, such as ethyl acetate and the like, or an alcohol solvent, such as methanol, ethanol, isopropyl alcohol and the like, and the reaction proceeds from room temperature to under heating.

Step 8

In Step 8, the succinic acid derivative (II''a) obtained in Step 7 is subjected to decarboxylation to give a succinic acid derivative (II''b) which is a monocarboxylic acid. The solvent may be a hydrocarbon solvent such as n-hexane, benzene, toluene and the like. The reaction is carried out in the presence of a tertiary amine, such as N-methylmorpholine, triethylamine and the like, at room temperature or under heating.

Step 9

In Step 9, the succinic acid derivative (II''a) obtained in Step 7 is reacted with formaldehyde in the presence of a secondary amine to give succinic acid derivative (II''c) which is α-exomethylenecarboxylic acid. Examples of the secondary amine include piperidine, diethylamine, morpholine and the like. The reaction is carried out in an alcohol solvent, such as methanol and ethanol and the like, or an amide solvent, such as DMF and the like, from room temperature to under heating.

Step 10

In Step 10, succinic acid derivative (II''c) obtained in Step 9 is reacted with arylthiol, heteroarylthiol, alkylthiol or arylalkylthiol as a nucleophilic reagent to give succinic acid derivative (II'd), wherein the substituent $R^1$ is arylthioalkyl, heteroarylthioalkyl, alkylthioalkyl or arylalkylthioalkyl. This reaction is carried out without solvent or in a halogenated hydrocarbon solvent, such as methylene chloride and the like, an alcohol solvent, such as methanol and the like, or in an amide solvent, such as DMF and the like, from room temperature to under heating.

The amino derivative (IV) and amino derivative (V), which are the starting compounds in schemes 1–3, can be produced by the method shown in the following Scheme 4.

Scheme 4

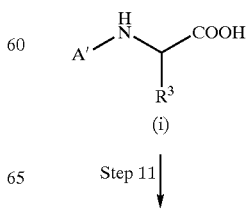

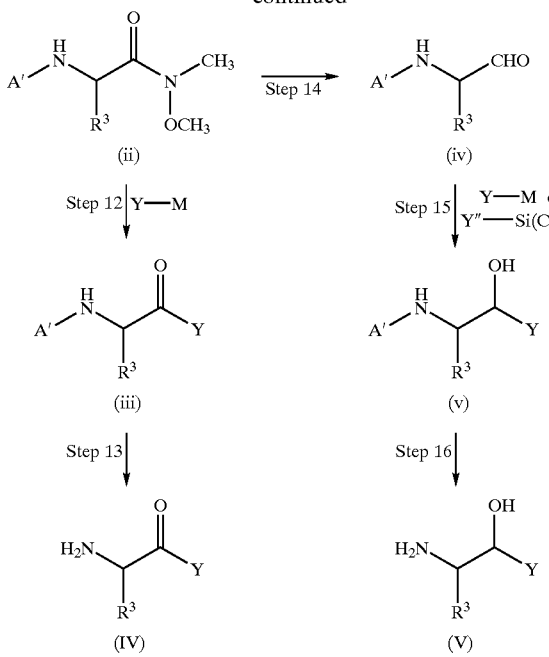

wherein A' is an amino-protecting group such as tert-butoxycarbonyl, benzyloxycarbonyl and the like, M is lithium or —MgP¹ wherein P¹ is halogen such as bromine, chlorine and the like, Y" is 2-thiazolyl or 2-oxazolyl optionally substituted with lower alkyl or phenyl, and R³ and Y are as defined above.

Step 11

In Step 11, compound (i) and O,N-dimethylhydroxylamine hydrochloride are reacted in an inert solvent in the presence of a condensing agent and a base to give compound (ii). This step can be performed by the general method described in Jean-Alain Fehrentz et al., Synthesis (1983) p. 676–678.

Step 12

In Step 12, compound (ii) is reacted with an organometallic compound Y—M to give compound (iii). The inert solvent to be used is preferably an aliphatic hydrocarbon solvent, such as hexane, cyclohexane and the like, ether solvent, such as diethyl ether, tetrahydrofuran and the like, and the like.

The reaction temperature is generally from −78° C. to 80° C., preferably from −78° C. to 40° C. The reaction time varies depending on the starting compound, solvent, reaction temperature and the like to be employed. It is generally 15 minutes–24 hours, preferably 15 minutes–10 hours.

Step 13

In Step 13, the amino-protecting group of compound (iii) is removed to give amino derivative (IV).

When the protecting group A' is tert-butoxycarbonyl, the protecting group can be removed under acidic conditions using, for example, trifluoroacetic acid, hydrogen chloride-containing dioxane, hydrogen chloride-containing methanol, hydrogen bromide-containing acetic acid and the like. The inert solvent to be used is preferably a halogenated hydrocarbon solvent, such as methylene chloride, chloroform and the like, an ether solvent, such as diethyl ether, tetrahydrofuran, dioxane and the like, an alcohol solvent, such as methanol, ethanol, n-propyl alcohol, isopropyl alcohol and the like, an organic acid, such as acetic acid and the like.

The reaction temperature is generally from 0° C. to 100° C., preferably from 0° C. to 50° C. The reaction time is generally 15 minutes–12 hours, preferably 15 minutes–4 hours.

When the protecting group A' is benzyloxycarbonyl, it is preferably removed by treating with an acid or by catalytic reduction.

The acid to be used for removal with an acid is preferably trifluoromethanesulfonic acid. The solvent to be used is preferably methylene chloride. The reaction temperature is preferably from 0° C. to 50° C. and the reaction time is preferably 5 minutes–6 hours.

The catalyst to be used for the method based on catalytic reduction is preferably palladium carbon and palladium black. The solvent to be used is preferably an alcohol solvent, such as methanol, ethanol, n-propyl alcohol, isopropyl alcohol and the like, an ether solvent, such as diethyl ether, tetrahydrofuran, 1,4-dioxane and the like, or an ester solvent, such as ethyl acetate and the like. The hydrogen pressure is generally 1–10 atm, and the reaction temperature is preferably from 0° C. to 100° C. and the reaction time is preferably 5 minutes–24 hours.

Step 14

In Step 14, compound (ii) is reduced with a reducing agent, such as lithium aluminum hydride and the like, in an inert solvent to give compound (iv). This step is performed according to the general method described in the above-mentioned Jean-Alain Fehrentz et al., Synthesis (1983) p. 676–678.

Step 15

In Step 15, (a) compound (iv) is reacted with an organometallic compound Y—M in an inert solvent, or (b) compound (iv) is reacted with trimethylsilyl derivative [Y"—Si(CH₃)₃] wherein Y" is 2-thiazolyl or 2-oxazolyl optionally substituted by lower alkyl or phenyl, in an inert solvent to give compound (v).

When compound (v) is produced by Step (a), the method is similar to that used in Step 12.

When compound (v) is produced by Step (b), 2-trimethylsilylthiazole optionally substituted by lower alkyl or phenyl, which is a trimethylsilyl derivative, can be prepared by the method described in Alessandro Dondoni et al., J. Org. Chem. (1988) 53 p. 1748–1761. The 2-trimethylsilyloxazole optionally substituted by lower alkyl or phenyl can be prepared by the method described in Alessandro Dondoni et al., J. Org. Chem. (1987) 52 p. 3413–3420.

When 2-trimethylsilylthiazole optionally substituted by lower alkyl or phenyl is used, the reaction is preferably carried out without solvent or in methylene chloride. The reaction temperature is generally from −40° C. to 80° C., preferably from −20° C. to 40° C. While the reaction time varies depending on the starting compound, solvent and reaction temperature to be employed, it is generally 1–48 hours, preferably 1–24 hours.

After the reaction without solvent, the reaction mixture is diluted with THF, and the compound is reacted with tetrabutylammonium fluoride at room temperature for 1–2 hours and post-treated by a conventional method to give the objective compound. When a solvent is used, the solvent is evaporated after the reaction and the above step is followed to give the objective compound.

When 2-trimethylsilyloxazole optionally substituted by lower alkyl or phenyl is used, the reaction is preferably carried out without solvent or in benzene, toluene or xylene. The reaction temperature is generally from 0° C. to 150° C., preferably from 20° C. to 100° C. While the reaction time varies depending on the starting compound, solvent, reaction temperature and the like to be employed, it is generally 1–80 hours, preferably 1–50 hours.

After the reaction, the objective compound can be obtained in the same manner as for 2-trimethylsilylthiazole. Alternatively, the compound is reacted with 1–2N hydrochloric acid instead of tetrabutylammonium fluoride for 0.5–2 hours and post-treated by a conventional method to give the objective compound.

Step 16

In Step 16, the amino-protecting group of compound (v) is removed to give an amino derivative (V), which step can be performed by the method similar to that in Step 13.

The compound (iii) and compound (iv) in Scheme 4 can be also produced by the method shown in the following Scheme 5.

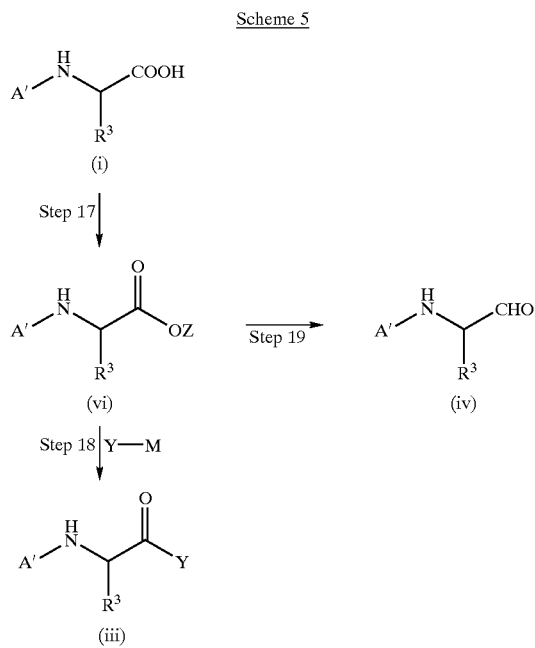

wherein Z is lower alkyl, such as methyl, ethyl and the like, or arylalkyl, such as benzyl and the like, and A', M, $R^3$ and Y are as defined above.

Step 17

In Step 17, compound (i) is reacted with alcohol ZOH in the presence of a condensing agent to give compound (vi). The inert solvent to be used is exemplified by a halogenated hydrocarbon solvent, such as methylene chloride, chloroform and the like, an ester solvent, such as ethyl acetate and the like, and an ether solvent, such as diethyl ether, tetrahydrofuran, 1,4-dioxane and the like, with preference given to methylene chloride and tetrahydrofuran.

As the condensing agent, it is preferably DCC, 1-(3-dimethylaminopropyl)-3-ethylcarbodiimide, diphenylphosphoryl azide and the like.

An acid-eliminating agent may be concurrently used in this reaction. The acid-eliminating agent to be used is preferably an organic amine such as triethylamine, diisopropylethylamine, N-methylmorpholine, pyridine, 4-dimethylaminopyridine, 4-pyrrolidinopyridine, proton sponge and the like.

The reaction temperature is generally from 0° C. to 80° C., preferably from 0° C. to 40° C. While the reaction time varies depending on the starting compound, solvent, reaction temperature and the like to be employed, it is generally 1–48 hours, preferably 1–12 hours.

Step 18

In Step 18, compound (vi) is reacted with an organometallic compound Y—M to give compound (iii), wherein the method similar to that in Step 12 can be employed.

Step 19

In Step 19, compound (vi) is reduced with a reducing agent, such as diisobutylaluminum hydride and the like, to give compound (iv). This step can be performed by the method described in Daniel H. Rich et al., J. Org. Chem. (1978) 43 p. 3624–3626.

The organometallic compound Y—M to be used in the above-mentioned reaction can be prepared by reacting a compound of the formula: Y—U, wherein U is hydrogen or halogen and Y is as defined above, with alkyllithium, aryllithium or Grignard reagent in an inert solvent.

Examples of the alkyl lithium to be used include ethyllithium, n-butyllithium, sec-butyllithium, tert-butyllithium and the like. Examples of aryllithium include phenyllithium and the like and examples of Grignard reagent include methylmagnesium bromide and the like. The solvent, reaction temperature and reaction time to be employed are the same as those in Step 12.

The compound (i), which is a starting compound in Schemes 4 and 5, can be prepared by the following method.

The compound (i) can be produced by protecting amino of an amino acid of the formula

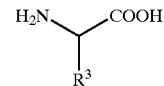

with an amino-protecting group such as tert-butoxycarbonyl, benzyloxycarbonyl and the like (see Pepuchidogousei no kiso to jikken, Izumiya et al., Maruzen Shoten, p. 16).

Any variation in various kinds of substituents, inclusive of $R^3$, and the like is not necessarily applicable only to a specific step, but rather, the step is free of limitation as long as it is performed under conditions that do not influence other functional groups present in chemical formula.

The hydroxamic acid derivative of the present invention thus synthesized can be collected at an optional purity by a known separation and purification method, such as condensation, extraction, chromatography, reprecipitation, recrystallization and the like, which are used as appropriate.

A pharmacologically acceptable salt and solvate of the hydroxamic acid derivative can be produced by a known method. Moreover, various isomers and the like of the hydroxamic acid derivative can be produced by a known method.

The hydroxamic acid derivative and a pharmacologically acceptable salt thereof of the present invention are superior in inhibitory activity of TNF α production in mammals (e.g., human, dog, cat and the like), and low in toxicity.

Therefore, the hydroxamic acid derivative and a pharmacologically acceptable salt thereof of the present invention are useful as an inhibitor of TNF α production and can be used effectively for the prophylaxis and treatment of the diseases such as autoimmune diseases and inflammatory diseases (e.g., sepsis, MOF, rheumatoid arthritis, Crohn's disease, cachexia, myasthenia gravis, systemic lupus erythematosus, asthma, I type diabetes, psoriasis and the like), and the like.

When the hydroxamic acid derivative or a pharmacologically acceptable salt thereof of the present invention is used as a pharmaceutical product, a pharmacologically acceptable carrier and the like are used to give a pharmaceutical composition in the form of granules, tablets, capsules, injections, ointment, eye drop, nose drop, cream, aerosol and the like, which can be administered orally or parenterally. Particularly, since the hydroxamic acid derivative and a pharmacologically acceptable salt thereof are superior in water-soluble property, they are preferably used for producing a water-soluble pharmaceutical composition such as injection, eye drop, nasal drop, infusion and the like.

The above-mentioned preparations contain an effective amount of the hydroxamic acid derivative or a pharmacologically acceptable salt thereof.

While the dose of the hydroxamic acid derivative and a pharmacologically acceptable salt thereof varies depending on the administration route, the disease state, body weight and age of patient, and the like, it can be determined as appropriate according to the object of administration. In general, when they are orally administered to an adult, the dose is 0.01–1,000 mg/kg body weight/day, preferably 0.05–250 mg/kg body weight/day, which is preferably administered once or several times a day.

EXAMPLES

While the present invention is explained in more detail in the following by referring to examples, the present invention is not limited by them.

$^1$H-NMR was measured at 300 or 500 MHz. The chemical shift of $^1$H-NMR was measured using tetramethylsilane as an internal standard, and the relative delta (δ) value was expressed in parts per million (ppm). The coupling constants were expressed in obvious multiplicity by hertz (Hz), and in s (singlet), d (doublet), t (triplet), q (quartet), m (multiplet), dd (doublet of doublets), br s (broad singlet) and the like.

Example 1

5-Methyl-3(R)-[1(S)-[4-[2-[1-(4-methyl)piperazinyl]ethoxy]benzoyl]-2-phenyl]ethylcarbamoyl-2(R or S)-phthalimidomethylhexanohydroxamic Acid Dihydrochloride

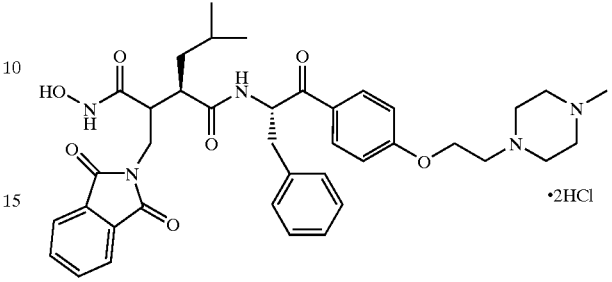

(1) 1-(2-Hydroxyethyl)-4-methylpiperazine

A mixture of 1-(2-hydroxyethyl)piperazine (10.0 g, 76.8 mmol), 37% aqueous formaldehyde solution (11.5 ml, 154 mmol), 10% palladium carbon catalyst (1.0 g) and methanol (100 ml) was stirred for 13 hr at room temperature in a hydrogen atmosphere. The reaction mixture was filtrated and the filtrate was concentrated. To the obtained residue was added 2N hydrochloric acid, and the mixture was washed with diethyl ether (200 ml). Sodium hydroxide (16 g) was added to the aqueous layer to make the layer alkaline, and the mixture was extracted with chloroform (4×200 ml). The organic layer was dried over anhydrous sodium sulfate and concentrated to give the title compound (9.3 g, 84%) as a pale-yellow liquid.

$^1$H-NMR (300 MHz, CDCl$_3$) δ 3.61 (t, J=5.4 Hz, 2H), 2.90–2.30 (m, 8H), 2.55 (t, J=5.4 Hz, 2H), 2.29 (s, 3H).

(2) O-Benzyl-4-bromophenol

To a solution of 4-bromophenol (20.0 g, 116 mmol) dissolved in DMF (100 ml) were added successively benzyl bromide (13.7 ml, 116 mmol), potassium carbonate (47.9 g, 347 mmol) and sodium iodide (1.7 g, 11.6 mmol), and the mixture was stirred for 4 hr at room temperature. Insoluble material was filtered off and water (500 ml) was added to the obtained filtrate. The precipitate was collected by filtration and the obtained precipitate was dissolved in diethyl ether (300 ml). The mixture was washed with water (100 ml) and saturated brine (100 ml). The organic layer was dried over anhydrous magnesium sulfate and concentrated. The obtained residue was washed with cold hexane and dried to give the title compound (26.2 g, 86%) as a white solid.

$^1$H-NMR (300 MHz, CDCl$_3$) δ 7.37 (d, J=8.9 Hz, 2H), 7.50–7.30 (m, 5H), 6.84 (d, J=8.9 Hz, 2H), 5.02 (s, 2H).

(3) 1-(4-Benzyloxy)phenyl-2(S)-(tert-butoxycarbonyl)amino-3-phenyl-1-propanone

The title compound (14.69 g, 55.8 mmol) of Example 1(2) was dissolved in tetrahydrofuran (THF, 200 ml). To the solution was added dropwise n-butyllithium (1.57M hexane solution, 35.6 ml, 55.8 mmol) at −70° C. for 10 min and the mixture was stirred for 1 hr at −70° C. to −65° C. Then, a solution of N$^a$-(tert-butoxycarbonyl)-L-phenylalanine N-methoxy-N-methylamide (5.74 g, 18.6 mmol) prepared according to the method of Jean-Alain Fehrentz et al. [Synthesis (1983) 676–678] and dissolved in THF (50 ml) was added dropwise at −70° C. over 5 min and the mixture was stirred for 30 min at −70° C. to −65° C. A saturated aqueous ammonium chloride solution (50 ml) was added to the reaction mixture under ice-cooling, and the mixture was concentrated. A saturated aqueous ammonium chloride solution (50 ml) was added to the obtained residue and the mixture was extracted with ethyl acetate (2×200 ml). The organic layer was washed with saturated brine (100 ml), dried over anhydrous magnesium sulfate and concentrated. The residue was purified by silica gel column chromatography (10:1 hexane-ethyl acetate) and recrystallized from ethyl acetate-hexane to give the title compound (4.42 g, 55%) as a white solid.

$^1$H-NMR (300 MHz, CDCl$_3$) δ 7.92 (d, J=8.9 Hz, 2H), 7.50–6.95 (m, 10H), 7.01 (d, J=8.9 Hz, 2H), 5.55–5.35 (m, 2H), 5.14 (s, 2H), 3.22 (dd, J=13.7, 5.7 Hz, 1H), 2.96 (dd, J=13.7, 5.6 Hz, 1H), 1.42 (s, 9H).

(4) 2(S)-Amino-1-(4-benzyloxy)phenyl-3-phenyl-1-propanone Trifluoroacetate

The title compound (4.30 g, 9.97 mmol) of Example 1(3) was dissolved in methylene chloride (20 ml). Thereto was added trifluoroacetic acid (20 ml) under ice-cooling and the mixture was stirred for 30 min at the same temperature. The reaction mixture was concentrated and crystallized from diethyl ether to give the title compound (3.64 g, 82%) as a white solid.

$^1$H-NMR (300 MHz, CDCl$_3$) δ 7.78 (d, J=8.9 Hz, 2H), 7.50–7.05 (m, 10H), 6.95 (d, J=8.9 Hz, 2H), 5.27 (t, J=6.1 Hz, 1H), 5.10 (s, 2H), 3.32 (dd, J=14.4, 6.2 Hz, 1H), 3.25 (dd, J=14.4, 6.2 Hz, 1H).

(5) tert-Butyl 3(R)-[1(S)-(4-Benzyloxy)benzoyl-2-phenyl]ethylcarbamoyl-5-methyl-2(R or S)-phthalimidomethylhexanoate The title compound (3.60 g, 8.08 mmol) of Example 1(4), 4-tert-butoxy-2(R)-isobutyl-3(R or S)-phthalimidomethylsuccinic acid (3.15 g, 8.08 mmol) prepared according to the method described in JP-A-4-352757 and JP-A-7-157470, 1-hydroxybenzotriazole monohydrate (HOBt-H$_2$O) (1.24 g, 8.08 mmol) and N-methylmorpholine (2.70 ml, 24.2 mmol) were dissolved in DMF (80 ml) and BOP reagent (5.36 g, 12.1 mmol) was added under ice-cooling, which was followed by stirring at room temperature for 6 hr. Water (300 ml) was added to the reaction mixture, and the mixture was extracted with ethyl acetate (2×200 ml). The organic layer was washed successively with 1N hydrochloric acid (100 ml), water (100 ml), saturated aqueous sodium hydrogencarbonate solution (2×100 ml) and saturated brine (100 ml), dried over anhydrous magnesium sulfate and concentrated. The obtained residue was purified by silica gel column chromatography (2:1 hexane-ethyl acetate) to give the title compound (5.35 g, 94%) as an amorphous powder.

$^1$H-NMR (300 MHz, CDCl$_3$) δ 7.99 (d, J=8.9 Hz, 2H), 7.90–7.80 (m, 2H), 7.78–7.65 (m, 2H), 7.48–7.30 (m, 5H), 7.23–7.10 (m, 4H), 7.10–7.03 (m, 1H), 7.01 (d, J=8.9 Hz, 2H), 6.93 (d, J=8.3 Hz, 1H), 6.00–5.90 (m, 1H), 5.14 (s, 2H), 3.49 (dd, J=14.0, 8.1 Hz, 1H), 3.38 (dd, J=14.0, 5.0 Hz, 1H), 3.28 (dd, J=14.1, 5.8 Hz, 1H), 3.02 (dd, J=14.1, 8.0 Hz, 1H), 3.00–2.88 (m, 1H), 2.68–2.55 (m, 1H), 1.75–1.60 (m, 1H), 1.50–1.30 (m, 1H), 1.26 (s, 9H), 1.12–0.98 (m, 1H), 0.80 (d, J=6.5 Hz, 3H), 0.76 (d, J=6.5 Hz, 3H).

(6) tert-Butyl 3(R)-[1(S)-(4-Hydroxy)benzoyl-2-phenyl]ethylcarbamoyl-5-methyl-2(R or S)-phthalimidomethylhexanoate A mixture of the title compound (5.00 g, 7.11 mmol) of Example 1(5), 10% palladium carbon catalyst (0.50 g) and ethanol (50 ml) was stirred for 28 hr at room temperature in a hydrogen atmosphere. The reaction mixture was filtrated and the filtrate was concentrated. The obtained residue was purified by silica gel column chromatography (10:1 chloroform-methanol) to give the title compound (3.12 g, 72%) as an amorphous solid.

$^1$H-NMR (300 MHz, CDCl$_3$) δ 8.50 (s, 1H), 7.90–7.65 (m, 6H), 7.30–7.00 (m, 6H), 6.89 (d, J=8.5 Hz, 2H), 6.00–5.80 (m, 1H), 3.50 (dd, J=14.1, 8.1 Hz, 1H), 3.42–3.25 (m, 2H), 3.05–2.85 (m, 2H), 2.73–2.60 (m, 1H), 1.75–1.60 (m, 1H), 1.50–1.30 (m, 1H), 1.28 (s, 9H), 1.17–1.00 (m, 1H), 0.84 (d, J=6.3 Hz, 3H), 0.76 (d, J=6.3 Hz, 3H).

(7) tert-Butyl 5-Methyl-3(R)-[1(S)-[4-[2-[1-(4-methyl)piperazinyl]ethoxy]benzoyl]-2-phenyl]ethylcarbamoyl-2(R or S)-phthalimidomethylhexanoate The title compound (200 mg, 0.33 mmol) of Example 1(6), the title compound (141 mg, 0.98 mmol) of Example 1(1) and triphenylphosphine (257 mg, 0.98 mmol) were dissolved in THF (5 ml). Diethyl azodicarboxylate (40% toluene solution, 426 mg, 0.98 mmol) was added to the solution under ice-cooling and the mixture was stirred for 4 hr at room temperature. The reaction mixture was concentrated and the obtained residue was purified by silica gel column chromatography (20:1 chloroform-methanol) to give the title compound (200 mg, 83%) as an amorphous solid.

$^1$H-NMR (300 MHz, CDCl$_3$) δ 7.97 (d, J=8.9 Hz, 2H), 7.90–7.78 (m, 2H), 7.78–7.65 (m, 2H), 7.22–7.12 (m, 4H), 7.12–7.00 (m, 1H), 7.00–6.80 (m, 1H), 6.94 (d, J=8.9 Hz, 2H), 6.00–5.90 (m, 1H), 4.17 (t, J=5.8 Hz, 2H), 3.55–3.45 (m, 1H), 3.45–3.35 (m, 1H), 3.35–3.20 (m, 1H), 3.10–2.90 (m, 2H), 2.84 (t, J=5.8 Hz, 2H), 2.75–2.35 (m, 9H), 2.30 (s, 3H), 1.73–1.60 (m, 1H), 1.35–1.26 (m, 1H), 1.26 (s, 9H), 1.12–1.00 (m, 1H), 0.81 (d, J=6.5 Hz, 3H), 0.76 (d, J=6.5 Hz, 3H).

(8) 5-Methyl-3(R)-[1(S)-[4-[2-[1-(4-methyl)piperazinyl]ethoxy]benzoyl]-2-phenyl]ethylcarbamoyl-2(R or S)-phthalimidomethylhexanoic Acid Ditrifluoroacetate The title compound (200 mg, 0.27 mmol) of Example 1(7) was dissolved in methylene chloride (10 ml) and trifluoroacetic acid (10 ml) was added under ice-cooling. The mixture was stirred for 2 hr at room temperature. The reaction mixture was concentrated to give the title compound (217 mg, 88%) as an amorphous solid.

$^1$H-NMR (300 MHz, DMSO-d$_6$) δ 8.70 (d, J=8.8 Hz, 1H), 8.03 (d, J=8.8 Hz, 2H), 7.95–7.82 (m, 4H), 7.35 (d, J=7.5 Hz, 2H), 7.12 (t, J=7.6 Hz, 2H), 7.05 (d, J=8.8 Hz, 2H), 6.85 (t, J=7.4 Hz, 1H), 5.75–5.60 (m, 1H), 4.20 (t, J=5.3 Hz, 2H), 3.20–3.00 (m, 5H), 3.00–2.85 (m, 3H), 2.85–2.60 (m, 4H), 2.78 (s, 3H), 2.60–2.40 (m, 2H), 2.40–2.25 (m, 1H), 1.50–1.35 (m, 1H), 1.10–0.95 (m, 1H), 0.90–0.75 (m, 1H), 0.68 (d, J=6.4 Hz, 3H), 0.61 (d, J=6.4 Hz, 3H).

(9) 2-Tetrahydropyranyl 5-Methyl-3(R)-[1(S)-[4-[2-[1-(4-methyl)piperazinyl]ethoxy]benzoyl]-2-phenyl]ethylcarbamoyl-2(R or S)-phthalimidomethylhexanohydroxamate The title compound (210 mg, 0.23 mmol) of Example 1(8), O-2-tetrahydropyranylhydroxylamine (33 mg, 0.28 mmol), HOBt-H$_2$O (36 mg, 0.23 mmol) and N-methylmorpholine (0.25 ml, 2.32 mmol) were dissolved in DMF (10 ml), and BOP reagent (154 mg, 0.35 mmol) was added under ice-cooling. The mixture was stirred for 13 hr at room temperature. Water (50 ml) was added and the mixture was extracted with ethyl acetate (2×50 ml). The organic layer was washed successively with saturated aqueous sodium hydrogencarbonate solution (2×50 ml) and saturated brine (50 ml), dried over anhydrous sodium sulfate and concentrated. The obtained residue was purified by silica gel column chromatography (20:1 chloroform-methanol) to give the title compound (120 mg, 66%) as a white solid.

$^1$H-NMR (300 MHz, DMSO-d$_6$) δ 10.95–10.80 (m, 1H), 8.72–8.60 (m, 1H), 8.00 (d, J=8.8 Hz, 2H), 7.95–7.75 (m,

4H), 7.35 (d, J=7.4 Hz, 2H), 7.09 (t, J=7.6 Hz, 2H), 7.02 (d, J=8.8 Hz, 2H), 6.81 (t, J=7.3 Hz, 1H), 5.70–5.55 (m, 1H), 4.55–4.30 (m, 1H), 4.11 (t, J=5.7 Hz, 2H), 3.70–3.55 (m, 1H), 3.18–3.05 (m, 1H), 3.05–2.95 (m, 1H), 2.95–2.80 (m, 1H), 2.80–2.55 (m, 1H), 2.64 (t, J=5.7 Hz, 2H), 2.55–2.20 (m, 10H), 2.20–2.05 (m, 1H), 2.14 (s, 3H), 1.60–1.20 (m, 7H), 1.05–0.90 (m, 1H), 0.80–0.70 (m, 1H), 0.64 (d, J=6.3 Hz, 3H), 0.60 (d, J=6.3 Hz, 3H).

(10) 5-Methyl-3(R)-[1(S)-[4-[2-[1-(4-methyl)piperazinyl]ethoxy]benzoyl]-2-phenyl]ethylcarbamoyl-2(R or S)-phthalimidomethylhexanohydroxamic Acid Dihydrochloride To a solution of the title compound (110 mg, 0.14 mmol) of Example 1(9), methylene chloride (10 ml) and methanol (10 ml) was added 1.3N hydrogen chloride-methanol reagent (1 ml) under ice-cooling, and the mixture was stirred for 2 hr at room temperature. Diethyl ether was added to the reaction mixture to precipitate a solid to give the title compound (69 mg, 62%) as a white solid.

$^1$H-NMR (500 MHz, DMSO-d$_6$) δ 10.31 (br s, 1H), 8.63 (d, J=8.6 Hz, 1H), 8.04 (d, J=8.7 Hz, 2H), 7.90–7.80 (m, 4H), 7.35 (d, J=7.3 Hz, 2H), 7.10–7.05 (m, 4H), 6.79 (t, J=7.4 Hz, 1H), 5.70–5.60 (m, 1H), 4.50–4.20 (br, 2H), 3.65–3.15 (m, 11H), 3.11 (dd, J=14.0, 4.5 Hz, 1H), 2.86 (dd, J=14.0, 10.7 Hz, 1H), 2.81 (s, 3H), 2.50–2.40 (m, 2H), 2.25–2.15 (m, 1H), 1.41–1.32 (m, 1H), 1.08–0.97 (m, 1H), 0.82–0.75 (m, 1H), 0.68 (d, J=6.5 Hz, 3H), 0.62 (d, J=6.5 Hz, 3H).

Example 2

3(R)-[1(S)-[4-(2-Dimethylaminoethoxy)benzoyl]-2-phenyl]ethylcarbamoyl-5-methyl-2(R or S)-phthalimidomethylhexanohydroxamic Acid Hydrochloride

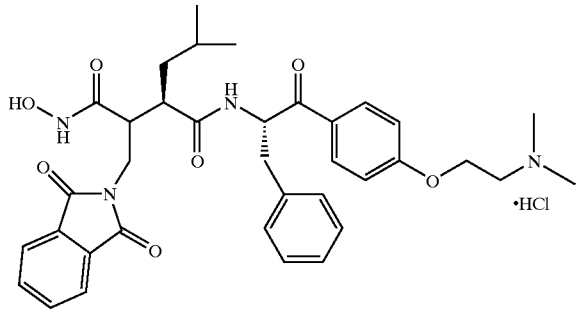

(1) N,N-Dimethyl-2-(4-bromophenoxy)ethylamine

4-Bromophenol (10.0 g, 57.8 mmol) and 2-dimethylaminoethyl chloride hydrochloride (8.33 g, 57.8 mmol) were dissolved in DMF (200 ml), and potassium carbonate (24.0 g, 173 mmol) and sodium iodide (0.87 g, 5.78 mmol) were added under ice-cooling. The mixture was stirred for 13 hr at room temperature and at 70° C. for 3 hr. Water (400 ml) was added to the reaction mixture and the mixture was extracted with chloroform (2×200 ml). The organic layer was washed successively with water (2×200 ml) and saturated brine (200 ml), dried over anhydrous magnesium sulfate and concentrated. The obtained residue was dissolved in 1N hydrochloric acid (100 ml) and washed with ethyl acetate (2×200 ml). Sodium hydroxide (4 g) was added to the aqueous layer to make the layer alkaline, and the mixture was extracted with chloroform (2×200 ml). The organic layer was dried over anhydrous magnesium sulfate and concentrated. Hexane was added to the obtained residue and insoluble matter was filtered off. The mother liquor was concentrated to give the title compound (5.25 g, 37%) as a transparent oil.

$^1$H-NMR (300 MHz, CDCl$_3$) δ 7.36 (d, J=8.9 Hz, 2H), 6.80 (d, J=8.9 Hz, 2H), 4.02 (t, J=5.7 Hz, 2H), 2.71 (t, J=5.7 Hz, 2H), 2.33 (s, 6H).

(2) 2(S)-(tert-Butoxycarbonyl)amino-1-[4-(2-dimethylaminoethoxy)phenyl]-3-phenyl-1-propanone According to the method of Example 1(3), the title compound of Example 2(1) and N$^α$-(tert-butoxycarbonyl)-L-phenylalanine N-methoxy-N-methylamide were reacted and the resulting product was purified by silica gel column chromatography (100:1 chloroform-methanol), followed by recrystallization from hexane, to give the title compound (yield 15%) as a white solid.

$^1$H-NMR (300 MHz, CDCl$_3$) δ 7.91 (d, J=8.8 Hz, 2H), 7.30–7.12 (m, 3H), 7.02 (d, J=7.4 Hz, 2H), 6.95 (d, J=8.8 Hz, 2H), 5.55–5.35 (m, 2H), 4.14 (t, J=5.7 Hz, 2H), 3.22 (dd, J=13.7, 5.7 Hz, 1H), 2.92 (dd, J=13.7, 5.5 Hz, 1H), 2.76 (t, J=5.7 Hz, 2H), 2.35 (s, 6H), 1.42 (s, 9H).

(3) 2(S)-Amino-1-[4-(2-dimethylaminoethoxy)phenyl]-3-phenyl-1-propanone Ditrifluoroacetate The title compound of Example 2(2) was treated in the same manner as in Example 1(4) to give the title compound quantitatively as a yellow viscous oil.

$^1$H-NMR (300 MHz, DMSO-d$_6$) δ 10.20–9.80 (br, 1H), 8.50–8.20 (br, 3H), 8.01 (d, J=8.9 Hz, 2H), 7.30–7.20 (m, 3H), 7.20–7.15 (m, 2H), 7.11 (d, J=8.9 Hz, 2H), 5.45–5.30 (m, 1H), 4.50–4.40 (m, 2H), 3.60–3.50 (m, 2H), 3.20–3.00 (m, 2H), 2.88 (s, 6H).

(4) tert-Butyl 3(R)-[1(S)-[4-(2-Dimethylaminoethoxy)benzoyl]-2-phenyl]ethylcarbamoyl-5-methyl-2(R or S)-phthalimidomethylhexanoate In the same manner as in Example 1(5), 4-tert-butoxy-2(R)-isobutyl-3(R or S)-phthalimidomethylsuccinic acid and the title compound of Example 2(3) were reacted and the resulting product was purified by silica gel column chromatography (50:1 chloroform-methanol) to give the title compound as an amorphous solid.

$^1$H-NMR (300 MHz, CDCl$_3$) δ 7.98 (d, J=8.9 Hz, 2H), 7.90–7.78 (m, 2H), 7.78–7.65 (m, 2H), 7.20–7.10 (m, 4H), 7.10–7.00 (m, 1H), 6.96 (d, J=8.9 Hz, 2H), 6.95–6.85 (m, 1H), 6.00–5.90 (m, 1H), 4.15 (t, J=5.6 Hz, 2H), 3.49 (dd, J=14.0, 8.1 Hz, 1H), 3.38 (dd, J=14.0, 5.0 Hz, 1H), 3.27 (dd, J=14.1, 5.8 Hz, 1H), 3.02 (dd, J=14.1, 7.9 Hz, 1H), 2.95–2.85 (m, 1H), 2.79 (t, J=5.6 Hz, 2H), 2.65–2.53 (m, 1H), 2.37 (s, 6H), 1.75–1.60 (m, 1H), 1.50–1.25 (m, 1H), 1.26 (s, 9H), 1.10–0.95 (m, 1H), 0.81 (d, J=6.6 Hz, 3H), 0.76 (d, J=6.6 Hz, 3H).

(5) 3(R)-[1(S)-[4-(2-Dimethylaminoethoxy)benzoyl]-2-phenyl]ethylcarbamoyl-5-methyl-2(R or S)-phthalimidomethylhexanoic Acid Trifluoroacetate The title compound of Example 2(4) was treated in the same manner as in Example 1(8) and the resulting product was crystallized from diethyl ether to give the title compound as a white solid at an overall yield from the title compound of Example 2(2) (3 steps) of 84%.

$^1$H-NMR (300 MHz, DMSO-d$_6$) δ 12.80–12.00 (br, 1H), 9.80–9.40 (br, 1H), 8.71 (d, J=8.7 Hz, 1H), 8.07 (d, J=8.9 Hz, 2H), 7.95–7.80 (m, 4H), 7.36 (d, J=7.2 Hz, 2H), 7.20–7.00 (m, 4H), 6.84 (t, J=7.4 Hz, 1H), 5.75–5.65 (m, 1H), 4.40 (t, J=4.8 Hz, 2H), 3.52 (t, J=4.8 Hz, 2H), 3.45–3.30 (m, 1H), 3.11 (dd, J=13.9, 4.3 Hz, 1H), 2.90–2.80 (m, 1H), 2.86 (s, 6H), 2.70–2.60 (m, 1H), 2.55–2.45 (m, 1H), 2.35 (dd, J=13.6, 5.1 Hz, 1H), 1.50–1.35 (m, 1H), 1.10–0.90 (m, 1H), 0.90–0.75 (m, 1H), 0.69 (d, J=6.5 Hz, 3H), 0.62 (d, J=6.5 Hz, 3H).

(6) 2-Tetrahydropyranyl 3(R)-[1(S)-[4-(2-Dimethylaminoethoxy)benzoyl]-2-phenyl]ethylcarbamoyl-5-methyl-2(R or S)-phthalimidomethylhexanohydroxamate In the same manner as in Example 1(9), the title compound of Example 2(5) and O-2-tetrahydropyranylhydroxylamine were reacted, and the product was purified by silica gel column chromatography (20:1 chloroform-methanol) and recrystallized from diethyl ether-hexane to give the title compound (yield 78%) as a white solid.

$^1$H-NMR (300 MHz, DMSO-d$_6$) δ 11.00–10.80 (m, 1H), 8.75–8.60 (m, 1H), 8.00 (d, J=8.8 Hz, 2H), 7.90–7.85 (m, 4H), 7.36 (d, J=7.4 Hz, 2H), 7.09 (t, J=7.5 Hz, 2H), 7.02 (d, J=8.8 Hz, 2H), 6.81 (t, J=7.3 Hz, 1H), 5.70–5.55 (m, 1H), 4.55–4.30 (m, 1H), 4.09 (t, J=5.5 Hz, 2H), 3.70–3.60 (m, 1H), 3.50–3.25 (m, 2H), 3.13 (dd, J=14.0, 4.1 Hz, 1H), 3.05–2.65 (m, 1H), 2.87 (dd, J=14.0, 10.8 Hz, 1H), 2.58 (t, J=5.5 Hz, 2H), 2.55–2.47 (m, 1H), 2.47–2.40 (m, 1H), 2.19 (s, 6H), 2.09 (dd, J=13.5, 4.1 Hz, 1H), 1.60–1.20 (m, 7H), 1.10–0.90 (m, 1H), 0.82–0.70 (m, 1H), 0.64 (d, J=6.6 Hz, 3H), 0.60 (d, J=6.6 Hz, 3H).

(7) 3(R)-[1(S)-[4-(2-Dimethylaminoethoxy)benzoyl]-2-phenyl]ethylcarbamoyl-5-methyl-2(R or S)-phthalimidomethylhexanohydroxamic Acid Hydrochloride The title compound of Example 2(6) was treated in the same manner as in Example 1(10) and the product was crystallized from diethyl ether to give the title compound (yield 86%) as a white solid.

$^1$H-NMR (500 MHz, DMSO-d$_6$) δ 10.33 (br s, 1H), 10.20–10.00 (br, 1H), 8.64 (d, J=8.6 Hz, 1H), 8.61 (br s, 1H), 8.07 (d, J=9.0 Hz, 2H), 8.00–7.82 (m, 4H), 7.36 (d, J=7.4 Hz, 2H), 7.11 (d, J=9.0 Hz, 2H), 7.08 (t, J=7.7 Hz, 2H), 6.78 (t, J=7.4 Hz, 1H), 5.71–5.63 (m, 1H), 4.45–4.35 (br t, 2H), 3.55–3.48 (br t, 2H), 3.48–3.40 (m, 1H), 3.09 (dd, J=14.0, 4.4 Hz, 1H), 2.90–2.85 (m, 1H), 2.84 (s, 6H), 2.49–2.42 (m, 2H), 2.20–2.13 (m, 1H), 1.40–1.30 (m, 1H), 1.08–0.95 (m, 1H), 0.81–0.73 (m, 1H), 0.67 (d, J=6.5 Hz, 3H), 0.62 (d, J=6.5 Hz, 3H).

Example 3

3(R)-[1(S)-(2-Furyl)carbonyl-2-(4-guanidinophenyl)]ethylcarbamoyl-5-methyl-2(R or S)-phthalimidomethylhexanohydroxamic Acid Hydrochloride

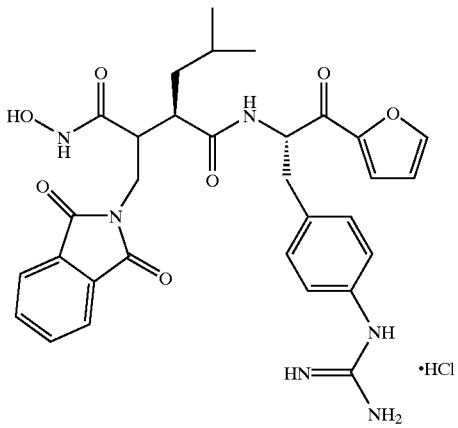

(1) N$^a$-(tert-Butoxycarbonyl)-L-(4-nitro)phenylalanine N-Methoxy-N-methylamide According to the method of Jean-Alain Fehrentz et al. [Synthesis (1983) 676–678], N-(tert-butoxycarbonyl)-L-(4-nitro)phenylalanine and N,O-dimethylhydroxyamine hydrochloride were reacted and the resulting product was purified by silica gel column chromatography (2:1 hexane-ethyl acetate) to give the title compound (yield 96%) as a yellow viscous liquid.

$^1$H-NMR (300 MHz, CDCl$_3$) δ 8.15 (d, J=8.6 Hz, 2H), 7.34 (d, J=8.6 Hz, 2H), 5.25 (br d, J=8.7 Hz, 1H), 5.05–4.85 (m, 1H), 3.73 (s, 3H), 3.25–3.10 (m, 1H), 3.19 (s, 3H), 2.97 (dd, J=13.5, 7.2 Hz, 1H), 1.38 (s, 9H).

(2) 2(S)-(tert-Butoxycarbonyl)amino-1-(2-furyl)-3-(4-nitro)phenyl-1-propanone

According to the method of Example 1(3), furan and the title compound of Example 3(1) were reacted and the resulting product was recrystallized from ethyl acetate-hexane to give the title compound (yield 59%) as a pale-yellow solid.

$^1$H-NMR (300 MHz, CDCl$_3$) δ 8.12 (d, J=8.6 Hz, 2H), 7.64 (d, J=1.6 Hz, 1H), 7.45–7.25 (m, 3H), 6.59 (dd, J=3.6, 1.6 Hz, 1H), 5.45–5.25 (m, 2H), 3.45–3.20 (m, 1H), 3.20–3.00 (m, 1H), 1.40 (s, 9H).

(3) 3-(4-Amino)phenyl-2(S)-(tert-butoxycarbonyl)amino-1-(2-furyl)-1-propanone

A mixture of the title compound (1.00 g, 2.78 mmol) of Example 3(2), 10% palladium carbon catalyst (0.10 g), ethanol (20 ml) and ethyl acetate (20.ml) was stirred for 3 hr at room temperature in a hydrogen atmosphere. The reaction mixture was filtered and the filtrate was concentrated to give the title compound (0.92 g, quantitatively) as an amorphous solid.

$^1$H-NMR (300 MHz, CDCl$_3$) δ 7.61 (d, J=1.2 Hz, 1H), 7.22 (d, J=3.5 Hz, 1H), 6.86 (d, J=8.1 Hz, 2H), 6.70–6.45 (m, 3H), 5.35–5.10 (m, 2H), 3.58 (br s, 2H), 3.10 (dd, J=13.9, 5.7 Hz, 1H), 2.93 (dd, J=13.9, 5.6 Hz, 1H), 1.41 (s, 9H).

(4) 2(S)-(tert-Butoxycarbonyl)amino-3-[4-(2,3-dibenzyloxycarbonylguanidino)phenyl]-1-(2-furyl)-1-propanone The title compound (0.92 g, 2.78 mmol) of Example 3(3) was dissolved in methylene chloride (30 ml). 1H-Pyrazole-1-(N,N'-dibenzyloxycarbonyl)carboxamidine (1.58 g, 4.16 mmol) was added under ice-cooling and the mixture was stirred for 65 hr at room temperature. The reaction mixture was concentrated and recrystallized from ethyl acetate-hexane to give the title compound (1.56 g, 88%) as a white solid.

$^1$H-NMR (300 MHz, CDCl$_3$) δ 11.88 (br s, 1H), 10.20 (br s, 1H), 7.60 (d, J=1.6 Hz, 1H), 7.55–7.25 (m, 10H), 7.46 (d, J=8.3 Hz, 2H), 7.24 (d, J=3.6 Hz, 1H), 7.05 (d, J=8.3 Hz, 2H), 6.53 (dd, J=3.6, 1.6 Hz, 1H), 5.35–5.20 (m, 2H), 5.23 (s, 2H), 5.14 (s, 2H), 3.30–3.10 (m, 1H), 3.10–2.95 (m, 1H), 1.41 (s, 9H).

(5) 2(S)-Amino-3-[4-(2,3-dibenzyloxycarbonylguanidino)phenyl]-1-(2-furyl)-1-propanone Trifluoroacetate The title compound of Example 3(4) was treated in the same manner as in Example 1(4) and the product was crystallized from diethyl ether to give the title compound (yield 89%) as a white solid.

$^1$H-NMR (300 MHz, DMSO-d$_6$) δ 11.40–11.20 (br, 1H), 9.95 (s, 1H), 8.50–8.10 (br, 3H), 8.08 (d, J=1.7 Hz, 1H), 7.65 (d, J=3.7 Hz, 1H), 7.55–7.25 (m, 10H), 7.48 (d, J=8.5 Hz, 2H), 7.16 (d, J=8.5 Hz, 2H), 6.75 (dd, J=3.7, 1.7 Hz, 1H), 5.25 (s, 2H), 5.04 (s, 2H), 4.96 (t, J=6.7 Hz, 1H), 3.20–3.00 (m, 2H).

(6) tert-Butyl 3(R)-[2-[4-(2,3-Dibenzyloxycarbonylguanidino)phenyl]-1(S)-(2-furyl)carbonyl]ethylcarbamoyl-5-methyl-2(R or S)-phthalimidomethylhexanoate In the same manner as in Example 1(5), 4-tert-butoxy-2 (R)-isobutyl-3(R or S)-phthalimidomethylsuccinic acid and the title compound of Example 3(5) were reacted and the product was purified by silica gel column chromatography (1:1 hexane-ethyl acetate) to give the title compound (yield 82%) as an amorphous solid.

$^1$H-NMR (300 MHz, CDCl$_3$) δ 11.60 (s, 1H), 10.07 (s, 1H), 7.75–7.65 (m, 2H), 7.63 (d, J=1.7 Hz, 1H), 7.59–7.51 (m, 2H), 7.48 (d, J=8.5 Hz, 2H), 7.45–7.25 (m, 11H), 7.21 (d, J=8.5 Hz, 2H), 6.71 (d, J=8.7 Hz, 1H), 6.55 (dd, J=3.6, 1.7 Hz, 1H), 5.82–5.70 (m, 1H), 5.19 (s, 2H), 5.10 (s, 2H), 3.45 (dd, J=13.9, 8.8 Hz, 1H), 3.29 (dd, J=14.1, 5.7 Hz, 1H), 3.14 (dd, J=13.9, 4.8 Hz, 1H), 2.96 (dd, J=14.1, 9.0 Hz, 1H), 2.95–2.83 (m, 1H), 2.55 (ddd, J=10.2, 10.2, 2.9 Hz, 1H), 1.75–1.60 (m, 1H), 1.50–1.30 (m, 1H), 1.24 (s, 9H), 1.10–0.95 (m, 1H), 0.84 (d, J=6.5 Hz, 3H), 0.78 (d, J=6.5 Hz, 3H).

(7) 3(R)-[2-[4-(2,3-Dibenzyloxycarbonylguanidino) phenyl]-1(S)-(2-furyl)carbonyl]ethylcarbamoyl-5-methyl-2(R or S)-phthalimidomethylhexanoic Acid The title compound of Example 3(6) was treated in the same manner as in Example 1(8) and the product was crystallized from diethyl ether to give the title compound (yield 79%) as a white solid.

$^1$H-NMR (300 MHz, DMSO-d$_6$) δ 12.40–12.10 (br, 1H), 10.95 (s, 1H), 9.81 (s, 1H), 8.68 (d, J=8.9 Hz, 1H), 8.08 (d, J=1.7 Hz, 1H), 7.79 (d, J=3.6 Hz, 1H), 7.66–7.58 (m, 2H), 7.57–7.30 (m, 16H), 6.77 (dd, J=3.6, 1.7 Hz, 1H), 5.63–5.50 (m, 1H), 5.21 (s, 2H), 5.04 (s, 2H), 3.50–3.25 (m, 1H), 3.20–3.05 (m, 1H), 2.88–2.70 (m, 1H), 2.60–2.40 (m, 2H), 1.90–1.78 (m, 1H), 1.50–1.35 (m, 1H), 1.20–1.05 (m, 1H), 0.87–0.75 (m, 1H), 0.75 (d, J=6.5 Hz, 3H), 0.66 (d, J=6.5 Hz, 3H).

(8) 2-Tetrahydropyranyl 3(R)-[2-[4-(2,3-Dibenzyloxycarbonylguanidino)phenyl]-1(S)-(2-furyl) carbonyl]ethylcarbamoyl-5-methyl-2(R or S)-phthalimidomethylhexanohydroxamate In the same manner as in Example 1(9), the title compound of Example 3(7) and O-2-tetrahydropyranylhydroxylamine were reacted, and water (50 ml)-diethyl ether (50 ml) was added to the reaction mixture under ice-cooling. The precipitated solid was collected by filtration, washed successively with water, saturated aqueous sodium hydrogencarbonate solution, water and diethyl ether, and dried to give the title compound (yield 75%) as a white solid.

$^1$H-NMR (300 MHz, DMSO-d$_6$) δ 11.00–10.75 (m, 2H), 9.90–9.65 (br, 1H), 8.64 (d, J=8.6 Hz, 1H), 8.10–8.00 (m, 1H), 7.90–7.20 (m, 19H), 6.80–6.70 (m, 1H), 5.60–5.40 (m, 1H), 5.30–4.85 (m, 4H), 4.55–4.30 (m, 1H), 3.70–2.90 (m, 3H), 2.90–2.70 (m, 1H), 2.70–2.25 (m, 3H), 1.90–1.60 (m, 1H), 1.60–1.18 (m, 7H), 1.18–1.00 (m, 1H), 0.90–0.75 (m, 1H), 0.73 (d, J=6.3 Hz, 3H), 0.65 (d, J=6.3 Hz, 3H).

(9) 2-Tetrahydropyranyl 3(R)-[1(S)-(2-Furyl)carbonyl-2-(4-guanidino)phenyl]ethylcarbamoyl-5-methyl-2(R or S)-phthalimidomethylhexanohydroxamate Acetate A mixture of the title compound (395 mg, 0.41 mmol) of Example 3(8), 10% palladium carbon catalyst (40 mg), methanol (20 ml), methylene chloride (20 ml) and acetic acid (1 ml) was stirred for 26 hr at room temperature in a hydrogen atmosphere. The reaction mixture was filtrated and the filtrate was concentrated. The obtained residue was recrystallized from ethyl acetate-diethyl ether to give the title compound (294 mg, 95%) as a white solid.

$^1$H-NMR (300 MHz, DMSO-d$_6$) δ 11.10–10.90 (br, 1H), 8.78 (d, J=8.3 Hz, 1H), 8.02 (d, J=1.6 Hz, 1H), 7.90–7.80 (m, 4H), 7.56 (d, J=3.6 Hz, 1H), 7.50–7.10 (br, 4H), 7.34 (d, J=8.3 Hz, 2H), 6.96 (d, J=8.3 Hz, 2H), 6.73 (dd, J=3.6, 1.6 Hz, 1H), 5.40–5.23 (m, 1H), 4.60–4.35 (m, 1H), 3.80–2.45 (m, 8H), 1.74 (s, 3H), 1.60–1.10 (m, 8H), 0.93–0.80 (m, 1H), 0.76 (d, J=6.3 Hz, 3H), 0.68 (d, J=6.3 Hz, 3H).

(10) 3(R)-[1(S)-(2-Furyl)carbonyl-2-(4-guanidinophenyl)] ethylcarbamoyl-5-methyl-2(R or S)-phthalimidomethylhexanohydroxamic Acid Hydrochloride The title compound of Example 3(9) was treated in the same manner as in Example 1(10) and the product was crystallized from diethyl ether to give the title compound (yield 90%) as a white solid.

$^1$H-NMR (500 MHz, DMSO-d$_6$) δ 10.42 (br s, 1H), 9.38 (br s, 1H), 8.78 (d, J=8.1 Hz, 1H), 8.75–8.60 (br, 1H), 8.01 (d, J=1.7 Hz, 1H), 7.90–7.80 (m, 4H), 7.55 (d, J=3.6 Hz, 1H), 7.40 (d, J=8.4 Hz, 2H), 7.09 (br s, 4H), 7.03 (d, J=8.4 Hz, 2H), 6.73 (dd, J=3.6, 1.7 Hz, 1H), 5.35–5.28 (m, 1H), 3.90–3.60 (m, 1H), 3.12 (dd, J=14.0, 5.4 Hz, 1H), 2.93 (dd, J=14.0, 9.4 Hz, 1H), 2.75 (dd, J=13.5, 3.8 Hz, 1H), 2.62–2.55 (m, 1H), 1.47–1.32 (m, 1H), 1.25–1.12 (m, 1H), 0.92–0.83 (m, 1H), 0.76 (d, J=6.5 Hz, 3H), 0.69 (d, J=6.5 Hz, 3H).

Example 4

3(R)-[1(S)-[2-[5-(2-Dimethylaminoethoxy)methyl] furyl]-carbonyl-2-phenyl]ethylcarbamoyl-5-methyl-2 (R or S)-phthalimidomethylhexanohydroxamic Acid Hydrochloride

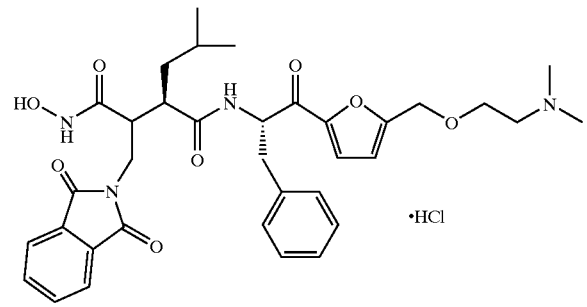

(1) 2-[(2-Dimethylaminoethoxy)methyl]furan

Furfuryl alcohol (10.0 g, 102 mmol) was dissolved in DMF (200 ml) and sodium hydride (60% dispersion in oil, 9.00 g, 225 mmol) was added under ice-cooling. The mixture was stirred for 15 min at the same temperature. Then, 2-dimethylaminoethyl chloride hydrochloride (15.4 g, 107 mmol) was added under ice-cooling and the mixture was stirred at the same temperature for 30 min and at room temperature for 3.5 hr. Water (200 ml) was added to the reaction mixture under ice-cooling and the mixture was extracted with diethyl ether (2×500 ml). The organic layer was dried over anhydrous sodium sulfate and concentrated. The obtained residue was purified by silica gel column chromatography (20:1 chloroform-methanol) to give the title compound (4.19 g, 24%) as a red-brown liquid.

$^1$H-NMR (300 MHz, CDCl$_3$) δ 7.45–7.35 (m, 1H), 6.40–6.30 (m, 2H), 4.48 (s, 2H), 3.56 (t, J=5.8 Hz, 2H), 2.51 (t, J=5.8 Hz, 2H), 2.25 (s, 6H).

(2) 2(S)-(tert-Butoxycarbonyl)amino-1-[2-[5-(2-dimethylaminoethoxy)methyl]furyl]-3-phenyl-1-propanone Diisopropylamine (3.65 ml, 26.1 mmol) was dissolved in THF (50 ml) and n-butyllithium (1.57M hexane solution, 16.6 ml, 26.1 mmol) was added dropwise under ice-cooling. The mixture was stirred for 30 min at the same temperature. Then, a solution of the title compound (4.19 g, 24.8 mmol)

of Example 4(1) dissolved in THF (25 ml) was added dropwise at −78° C. and the mixture was stirred for 40 min at the same temperature. A solution of N$^\alpha$-(tert-butoxycarbonyl)-L-phenylalanine N-methoxy-N-methylamide (2.55 g, 8.27 mmol) dissolved in THF (25 ml) was added dropwise at −78° C. and the mixture was stirred for 3 hr at the same temperature. A 5% aqueous citric acid solution (50 ml) was added and THF was evaporated under reduced pressure. The obtained residue was extracted with ethyl acetate (3×100 ml). The organic layer was washed with saturated aqueous sodium hydrogencarbonate solution (2×100 ml) and saturated brine (100 ml), dried over anhydrous sodium sulfate and concentrated. The obtained residue was purified by silica gel column chromatography (20:1 chloroform-methanol) to give the title compound (280 mg, 8%) as a red-brown liquid.

$^1$H-NMR (300 MHz, CDCl$_3$) δ 7.35–7.05 (m, 6H), 6.45 (d, J=3.5 Hz, 1H), 5.40–5.20 (m, 2H), 4.52 (s, 2H), 3.70–3.50 (m, 2H), 3.18 (dd, J=13.2, 5.9 Hz, 1H), 3.02 (dd, J=13.2, 5.7 Hz, 1H), 2.60–2.45 (m, 2H), 2.25 (s, 6H), 1.41 (s, 9H).

(3) 2(S)-Amino-1-[2-[5-(2-dimethylaminoethoxy)methyl]furyl]-3-phenyl-1-propanone Ditrifluoroacetate The title compound of Example 4(2) was treated in the same manner as in Example 1(4) to give the title compound quantitatively as a red oil.

$^1$H-NMR (300 MHz, DMSO-d$_6$) δ 9.45–9.10 (br, 3H), 8.60–8.40 (br, 1H), 7.59 (d, J=3.7 Hz, 1H), 7.35–7.15 (m, 5H), 6.72 (d, J=3.7 Hz, 1H), 5.10–4.90 (m, 1H), 4.58 (s, 2H), 3.80–3.65 (m, 2H), 3.20–3.10 (m, 4H), 2.78 (s, 6H).

(4) tert-Butyl 3(R)-[1(S)-[2-[5-(2-Dimethylaminoethoxy)methyl]furyl]carbonyl-2-phenyl]ethylcarbamoyl-5-methyl-2(R or S)-phthalimidomethylhexanoate In the same manner as in Example 1(5), 4-tert-butoxy-2(R)-isobutyl-3(R or S)-phthalimidomethylsuccinic acid and the title compound of Example 4(3) were reacted and the resulting product was purified by silica gel column chromatography (10:1 chloroform-methanol) to give the title compound as an amorphous solid at an overall yield (2 steps) of 20% from the title compound of Example 4(2).

$^1$H-NMR (300 MHz, DMSO-d$_6$) δ 8.77 (d, J=8.5 Hz, 1H), 7.98–7.80 (m, 4H), 7.61 (d, J=3.5 Hz, 1H), 7.35 (d, J=7.0 Hz, 2H), 7.12 (t, J=7.6 Hz, 2H), 6.86 (t, J=7.3 Hz, 1H), 6.67 (d, J=3.5 Hz, 1H), 5.50–5.35 (m, 1H), 4.52 (s, 2H), 3.60–3.40 (m, 1H), 3.52 (t, J=5.9 Hz, 2H), 3.10 (dd, J=13.9, 4.4 Hz, 1H), 2.87 (dd, J=13.9, 10.7 Hz, 1H), 2.78–2.45 (m, 2H), 2.45–2.30 (m, 1H), 2.40 (t, J=5.9 Hz, 2H), 2.13 (s, 6H), 1.55–1.30 (m, 1H), 1.30–1.05 (m, 1H), 1.09 (s, 9H), 0.90–0.70 (m, 1H), 0.79 (d, J=6.4 Hz, 3H), 0.68 (d, J=6.4 Hz, 3H).

(5) 3(R)-[1(S)-[2-[5-(2-Dimethylaminoethoxy)methyl]furyl]carbonyl-2-phenyl]ethylcarbamoyl-5-methyl-2(R or S)-phthalimidomethylhexanoic Acid Trifluoroacetate The title compound of Example 4(4) was treated in the same manner as in Example 1(8) to give the title compound (yield 98%) as an amorphous solid.

$^1$H-NMR (300 MHz, DMSO-d$_6$) δ 12.60–12.30 (br, 1H), 9.50–9.25 (br, 1H), 8.75 (d, J=8.2 Hz, 1H), 7.95–7.75 (m, 4H), 7.63 (d, J=3.5 Hz, 1H), 7.35 (d, J=7.3 Hz, 2H), 7.13 (t, J=7.6 Hz, 2H), 6.87 (t, J=7.4 Hz, 1H), 6.75 (d, J=3.5 Hz, 1H), 5.48–5.32 (m, 1H), 4.63 (s, 2H), 3.82–3.70 (m, 2H), 3.45 (dd, J=13.4, 11.1 Hz, 1H), 3.10 (dd, J=13.9, 4.5 Hz, 1H), 2.86 (dd, J=13.9, 10.9 Hz, 1H), 2.85–2.40 (m, 5H), 1.55–1.30 (m, 1H), 1.30–1.10 (m, 1H), 0.95–0.75 (m, 1H), 0.80 (d, J=6.5 Hz, 3H), 0.70 (d, J=6.5 Hz, 3H).

(6) 2-Tetrahydropyranyl 3(R)-[1(S)-[2-[5-(2-Dimethylaminoethoxy)methyl]furyl]carbonyl-2-phenyl]ethylcarbamoyl-5-methyl-2(R or S)-phthalimidomethylhexanohydroxamate In the same manner as in Example 1(9), the title compound of Example 4(5) and O-2-tetrahydropyranylhydroxylamine were reacted and the resulting product was purified by silica gel column chromatography (10:1 chloroform-methanol) to give the title compound (yield 47%) as an amorphous solid.

$^1$H-NMR (500 MHz, DMSO-d$_6$) δ 11.00–10.85 (m, 1H), 8.72–8.65 (m, 1H), 7.88–7.78 (m, 4H), 7.64–7.58 (m, 1H), 7.35 (d, J=7.1 Hz, 2H), 7.08 (t, J=7.6 Hz, 2H), 6.73–6.68 (m, 1H), 6.67 (d, J=3.5 Hz, 1H), 5.42–5.32 (m, 1H), 4.52 (s, 2H), 4.57–4.35 (m, 1H), 3.72–3.30 (m, 2H), 3.53 (t, J=5.9 Hz, 2H), 3.13–3.00 (m, 1H), 2.92–2.78 (m, 1H), 2.78–2.20 (m, 4H), 2.41 (t, J=5.9 Hz, 2H), 2.13 (s, 6H), 1.60–1.10 (m, 8H), 0.95–0.75 (m, 1H), 0.76 (d, J=6.5 Hz, 3H), 0.67 (d, J=6.5 Hz, 3H).

(7) 3(R)-[1(S)-[2-[5-(2-Dimethylaminoethoxy)methyl]furyl]carbonyl2-phenyl]ethylcarbamoyl-5-methyl-2(R or S)-phthalimidomethylhexanohydroxamic Acid Hydrochloride The title compound of Example 4(6) was treated in the same manner as in Example 1(10) and the resulting product was crystallized from diethyl ether to give the title compound (yield 63%) as a white solid.

$^1$H-NMR (500 MHz, DMSO-d$_6$) δ 10.33 (br s, 1H), 8.68 (d, J=8.1 Hz, 1H), 8.60 (br s, 1H), 7.90–7.80 (m, 4H), 7.62 (d, J=3.5 Hz, 1H), 7.35 (d, J=7.1 Hz, 2H), 7.09 (t, J=7.7 Hz, 2H), 6.81 (t, J=7.4 Hz, 1H), 6.74 (d, J=3.5 Hz, 1H), 5.40–5.32 (m, 1H), 4.63 (s, 2H), 3.79 (t, J=5.1 Hz, 2H), 3.48 (dd, J=13.4, 11.3 Hz, 1H), 3.09 (dd, J=13.8, 4.4 Hz, 1H), 2.86 (dd, J=13.8, 10.7 Hz, 1H), 2.80–2.72 (m, 2H), 2.78 (s, 6H), 2.67–2.40 (m, 2H), 2.30 (dd, J=13.4, 4.4 Hz, 1H), 1.45–1.35 (m, 1H), 1.27–1.15 (m, 1H), 0.90–0.75 (m, 1H), 0.78 (d, J=6.6 Hz, 3H), 0.69 (d, J=6.6 Hz, 3H).

Example 5

3(R)-[2-[4-(2-Dimethylaminoethoxy)phenyl]-1(S)-(2-furyl)carbonyl]ethylcarbamoyl-5-methyl-2(R or S)-(2,5-dioxo-3,4,4-trimethyl-1-imidazolidinyl)methylhexanohydroxamic Acid Hydrochloride

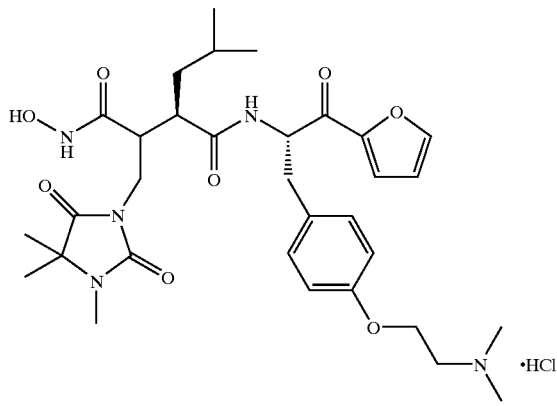

(1) N$^\alpha$-(tert-Butoxycarbonyl)-L-(O-benzyl)tyrosine N-Methoxy-N-methylamide According to the method of Jean-Alain Fehrentz et al. [Synthesis (1983) 676–678], N-(tert-butoxycarbonyl)-L-(O-benzyl)tyrosine and N,O-dimethylhydroxylamine hydrochloride were reacted, and the resulting product was purified by silica gel column chromatography (2:1 hexane-ethyl acetate) and recrystallized from ethyl acetate-hexane to give the title compound (yield 89%) as a white solid.

¹H-NMR (300 MHz, CDCl₃) δ 7.50–7.20 (m, 5H), 7.08 (d, J=8.5 Hz, 2H), 6.89 (d, J=8.5 Hz, 2H), 5.22–5.08 (m, 1H), 5.03 (s, 2H), 4.98–4.80 (m, 1H), 3.65 (br s, 3H), 3.16 (br s, 3H), 3.07–2.90 (m, 1H), 2.90–2.75 (m, 1H), 1.39 (s, 9H).

(2) 3-(4-Benzyloxy)phenyl-2(S)-(tert-butoxycarbonyl)amino-1-(2-furyl)-1-propanone According to the method of Example 1(3), furan and the title compound of Example 5(1) were reacted, and the product was purified by silica gel column chromatography (1:1 hexane-ethyl acetate) and crystallized from hexane to give the title compound (yield 83%) as a yellow solid.

¹H-NMR (300 MHz, CDCl₃) δ 7.65–7.55 (m, 1H), 7.48–7.25 (m, 5H), 7.23 (d, J=3.6 Hz, 1H), 7.00 (d, J=8.4 Hz, 2H), 6.85 (d, J=8.4 Hz, 2H), 6.60–6.45 (m, 1H), 5.38–5.15 (m, 2H), 5.02 (br s, 2H), 3.16 (dd, J=13.6, 4.9 Hz, 1H), 2.98 (dd, J=13.6, 5.3 Hz, 1H), 1.41 (s, 9H).

(3) 2(S)-Amino-3-(4-benzyloxy)phenyl-1-(2-furyl)-1-propanone Trifluoroacetate

The title compound of Example 5(2) was treated in the same manner as in Example 1(4) and the product was crystallized from diethyl ether-hexane to give the title compound quantitatively as a brown solid.

¹H-NMR (300 MHz, DMSO-d₆) δ 8.60–8.20 (br, 3H), 8.08 (d, J=1.6 Hz, 1H), 7.63 (d, J=3.6 Hz, 1H), 7.50–7.25 (m, 5H), 7.09 (d, J=8.6 Hz, 2H), 6.92 (d, J=8.6 Hz, 2H), 6.75 (dd, J=3.6, 1.6 Hz, 1H), 5.06 (s, 2H), 4.95 (t, J=6.7 Hz, 1H), 3.07 (d, J=6.7 Hz, 2H).

(4) tert-Butyl 3(R)-[2-(4-Benzyloxy)phenyl-1(S)-(2-furyl)carbonyl]ethylcarbamoyl-5-methyl-2(R or S)-(2,5-dioxo-3,4,4-trimethyl-1-imidazolidinyl)methylhexanoate In the same manner as in Example 1(5), 4-tert-butoxy-2(R)-isobutyl-3(R or S)-(2,5-dioxo-3,4,4-trimethyl-1-imidazolidinyl)methylsuccinic acid prepared according to the method described in JP-A-6-65196 and the title compound, of Example 5(3) were reacted and the product was purified by silica gel column chromatography (1:1 hexane-ethyl acetate) to give the title compound (yield 68%) as an amorphous solid.

¹H-NMR (300 MHz, DMSO-d₆) δ 8.69 (d, J=8.5 Hz, 1H), 8.04 (d, J=1.6 Hz, 1H), 7.65 (d, J=3.6 Hz, 1H), 7.45–7.25 (m, 5H), 7.26 (d, J=8.5 Hz, 2H), 6.79 (d, J=8.5 Hz, 2H), 6.74 (dd, J=3.6, 1.6 Hz, 1H), 5.42–5.30 (m, 1H), 4.94 (s, 2H), 3.40–3.18 (m, 1H), 3.02 (dd, J=13.8, 4.3 Hz, 1H), 2.90–2.70 (m, 1H), 2.65 (s, 3H), 2.70–2.40 (m, 2H), 2.19 (dd, J=13.4, 4.4 Hz, 1H), 1.37–1.00 (m, 1H), 1.29 (s, 9H), 1.26 (s, 6H), 0.90–0.70 (m, 1H), 0.79 (d, J=6.5 Hz, 3H), 0.68 (d, J=6.5 Hz, 3H).

(5) tert-Butyl 3(R)-[1(S)-(2-Furyl)carbonyl-2-(4-hydroxy)phenyl]ethylcarbamoyl-5-methyl-2(R or S)-(2,5-dioxo-3,4,4-trimethyl-1-imidazolidinyl)methylhexanoate In the same manner as in Example 1(6), the title compound of Example 5(4) was subjected to catalytic hydrogenation and the resulting product was purified by silica gel column chromatography (50:1 chloroform-methanol) to give the title compound (yield 49%) as an amorphous solid.

¹H-NMR (300 MHz, DMSO-d₆) δ 9.04 (br s, 1H), 8.66 (d, J=8.4 Hz, 1H), 8.03 (d, J=1.6 Hz, 1H), 7.61 (d, J=3.6 Hz, 1H), 7.10 (d, J=8.0 Hz, 2H), 6.73 (dd, J=3.6, 1.6 Hz, 1H), 6.52 (d, J=8.0 Hz, 2H), 5.38–5.25 (m, 1H), 2.96 (dd, J=13.8, 4.5 Hz, 1H), 2.88–2.65 (m, 1H), 2.76 (s, 3H), 2.65–2.40 (m, 2H), 2.21 (dd, J=13.6, 4.6 Hz, 1H), 1.55–1.38 (m, 1H), 1.30 (s, 9H), 1.26 (s, 6H), 1.25–1.05 (m, 1H), 0.85–0.70 (m, 1H), 0.78 (d, J=6.5 Hz, 3H), 0.68 (d, J=6.5 Hz, 3H).

(6) tert-Butyl 3(R)-[2-[4-(2-Dimethylaminoethoxy)phenyl]-1(s)-(2-furyl)carbonyl]ethylcarbamoyl-5-methyl-2(R or S)-(2,5-dioxo-3,4,4-trimethyl-1-imidazolidinyl)methylhexanoate In the same manner as in Example 1(7), the title compound of Example 5(5) and 2-dimethylaminoethanol were reacted and the product was purified by silica gel column chromatography (20:1 chloroform-methanol) to give the title compound as an amorphous solid.

¹H-NMR (300 MHz, CDCl₃) δ 7.60 (d, J=1.7 Hz, 1H), 7.28 (d, J=3.6 Hz, 1H), 7.18 (d, J=8.5 Hz, 1H), 7.10 (d, J=8.5 Hz, 2H), 6.75 (d, J=8.5 Hz, 2H), 6.52 (dd, J=3.6, 1.7 Hz, 1H), 5.70–5.58 (m, 1H), 3.98 (t, J=5.8 Hz, 2H), 3.43 (dd, J=14.3, 4.9 Hz, 1H), 3.25 (dd, J=14.3, 6.2 Hz, 1H), 3.20 (dd, J=14.6, 6.1 Hz, 1H), 2.99 (dd, J=14.6, 8.2 Hz, 1H), 2.85–2.75 (m, 1H), 2.70–2.55 (m, 1H), 2.67 (t, J=5.8 Hz, 2H), 2.31 (s, 6H), 1.70–1.55 (m, 1H), 1.45–1.20 (m, 1H), 1.39 (s, 9H), 1.37 (s, 6H), 1.05–0.95 (m, 1H), 0.80 (d, J=6.5 Hz, 3H), 0.76 (d, J=6.5 Hz, 3H).

(7) 3(R)-[2-[4-(2-Dimethylaminoethoxy)phenyl]-1(S)-(2-furyl)carbonyl]ethylcarbamoyl-5-methyl-2(R or S)-(2,5-dioxo-3,4,4-trimethyl-1-imidazolidinyl)methylhexanoic Acid Trifluoroacetate The title compound of Example 5(6) was treated in the same manner as in Example 1(8) to give the title compound as an amorphous solid.

¹H-NMR (300 MHz, DMSO-d₆) δ 8.69 (d, J=8.3 Hz, 1H), 8.02 (d, J=1.7 Hz, 1H), 7.59 (d, J=3.5 Hz, 1H), 7.27 (d, J=8.6 Hz, 2H), 6.81 (d, J=8.6 Hz, 2H), 6.72 (dd, J=3.5, 1.7 Hz, 1H), 5.40–5.28 (m, 1H), 4.20–4.00 (m, 2H), 3.40–3.28 (m, 1H), 3.28–3.15 (m, 2H), 3.04 (dd, J=13.8, 5.6 Hz, 1H), 2.82 (s, 6H), 2.90–2.70 (m, 1H), 2.70–2.40 (m, 3H), 1.50–1.35 (m, 1H), 1.30–1.10 (m, 1H), 1.25 (s, 6H), 0.90–0.75 (m, 1H), 0.75 (d, J=6.5 Hz, 3H), 0.67 (d, J=6.5 Hz, 3H).

(8) 2-Tetrahydropyranyl 3(R)-[2-[4-(2-Dimethylaminoethoxy)phenyl]-1(S)-(2-furyl)carbonyl]ethylcarbamoyl-5-methyl-2(R or S)-(2,5-dioxo-3,4,4-trimethyl-1-imidazolidinyl)methylhexanohydroxamate In the same manner as in Example 1(9), the title compound of Example 5(7) and O-2-tetrahydropyranylhydroxylamine were reacted, and the resulting product was purified by silica gel column chromatography (20:1 chloroform-methanol) and crystallized from hexane to give the title compound as a pale-yellow solid at an overall yield (3 steps) of 42% from the title compound of Example 5(5).

¹H-NMR (300 MHz, DMSO-d₆) δ 11.10–10.90 (m, 1H), 8.65–8.50 (m, 1H), 8.08–8.00 (m, 1H), 7.70–7.62 (m, 1H), 7.25 (d, J=8.4 Hz, 2H), 6.88–6.63 (m, 3H), 5.38–5.20 (m, 1H), 4.12–3.95 (m, 2H), 3.95–3.70 (m, 1H), 33–3.10 (m, 1H), 3.08–2.95 (m, 1H), 2.85–2.05 (m, 10H), 2.20 (s, 6H), 1.70–1.05 (m, 14H), 0.90–0.70 (m, 1H), 0.76 (d, J=6.5 Hz, 3H), 0.67 (d, J=6.5 Hz, 3H).

(9) 3(R)-[2-[4-(2-Dimethylaminoethoxy)phenyl]-1(S)-(2-furyl)carbonyl]ethylcarbamoyl-5-methyl-2(R or S)-(2,5-dioxo-3,4,4-trimethyl-1-imidazolidinyl)methylhexanohydroxamic Acid Hydrochloride The title compound of Example 5(8) was treated in the same manner as in Example 1(10) and diethyl ether was added to the reaction mixture. The precipitated solid was collected by filtration. The obtained solid was purified by reversed phase column chromatography (Chromatorex ODS DM-1020T, Fuji Silysia Chemical Ltd.; 17–33% acetonitrile-0.1% aqueous trifluoroacetic acid solution) and lyophilized. 0.1N Hydrochloric acid (20 ml) was added to the obtained residue and the mixture was again lyophilized to give the title compound (164 mg, 45%) as an amorphous solid.

¹H-NMR (500 MHz, DMSO-d₆) δ 10.37 (br s, 1H), 9.95–9.75 (br, 1H), 8.72–8.62 (br, 1H), 8.61 (d, J=8.0 Hz, 1H), 8.01 (d, J=1.7 Hz, 1H), 7.58 (d, J=3.6 Hz, 1H), 7.27 (d,

J=8.6 Hz, 2H), 6.80 (d, J=8.6 Hz, 2H), 6.72 (dd, J=3.6, 1.7 Hz, 1H), 5.32–5.25 (m, 1H), 4.22–4.10 (m, 2H), 3.45–3.20 (m, 3H), 3.03 (dd, J=13.9, 5.3 Hz, 1H), 2.88–2.80 (m, 1H), 2.81 (s, 6H), 2.76 (s, 3H), 2.57–2.45 (m, 2H), 2.40–2.30 (m, 1H), 1.43–1.35 (m, 1H), 1.25 (s, 3H), 1.23 (s, 3H), 1.20–1.10 (m, 1H), 0.85–0.75 (m, 1H), 0.74 (d, J=6.6 Hz, 3H), 0.67 (d, J=6.6 Hz, 3H).

Example 6

Sodium Salt of 3(R)-[1(S)-(2-furyl)carbonyl-2-[4-(hydroxysulfonyloxy)phenyl]]ethylcarbamoyl-5-methyl-2(R or S)-phthalimidomethylhexanohydroxamic Acid

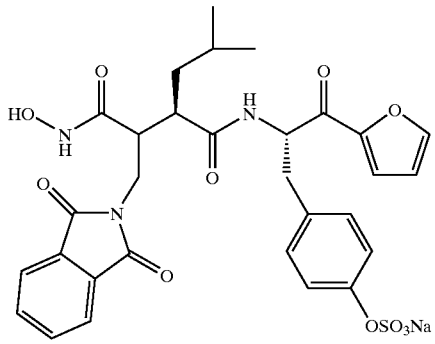

(1) tert-Butyl 3(R)-[2-(4-Benzyloxy)phenyl-1(S)-(2-furyl)carbonyl]ethylcarbamoyl-5-methyl-2(R or S)-phthalimidomethylhexanoate In the same manner as in Example 1(5), 4-tert-butoxy-2(R)-isobutyl-3(R or S)-phthalimidomethylsuccinic acid and the title compound of Example 5(3) were reacted, and the resulting product was purified by silica gel column chromatography (2:1 hexane-ethyl acetate) and recrystallized from ethyl acetate-hexane to give the title compound (yield 56%) as a white solid.

$^1$H-NMR (300 MHz, DMSO-d$_6$) δ 8.73 (d, J=8.8 Hz, 1H), 8.07 (d, J=1.3 Hz, 1H), 7.90–7.73 (m, 4H), 7.73 (d, J=3.4 Hz, 1H), 7.31 (d, J=8.6 Hz, 2H), 7.25–7.10 (m, 3H), 6.98–6.85 (m, 2H), 6.80–6.70 (m, 3H), 5.55–5.40 (m, 1H), 4.57 (s, 2H), 3.45–3.25 (m, 1H), 3.06 (dd, J 13.8, 4.0 Hz, 1H), 2.79 (dd, J=13.8, 11.8 Hz, 1H), 2.64 (ddd, J=11.2, 11.1, 5.0 Hz, 1H), 2.58–2.45 (m, 1H), 2.10 (dd, J=13.7, 5.1 Hz, 1H), 1.55–1.38 (m, 1H), 1.25–0.95 (m, 1H), 1.07 (s, 9H), 0.90–0.60 (m, 1H), 0.78 (d, J=6.5 Hz, 3H), 0.68 (d, J=6.5 Hz, 3H).

(2) tert-Butyl 3(R)-[1(S)-(2-Furyl)carbonyl-2-(4-hydroxy)phenyl]ethylcarbamoyl-5-methyl-2(R or S)-phthalimidomethylhexanoate In the same manner as in Example 1(6), the title compound of Example 6(1) was subjected to catalytic hydrogenation, and the product was purified by silica gel column chromatography (1:1 hexane-ethyl acetate) to give the title compound (yield 62%) as an amorphous solid.

$^1$H-NMR (300 MHz, DMSO-d$_6$) δ 8.82 (br s, 1H), 8.69 (d, J=8.6 Hz, 1H), 8.05 (d, J=1.7 Hz, 1H), 7.92–7.80 (m, 4H), 7.65 (d, J=3.6 Hz, 1H), 7.11 (d, J=8.4 Hz, 2H), 6.74 (dd, J=3.6, 1.7 Hz, 1H), 6.48 (d, J=8.4 Hz, 2H), 5.45–5.30 (m, 1H), 3.50–3.30 (m, 1H), 2.99 (dd, J=13.8, 4.5 Hz, 1H), 2.75–2.60 (m, 1H), 2.73 (dd, J=13.8, 11.1 Hz, 1H), 2.60–2.45 (m, 1H), 2.28 (dd, J=13.7, 5.2 Hz, 1H), 1.55–1.38 (m, 1H), 1.32–1.05 (m, 1H), 1.09 (s, 9H), 0.90–0.70 (m, 1H), 0.78 (d, J=6.5 Hz, 3H), 0.68 (d, J=6.5 Hz, 3H).

(3) 3(R)-[1(S)-(2-Furyl)carbonyl-2-(4-hydroxy)phenyl]ethylcarbamoyl-5-methyl-2(R or S)-phthalimidomethylhexanoic Acid The title compound of Example 6(2) was treated in the same manner as in Example 1(8) and the product was recrystallized from diethyl ether to give the title compound (yield 87%) as a white solid.

$^1$H-NMR (300 MHz, DMSO-d$_6$) δ 12.70–12.00 (br, 1H), 9.00–8.70 (br, 1H), 8.66 (d, J=8.6 Hz, 1H), 8.05 (d, J=1.6 Hz, 1H), 7.90–7.75 (m, 4H), 7.64 (d, J=3.6 Hz, 1H), 7.11 (d, J=8.4 Hz, 2H), 6.74 (dd, J=3.6, 1.6 Hz, 1H), 6.48 (d, J=8.4 Hz, 2H), 5.42–5.30 (m,1H), 3.42 (dd, J=13.7, 11.3 Hz, 1H), 2.99 (dd, J=13.8, 4.5 Hz, 1H), 2.75–2.45 (m, 2H), 2.73 (dd, J=13.8, 11.2 Hz, 1H), 2.38 (dd, J=13.7, 4.8 Hz, 1H), 1.55–1.38 (m, 1H), 1.28–1.05 (m, 1H), 0.92–0.75 (m, 1H), 0.77 (d, J=6.5 Hz, 3H), 0.68 (d, J=6.5 Hz, 3H).

(4) 2-Tetrahydropyranyl 3(R)-[1(S)-(2-Furyl)carbonyl-2-(4-hydroxy)phenyl]ethylcarbamoyl-5-methyl-2(R or S)-phthalimidomethylhexanohydroxamate In the same manner as in Example 1(9), the title compound of Example 6(3) and O-2-tetrahydropyranylhydroxylamine were reacted and the resulting product was purified by silica gel column chromatography (20:1 chloroform-methanol) to give the title compound (yield 75%) as a white solid.

$^1$H-NMR (300 MHz, DMSO-d$_6$) δ 11.00–10.85 (m, 1H), 8.77 (br s, 1H), 8.70–8.55 (m, 1H), 8.10–8.00 (m, 1H), 7.90–7.75 (m, 4H), 7.68–7.60 (m, 1H), 7.11 (d, J=8.3 Hz, 2H), 6.74 (dd, J=3.6, 1.6 Hz, 1H), 6.46 (d, J=8.3 Hz, 2H), 5.40–5.25 (m, 1H), 4.60–4.30 (m, 1H), 3.75–3.35 (m, 2H), 3.10–2.65 (m, 1H), 2.98 (dd, J=13.9, 4.5 Hz, 1H), 2.73 (dd, J=13.9, 11.0 Hz, 1H), 2.65–2.38 (m, 2H), 2.38–2.20 (m, 1H), 1.65–1.05 (m, 8H), 0.90–0.70 (m, 1H), 0.76 (d, J=6.4 Hz, 3H), 0.67 (d, J=6.4 Hz, 3H).

(5) Sodium Salt of 2-Tetrahydropyranyl 3(R)-[1(S)-(2-Furyl)carbonyl-2-[4-(hydroxysulfonyloxy)phenyl]]ethylcarbamoyl-5-methyl-2(R or S)-phthalimidomethylhexanohydroxamate The title compound (500 mg, 0.77 mmol) of Example 6(4) was dissolved in DMF (3 ml) and a pyridine-sulfur trioxide complex (370 mg, 2.32 mmol) was added to the solution under ice-cooling. The mixture was stirred for 2 hr at room temperature. A 1N aqueous sodium hydrogencarbonate solution (20 ml) was added to the reaction mixture and the mixture was stirred for 30 min at room temperature. The reaction mixture was purified by reversed phase column chromatography (Chromatorex ODS DM-1020T, Fuji Silysia Chemical Ltd.; 0–50% aqueous methanol solution) and lyophilized to give the title compound (528 mg, 91%) as an amorphous solid.

$^1$H-NMR (300 MHz, DMSO-d$_6$) δ 11.30–10.60 (br, 1H), 8.80–8.70 (m, 1H), 8.05–7.97 (m, 1H), 7.85–7.75 (m, 4H), 7.60–7.50 (m, 1H), 7.18 (d, J=8.4 Hz, 2H), 6.93 (d, J=8.4 Hz, 2H), 6.70 (dd, J=3.6, 1.8 Hz, 1H), 5.32–5.20 (m, 1H), 4.60–4.35 (m, 1H), 3.80–3.20 (m, 3H), 3.10–2.95 (m, 1H), 2.93–2.70 (m, 2H), 2.70–2.50 (m, 2H), 1.60–1.10 (m, 8H), 0.90–0.75 (m, 1H), 0.77 (d, J=6.4 Hz, 3H), 0.68 (d, J=6.4 Hz, 3H).

(6) Sodium Salt of 3(R)-[1(S)-(2-Furyl)carbonyl-2-[4-(hydroxysulfonyloxy)phenyl]]ethylcarbamoyl-5-methyl-2(R or S)-phthalimidomethylhexanohydroxamic Acid To a solution of the title compound (200 mg, 0.27 mmol) of Example 6(5), water (1.5 ml) and methanol (3 ml) was added 1N hydrochloric acid (1.5 ml) and the mixture was stirred for 1.5 hr at room temperature. Then, 1N aqueous sodium hydrogencarbonate solution (1.5 ml) was added and the mixture was stirred for 30 min at room temperature. The reaction mixture was concentrated, and the obtained residue was purified by reversed phase column chromatography (Chromatorex ODS DM-1020T, Fuji Silysia Chemical Ltd.;

0–17% aqueous methanol solution) and lyophilized to give the title compound (94 mg, 53%) as an amorphous solid.

$^1$H-NMR (300 MHz, DMSO-d$_6$) δ 10.38 (br s, 1H), 8.72 (d, J=8.0 Hz, 1H), 8.63 (br s, 1H), 8.03–7.95 (m, 1H), 7.87–7.75 (m, 4H), 7.52 (d, J=3.5 Hz, 1H), 7.17 (d, J=8.4 Hz, 2H), 6.93 (t, J=8.4 Hz, 2H), 6.69 (dd, J=3.5, 1.5 Hz, 1H), 5.30–5.18 (m, 1H), 3.80–3.60 (m, 1H), 3.02 (dd, J=13.9, 5.5 Hz, 1H), 2.90–2.74 (m, 1H), 2.87 (dd, J=13.9, 9.0 Hz, 1H), 2.70–2.50 (m, 2H), 1.52–1.32 (m, 1H), 1.30–1.10 (m, 1H), 0.92–0.75 (m, 1H), 0.77 (d, J=6.4 Hz, 3H), 0.69 (d, J=6.4 Hz, 3H).

Example 7

Sodium Salt of 3(R)-[1(S)-(2-Furyl)carbonyl-2-(4-sulfophenyl)ethylcarbamoyl]-5-methyl-2(R or S)-(2-naphthylmethyl)hexanohydroxamic Acid

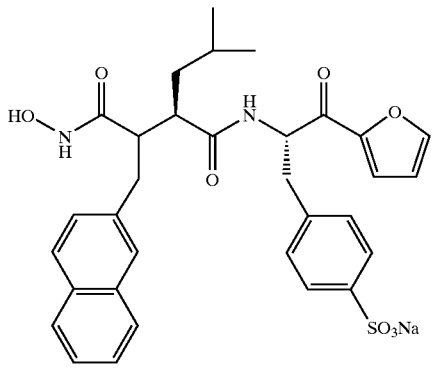

(1) N-Benzyloxycarbonyl-L-4'-sulfophenylalanine

To a suspension of L-4'-sulfophenylalanine (368 g, 1.50 mol) in water (2 L) was added sodium hydrogencarbonate (508 g, 6.05 mol) over 20 min under ice-cooling. Then, benzyl chloroformate (300 ml, 2.00 mol) was added dropwise over 20 min under ice-cooling, and the mixture was stirred for 4 hr at room temperature. The reaction mixture was washed with ethyl acetate (3×1 L) and filtrated. 6N Hydrochloric acid (1020 ml, 6.12 mol) was added to the filtrate under ice-cooling, and the obtained acidic aqueous solution was saturated with sodium chloride and extracted with THF (4×1 L). The THF solution was washed with saturated brine (2 L), dried over anhydrous magnesium sulfate and concentrated to give the title compound (509 g, 89%) as a white solid.

$^1$H-NMR (300 MHz, DMSO-d$_6$) δ 7.66 (d, J=8.4 Hz, 1H), 7.52 (d, J=8.1 Hz, 2H), 7.43–7.25 (m, 5H), 7.21 (d, J=8.1 Hz, 2H), 4.98 (s, 2H), 4.27–4.13 (m, 1H), 3.07 (dd, J=13.6, 4.4 Hz, 1H), 2.84 (dd, J=13.6, 10.5Hz, 1H).

(2) N$^α$-Benzyloxycarbonyl-L-4'-sulfophenylalanine N-Methoxy-N-methylamide

According to the method of Jean-Alain Fehrentz et al. [Synthesis (1983) 676–678], to a solution of the title compound (57.4 g, 151 mmol) of Example 7(1) dissolved in DMF (180 ml) were added N,O-dimethylhydroxylamine (17.7 g, 182 mmol) and BOP reagent (86.7 g, 196 mmol). Triethylamine (84 ml, 604 mmol) was added dropwise under ice-cooling and the mixture was stirred under ice-cooling for 30 min, and at room temperature for 5 hr. THF (1.5 L) was added to the reaction mixture, and the mixture was washed successively with a 2:1 mixed solution (1.2 L) of saturated aqueous sodium hydrogencarbonate solution and saturated brine and saturated brine (0.6 L), dried over anhydrous magnesium sulfate and concentrated. The residue was purified by silica gel column chromatography (10:1 chloroform-methanol) to give the title compound (37.1 g, 55%) as a white solid.

$^1$H-NMR (300 MHz, DMSO-d$_6$) δ 7.73 (d, J=8.6 Hz, 1H), 7.52 (d, J=8.0 Hz, 2H), 7.40–7.21 (m, 5H), 7.20 (d, J=8.0 Hz, 2H), 4.95 (s, 2H), 4.70–4.50 (m, 1H), 3.74 (s, 3H), 3.11 (s, 3H), 2.89 (dd, J=13.6, 4.3 Hz, 1H), 2.73 (dd, J=13.6, 9.9 Hz, 1H).

(3) 2(S)-(N-Benzyloxycarbonylamino)-1-(2-furyl)-3-(4-sulfophenyl)-1-propanone

To a solution of furan (10 ml, 137 mmol) dissolved in THF (90 ml) was added dropwise n-butyllithium (1.54M hexane solution, 65 ml, 100 mmol) at –70° C. over 10 min and the mixture was stirred for 2 hr at –30° C. Then a solution of the title compound (7.42 g, 16.7 mmol) of Example 7(2) dissolved in THF (110 ml) was added dropwise at –70° C. over 20 min and the mixture was stirred for 2 hr at –40° C. The reaction mixture was added to 1N hydrochloric acid (140 ml) saturated with sodium chloride to separate the organic layer from the aqueous layer. The aqueous layer was extracted with THF (2×200 ml). The organic layer and THF layer were combined, dried over anhydrous magnesium sulfate and concentrated. The residue was purified by silica gel column chromatography (10:1 chloroform-methanol) to give the title compound (6.65 g, 93%) as a brown oil.

$^1$H-NMR (300 MHz, DMSO-d$_6$) δ 8.10–8.00 (m, 1H), 7.92 (d, J=8.5 Hz, 1H), 7.65–7.55 (m, 1H), 7.51 (d, J=8.0 Hz, 2H), 7.40–7.18 (m, 7H), 6.78–6.67 (m, 1H), 5.05–4.95 (m, 3H), 3.05 (dd, J=13.5, 4.4 Hz, 1H), 2.82 (dd, J=13.5, 10.4 Hz, 1H).

(4) 2(S)-Amino-1-(2-furyl)-3-(4-sulfophenyl)-1-propanone Trifluoroacetate

A mixture of the title compound (7.63 g, 17.8 mmol) of Example 7(3), thioanisole (3.2 ml, 27.3 mmol) and trifluoroacetic acid (26 ml) was stirred for 3 hr at room temperature. Thioanisole (3.2 ml, 27.3 mmol) was added and the mixture was stirred for 1.5 hr at room temperature. Then, thioanisole (2.2 ml, 18.7 mmol) was added, and the mixture was stirred at room temperature for 1 hr. Diethyl ether (360 ml) was added to the reaction mixture and the precipitate was collected by filtration, and washed with diethyl ether. The obtained precipitate was reprecipitated from methanol-ethyl acetate to give the title compound (4.29 g, 59%) as a purple powder.

$^1$H-NMR (300 MHz, DMSO-d$_6$) δ 8.34 (br s, 3H), 8.13 (d, J=1.2 Hz, 1H), 7.73 (d, J=3.7 Hz, 1H), 7.53 (d, J=8.0 Hz, 2H), 7.16 (d, J=8.1 Hz, 2H), 6.80 (dd, J=3.6, 1.6 Hz, 1H), 5.06–4.96 (m, 1H), 3.19 (dd, J=14.2, 5.8Hz, 1H), 3.08 (dd, J=14.2, 7.4Hz, 1H).

(5) Sodium Salt of tert-Butyl 3(R)-[1(S)-(2-furylcarbonyl)-2-(4-sulfophenyl)ethylcarbamoyl]-5-methyl-2(R or S)-(2-naphthylmethyl)hexanoic Acid In the same manner as in Example 1(5), 4-tert-butoxy-2(R)-isobutyl-3(R or S)-(2-naphthylmethyl)succinic acid prepared according to the method described in JP-A-4-352757 and the title compound of Example 7(4) were reacted. After the completion of the reaction, ethyl acetate was added to the reaction mixture, and the mixture was washed successively with 1N hydrochloric acid saturated with sodium chloride, a 2:1 mixed solution of saturated aqueous sodium hydrogencarbonate solution and saturated brine and saturated brine, dried over anhydrous magnesium sulfate, and concentrated. The residue was purified by silica gel column chromatography (10:1 chloroform-methanol) to give the title compound (yield 96%) as a pale-yellow foam.

$^1$H-NMR (300 MHz, DMSO-d$_6$) δ 8.78 (d, J=7.5 Hz, 1H), 8.00 (d, J=1.4 Hz, 1H), 7.89–7.78 (m, 3H), 7.57 (d, J=3.6

Hz, 1H), 7.55 (s, 1H), 7.49 (d, J=8.2 Hz, 2H), 7.48–7.43 (m, 2H), 7.27 (d, J=8.2 Hz, 2H), 7.23 (dd, J=8.5, 1.5 Hz, 1H), 6.70 (dd, J=3.6, 1.7 Hz, 1H), 5.39–5.26 (m, 1H), 3.13 (dd, J=14.1, 5.2 Hz, 1H), 2.98 (dd, J=14.2, 9.0 Hz, 1H), 2.78–2.65 (m, 3H), 2.65–2.54 (m, 1H), 1.64–1.49(m, 1H), 1.29–1.18 (m, 1H), 1.14 (s, 9H), 0.97–0.84 (m, 1H), 0.78 (d, J=6.4 Hz, 3H), 0.72 (d, J=6.5 Hz, 3H).

(6) 3(R)-[1(S)-(2-Furylcarbonyl)-2-(4-sulfophenyl)ethylcarbamoyl]-5-methyl-2(R or S)-(2-naphthylmethyl)hexanoic Acid In the same manner as in Example 1(8), the title compound of Example 7(5) was dissolved in trifluoroacetic acid and the mixture was stirred for 1.5 hr at room temperature. The reaction mixture was concentrated, and diethyl ether was added to the residue to give the title compound (quantitatively) as a pale-green powder.

$^1$H-NMR (300 MHz, DMSO-d$_6$) δ 13.20–11.60 (br), 8.77 (d, J=7.5 Hz, 1H), 8.00 (d, J=1.4 Hz, 1H), 7.89–7.78 (m, 3H), 7.60–7.52 (m, 2H), 7.52–7.41 (m, 4H), 7.26 (d, J=8.1 Hz, 2H), 7.22 (dd, J=8.5, 1.5 Hz, 1H), 6.70 (dd, J=3.6, 1.6 Hz, 1H), 5.38–5.26 (m, 1H), 3.12 (dd, J=14.0, 5.4 Hz, 1H), 2.98 (dd, J=14.2, 9.0 Hz, 1H), 2.80–2.66 (m, 3H), 2.66–2.55 (m, 1H), 1.63–1.50 (m, 1H), 1.31–1.16 (m, 1H), 1.01–0.89 (m, 1H), 0.78 (d, J=6.4 Hz) and 0.72 (d, J=6.5 Hz) (6H total).

(7) Sodium Salt of 2-Tetrahydropyranyl 3(R)-[1(S)-(2-Furyl)carbonyl-2-(4-sulfophenyl)ethylcarbamoyl]-5-methyl-2(R or S)-(2-naphthylmethyl)hexanohydroxamate In the same manner as in Example 1(9), the title compound of Example 7(6) and O-2-tetrahydropyranylhydroxylamine were reacted. After the completion of the reaction, the reaction mixture was diluted with THF, washed successively with a 2:1 mixed solution of saturated aqueous sodium hydrogencarbonate solution and saturated brine and saturated brine, dried over anhydrous magnesium sulfate, and concentrated. The residue was triturated with diethyl ether to give the title compound (quantitatively) as a pale-yellow powder.

$^1$H-NMR (300 MHz, DMSO-d$_6$) δ 10.93 (s) and 10.90 (s) (1H total), 8.87–8.73 (m, 1H), 8.06–7.09 (m, 13H), 6.73–6.66 (m, 1H), 5.38–5.20 (m, 1H), 4.70 (s) and 4.24 (s) (1H total), 3.71–2.37 (m, 8H), 1.68–1.17 (m, 8H), 1.03–0.91 (m, 1H), 0.83–0.66 (m, 6H).

(8) Sodium Salt of 3(R)-[1(S)-(2-Furyl)carbonyl-2-(4-sulfophenyl)ethylcarbamoyl]-5-methyl-2(R or S)-(2-naphthylmethyl)hexanohydroxamic Acid The title compound of Example 7(7) was treated in the same manner as in Example 6(6) and the product was purified by reversed phase column chromatography (Chromatorex ODS DM-1020T, Fuji Silysia Chemical Ltd.; 0–25% aqueous methanol solution). The resulting product was concentrated and triturated with diethyl ether to give the title compound (yield 16%) as a white powder.

$^1$H-NMR (300 MHz, DMSO-d$_6$) δ 10.27 (br s, 1H), 8.77 (d, J=7.4Hz, 1H), 8.63 (br s, 1H), 7.99 (d, J=1.1 Hz, 1H), 7.88–7.81 (m, 2H), 7.77 (d, J=8.4 Hz, 1H), 7.53 (d, J=3.6 Hz, 1H), 7.52–7.38 (m, 5H), 7.25 (d, J=8.1 Hz, 2H), 7.14 (dd, J=8.4, 1.0 Hz, 1H), 6.69 (dd, J=3.5, 1.6 Hz, 1H), 5.38–5.22 (m, 1H), 3.12 (dd, J=14.3, 5.7 Hz, 1H), 2.97 (dd, J=14.3, 8.6 Hz, 1H), 2.90–2.76 (m, 1H), 2.70–2.58 (m, 1H), 2.58–2.37 (m, 2H), 1.52–1.38 (m, 1H), 1.35–1.16 (m, 1H), 1.00–0.88 (m, 1H), 0.78 (d, J=6.4 Hz) and 0.71 (d, J=6.5 Hz) (6H total).

Example 8

Sodium Salt of 3(R)-[1(S)-(2-Furyl)carbonyl-2-(4-sulfophenyl)ethylcarbamoyl]-5-methyl-2(R or S)-(1-naphthylmethyl)hexanohydroxamic Acid

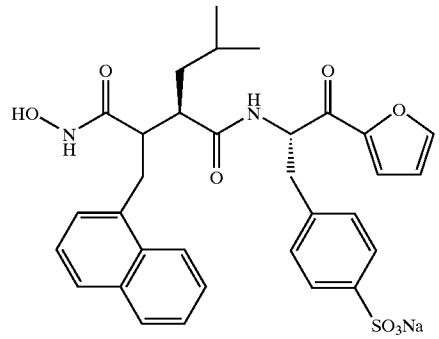

In the same manner as in Example 7(5)–(8), the title compound was obtained as a white amorphous solid from 4-tert-butoxy-2(R)-isobutyl-3(R or S)-(1-naphthylmethyl)succinic acid prepared according to the method described in JP-A-4-352757 and the title compound of Example 7(4), at an overall yield (4 steps) of 9%.

$^1$H-NMR (300 MHz, DMSO-d$_6$) δ 10.12 (s, 1H), 8.93 (d, J=7.2 Hz, 1H), 8.55 (s, 1H), 8.02–7.92 (m, 2H), 7.88 (d, J=7.6 Hz, 1H), 7.74 (d, J=8.2 Hz, 1H), 7.59–7.46 (m, 3H), 7.41 (d, J=8.1 Hz, 2H), 7.38–7.32 (m, 1H), 7.21 (d, J=8.1 Hz, 2H), 7.17 (d, J=7.0 Hz, 1H), 6.66 (dd, J=3.6, 1.6 Hz, 1H), 5.46–5.34 (m, 1H), 3.25–3.13 (m, 1H), 3.13–2.97 (m, 3H), 2.79–2.66 (m, 1H), 2.61–2.47 (m, 1H), 1.53–1.39 (m, 1H), 1.37–1.21 (m, 1H), 1.01–0.87 (m, 1H), 0.78 (d, J=6.4 Hz) and 0.72 (d, J=6.5 Hz) (6H total).

Example 9

Sodium Salt of 2(R or S)-Benzyl-3(R)-[1(S)-(2-furyl)carbonyl-2-(4-sulfophenyl)ethylcarbamoyl]-5-methylhexanohydroxamic Acid

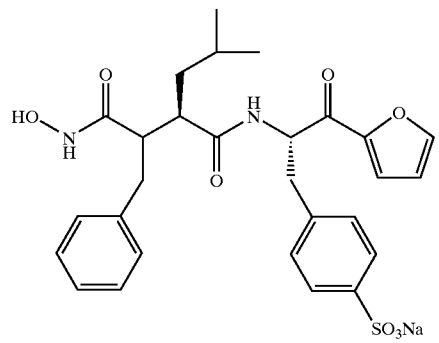

In the same manner as in Example 7(5)–(8), the title compound was obtained as a white amorphous solid from 3(R or S)-benzyl-4-tert-butoxy-2(R)-isobutylsuccinic acid prepared according to the method described in JP-A-4-352757 and JP-A-7-157470 and the title compound of Example 7(4), at an overall yield (4 steps) of 16%.

$^1$H-NMR(300 MHz, DMSO-d$_6$) δ 10.28 (br s, 1H), 8.77 (d, J=9.9 Hz, 1H), 8.66 (br s, 1H), 7.99 (d, J=1.4Hz, 1H), 7.53 (d, J=3.6 Hz, 1H), 7.46 (d, J=8.0 Hz, 2H), 7.32–7.17 (m, 4H), 7.17–7.08 (m, 1H), 6.95 (d, J=7.1 Hz, 2H), 6.69

(dd, J=3.6, 1.6Hz, 1H), 5.34–5.23 (m, 1H), 3.10 (dd, J=14.4, 5.5 Hz, 1H), 2.94 (dd, J=14.4, 8.7 Hz, 1H), 2.75–2.54 (m, 2H), 2.40–2.26 (m, 2H), 1.48–1.36 (m, 1H), 1.33–1.13 (m, 1H), 0.97–0.83 (m, 1H), 0.77 (d, J=6.4 Hz) and 0.70 (d, J=6.5 Hz) (6H total).

Example 10

Sodium Salt of 3(R)-[1(S)-(2-Furyl)carbonyl-2-(4-sulfophenyl)ethylcarbamoyl]-5-methyl-2(R or S)-phthalimidomethylhexanohydroxamic Acid

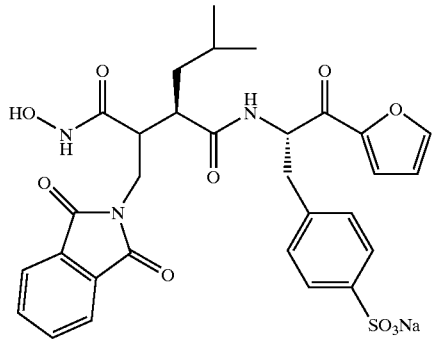

In the same manner as in Example 7(5)–(8), the title compound was obtained as a white powder from 4-tert-butoxy-2(R)-isobutyl-3(R or S)-phthalimidomethylsuccinic acid prepared according to the method described in JP-A-4-352757 and JP-A-7-157470 and the title compound of Example 7(4), at an overall yield (4 steps) of 24%.

$^1$H-NMR (300 MHz, DMSO-$d_6$) δ 10.38 (s, 1H), 8.73 (d, J=7.7 Hz, 1H), 8.61 (s, 1H), 7.98 (d, J=1.4 Hz, 1H), 7.79 (s, 4H), 7.50 (d, J=3.3 Hz, 1H), 7.39 (d, J=8.0 Hz, 2H), 7.21 (d, J=8.0 Hz, 2H), 6.68 (dd, J=3.5, 1.65 Hz, 1H), 5.25 (q, J=6.4Hz, 1H), 3.70 (dd, J=13.4, 10.20 Hz, 1H), 3.07 (dd, J=13.9, 6.18 Hz, 1H), 2.94–2.82 (m, 2H), 2.62–2.54 (m, 2H), 1.40 (m, 1H), 1.18 (m, 1H), 0.85 (t, J=12.5 Hz, 1H), 0.76 (d, J=6.5Hz, 3H), 0.68 (d, J=6.5 Hz, 3H).

Example 11

Sodium Salt of 3(R)-[1(S)-(2-Furyl)carbonyl-2-(4-sulfophenyl)ethylcarbamoyl]-5-methyl-2(R or S)-(1-oxoisoindolin-2-ylmethyl)hexanohydroxamic Acid

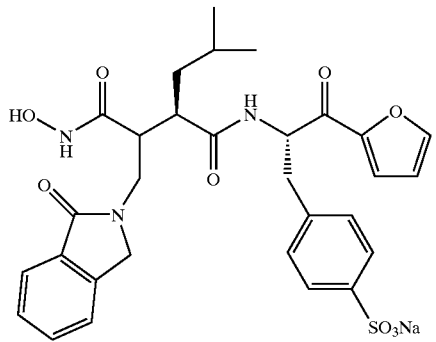

(1) Benzyl 4-tert-Butoxy-2(R)-isobutyl-3(R or S)-phthalimidomethylsuccinate

To a solution of 4-tert-butoxy-2(R)-isobutyl-3(R or S)-phthalimidomethylsuccinic acid (10.7 g, 27.4 mmol) prepared according to the method described in JP-A-4-352757 and JP-A-7-157470, benzyl alcohol (3.26 g, 30.1 mmol), methylene chloride (20 ml) and DMF (20 ml) were added successively HOBt-$H_2O$ (4.19 g, 27.4 mmol), 1-(3-dimethylaminopropyl)-3-ethylcarbodiimide hydrochloride (6.83 g, 35.6 mmol), N-methylmorpholine (9.02 ml, 82.8 mmol) and 4-dimethylaminopyridine (1.67 g, 13.7 mmol), and the mixture was stirred for 69 hr at room temperature. Ethyl acetate and diethyl ether were added to the reaction mixture and the mixture was washed successively with dilute hydrochloric acid, dilute aqueous sodium hydrogencarbonate solution and water, dried over anhydrous magnesium sulfate and concentrated. The obtained residue was purified by silica gel column chromatography (10:1 hexane-ethyl acetate) to give the title compound (12.6 g, 96%) as a transparent liquid.

$^1$H-NMR (300 MHz, DMSO-$d_6$) δ 7.97–7.80 (m, 4H), 7.42–7.27 (m, 5H), 5.18–5.02 (m, 2H), 3.94 (dd, J=13.8, 9.8 Hz, 1H), 3.59 (dd, J=13.8, 5.7 Hz, 1H), 3.20–3.01 (m, 1H), 2.80–2.67 (m, 1H), 1.70–1.40 (m, 2H), 1.30–1.10 (m, 10H), 0.92–0.70 (m, 6H).

(2) Benzyl 4-tert-Butoxy-2(R)-isobutyl-3(R or S)-thiophthalimidomethylsuccinate

A mixture of the title compound (12.2 g, 25.4 mmol) of Example 11(1), Lawesson's reagent (3.00 g, 7.41 mmol) and toluene (100 ml) was stirred for 2.5 hr under reflux with heating. Lawesson's reagent (2.66 g, 6.58 mmol) was added and the mixture was stirred for 1.5 hr under reflux with heating. The reaction mixture was cooled to room temperature and purified by silica gel column chromatography (25:1 hexane-ethyl acetate) to give the title compound (6.17 g, 49%) as a red-brown liquid.

$^1$H-NMR (300 MHz, DMSO-$d_6$) δ 8.00–7.80 (m, 4H), 7.45–7.28 (m, 5H), 5.20–5.05 (m, 2H), 4.34 (dd, J=13.7, 9.9 Hz, 1H), 3.95 (dd, J=13.7, 5.8 Hz, 1H), 3.35–3.20 (m, 1H), 2.83–2.62 (m, 1H), 1.70–1.40 (m, 2H), 1.28–1.13 (m, 10H), 0.92–0.77 (m, 6H).

(3) 4-tert-Butoxy-2(R)-isobutyl-3(R or S)-(1-oxoisoindolin-2-ylmethyl)succinic Acid To a solution of the title compound (6.03 g, 12.2 mmol) of Example 11(2) dissolved in ethanol (100 ml) was added Raney nickel (112 g) and the mixture was stirred for 2.5 hr under reflux with heating. Raney nickel (112 g) was added and the mixture was stirred for 2.5 hr under reflux with heating. The reaction mixture was filtrated and the filtrate was concentrated. The residue was dissolved in chloroform, dried over anhydrous magnesium sulfate and concentrated. The obtained residue was purified by silica gel column chromatography (1:0–5:1 chloroform-methanol) and precipitated from ethyl acetate-hexane to give the title compound (1.31 g, 29%) as a pale-yellow solid.

$^1$H-NMR (300 MHz, DMSO-$d_6$) δ 7.70–7.40 (m, 4H), 4.51–4.30 (m, 2H), 3.84 (dd, J=13.6, 10.1 Hz, 1H), 3.51 (dd, J=13.6, 5.3 Hz, 1H), 2.94–2.80 (m, 1H), 2.60–2.50 (m, 1H), 1.70–1.42 (m, 2H), 1.25 (s, 9H), 1.20–1.03 (m, 1H), 0.95–0.80 (m, 6H).

(4) Sodium Salt of 3(R)-[1(S)-(2-Furyl)carbonyl-2-(4-sulfophenyl)yl]-5-methyl-2(R or S)-(1-oxoisoindolin-2-ylmethyl)hexanohydroxamic Acid In the same manner as in Example 7(5)–(8), the title compound was obtained as a white powder from the title compound of Example 11(3) and the title compound of Example 7(4), at an over all yield (4 steps) of 23%.

$^1$H-NMR (300 MHz, DMSO-$d_6$) δ 10.52–10.41 (m, 1H), 8.80–8.69 (m, 2H), 8.00–7.90 (m, 1H), 7.70–7.38 (m, 7H), 7.19 (d, J=8.0 Hz, 2H), 6.70–6.60 (m, 1H), 5.30–5.17 (m, 1H), 4.40–4.12 (m, 2H), 3.57–3.40 (m, 1H), 3.30–3.16 (m, 1H), 3.15–3.05 (m, 1H), 3.00–2.88 (m, 1H), 2.75–2.48 (m,

2H), 1.50–1.35 (m, 1H), 1.30–1.11 (m, 1H), 1.00–0.82 (m, 1H), 0.78–0.61 (m, 6H).

The compounds of the above Examples are shown in the following Table 1.

TABLE 1

| Example No. | X | R¹ | R² | R³ | Y |
|---|---|---|---|---|---|
| 1 | H | PhtNCH$_2$ | iBu | Bn | 4-CPh 2HCl |
| 2 | H | PhtNCH$_2$ | iBu | Bn | 4-APh HCl |
| 3 | H | PhtNCH$_2$ | iBu | 4-BBn HCl | 2-Fu |
| 4 | H | PhtNCH$_2$ | iBu | Bn | 5-M-2-Fu HCl |
| 5 | H | HydCH$_2$ | iBu | 4-ABn HCl | 2-Fu |
| 6 | H | PhtNCH$_2$ | iBu | 4-NBn Na | 2-Fu |
| 7 | H | 2-NaphCH$_2$ | iBu | 4-QBn Na | 2-Fu |
| 8 | H | 2-NaphCH$_2$ | iBu | 4-QBn Na | 2-Fu |
| 9 | H | Bn | iBu | 4-QBn Na | 2-Fu |
| 10 | H | PhtNCH$_2$ | iBu | 4-QBn Na | 2-Fu |
| 11 | H | IndoCH$_2$ | iBu | 4-QBn Na | 2-Fu |

In the same manner as in Examples 1–11, the compounds of Examples 12–323 were synthesized.

TABLE 2

| Example No. | X | R¹ | R² | R³ | Y |
|---|---|---|---|---|---|
| 12 | H | PhtNCH$_2$ | iBu | 4-NH$_2$Bn HCl | 2-Fu |
| 13 | H | PhtNCH$_2$ | iBu | Bn | 4-DPh HCl |
| 14 | H | PhtNCH$_2$ | iBu | Bn | 4-EPh HCl |
| 15 | H | PhtNCH$_2$ | iBu | Bn | 4-FPh HCl |
| 16 | H | PhtNCH$_2$ | iBu | Bn | 4-GPh HCl |
| 17 | THP | PhtNCH$_2$ | iBu | Bn | 4-HPh |
| 18 | H | PhtNCH$_2$ | iBu | Bn | 4-HPh HCl |
| 19 | H | PhtNCH$_2$ | iBu | Bn | 4-IPh 2HCl |
| 20 | H | PhtNCH$_2$ | iBu | Bn | 4-BnOPh |
| 21 | H | PhtNCH$_2$ | iBu | Bn | 3-BnOPh |
| 22 | H | PhtNCH$_2$ | iBu | Bn | 3-APh HCl |
| 23 | H | PhtNCH$_2$ | iBu | Bn | 5-J-2-Fu HCl |
| 24 | THP | PhtNCH$_2$ | iBu | 4-ABn | 2-Fu |
| 25 | H | PhtNCH$_2$ | iBu | 4-ABn HCl | 2-Fu |
| 26 | H | PhtNCH$_2$ | iBu | Bn | 5-K-2-Fu |
| 27 | H | PhtNCH$_2$ | iBu | Bn | 5-L-2-Fu |
| 28 | H | PhSCH$_2$ | iBu | Bn | 4-APh HCl |
| 29 | H | 3-Ph(CH$_2$)$_3$ | iBu | Bn | 2-Fu |
| 30 | H | 3-Ph(CH$_2$)$_3$ | iBu | t-Bu | 2-Fu |
| 31 | H | 3-Ph(CH$_2$)$_3$ | iBu | 2-PyCH$_2$ HCl | 2-Fu |
| 32 | H | 3-Ph(CH$_2$)$_3$ | iBu | 3-PyCH$_2$ HCl | 2-Fu |
| 33 | H | Me | iBu | Bn | 4-APh HCl |
| 34 | THP | 3-Ph(CH$_2$)$_3$ | iBu | Bn | 4-APh |
| 35 | H | 3-Ph(CH$_2$)$_3$ | iBu | Bn | 4-APh HCl |
| 36 | THP | HydCH$_2$ | iBu | Bn | 4-APh |
| 37 | H | HydCH$_2$ | iBu | Bn | 4-APh HCl |
| 38 | THP | PhtNCH$_2$ | iBu | t-Bu | 4-APh |
| 39 | H | PhtNCH$_2$ | iBu | t-Bu | 4-APh HCl |
| 40 | H | CH$_2$=CHCH$_2$ | iBu | Bn | 4-APh HCl |
| 41 | H | CH$_2$=CHCH$_2$ | iBu | 4-ABn HCl | 2-Fu |

TABLE 3

| Example No. | X | R¹ | R² | R³ | Y |
|---|---|---|---|---|---|
| 42 | H | Me | iBu | 4-ABn HCl | 2-Fu |
| 43 | THP | 3-Ph(CH$_2$)$_3$ | iBu | 4-ABn | 2-Fu |
| 44 | H | 3-Ph(CH$_2$)$_3$ | iBu | 4-ABn HCl | 2-Fu |
| 45 | THP | 3-Ph(CH$_2$)$_3$ | iBu | Bn | 2-Thio |
| 46 | H | 3-Ph(CH$_2$)$_3$ | iBu | Bn | 2-Thio |
| 47 | H | 3-Ph(CH$_2$)$_3$ | iBu | Bn | 2-Pyrr |
| 48 | H | 3-Ph(CH$_2$)$_3$ | iBu | Bn | Ph |
| 49 | H | 3-Ph(CH$_2$)$_3$ | iBu | Bn | 4-MeOPh |
| 50 | THP | 3-Ph(CH$_2$)$_3$ | iBu | Bn | 4-Me$_2$NPh |
| 51 | H | 3-Ph(CH$_2$)$_3$ | iBu | Bn | 4-Me$_2$NPh |
| 52 | H | 3-Ph(CH$_2$)$_3$ | iBu | t-Bu | 2-Pyrr |
| 53 | THP | PhtNCH$_2$ | iBu | 4-ABn | 2-Thio |
| 54 | H | PhtNCH$_2$ | iBu | 4-ABn HCl | 2-Thio |
| 55 | H | 3-Ph(CH$_2$)$_3$ | iBu | 4-ABn HCl | 2-Thio |
| 56 | H | Me | iBu | 4-ABn HCl | 2-Thio |
| 57 | H | CH$_2$=CHCH$_2$ | iBu | 4-ABn HCl | 2-Thio |
| 58 | H | HydCH$_2$ | iBu | 4-ABn HCl | 2-Thio |
| 59 | THP | PhtNCH$_2$ | iBu | 4-ABn | 2-Pyrr |
| 60 | H | PhtNCH$_2$ | iBu | 4-ABn HCl | 2-Pyrr |
| 61 | H | 3-Ph(CH$_2$)$_3$ | iBu | 4-ABn HCl | 2-Pyrr |
| 62 | H | Me | iBu | 4-ABn HCl | 2-Pyrr |
| 63 | H | CH$_2$=CHCH$_2$ | iBu | 4-ABn HCl | 2-Pyrr |
| 64 | THP | HydCH$_2$ | iBu | 4-ABn | 2-Pyrr |
| 65 | H | HydCH$_2$ | iBu | 4-ABn HCl | 2-Pyrr |
| 66 | H | PhtNCH$_2$ | iBu | 4-ABn HCl | Ph |
| 67 | H | 3-Ph(CH$_2$)$_3$ | iBu | 4-ABn HCl | Ph |
| 68 | H | Me | iBu | 4-ABnHCl | Ph |
| 69 | H | CH$_2$=CHCH$_2$ | iBu | 4-ABn HCl | Ph |
| 70 | H | HydCH$_2$ | iBu | 4-ABn HCl | Ph |
| 71 | THP | PhtNCH$_2$ | iBu | 4-ABn | 4-MeOPh |
| 72 | H | PhtNCH$_2$ | iBu | 4-ABn HCl | 4-MeOPh |
| 73 | H | 3-Ph(CH$_2$)$_3$ | iBu | 4-ABn HCl | 4-MeOPh |
| 74 | H | Me | iBu | 4-ABn HCl | 4-MeOPh |
| 75 | H | CH$_2$=CHCH$_2$ | iBu | 4-ABn HCl | 4-MeOPh |
| 76 | H | HydCH$_2$ | iBu | 4-ABn HCl | 4-MeOPh |
| 77 | THP | PhtNCH$_2$ | iBu | 4-ABn | 4-Me$_2$NPh |
| 78 | H | PhtNCH$_2$ | iBu | 4-ABn HCl | 4-Me$_2$NPh |
| 79 | H | 3-Ph(CH$_2$)$_3$ | iBu | 4-ABn HCl | 4-Me$_2$NPh |
| 80 | H | Me | iBu | 4-ABn HCl | 4-Me$_2$NPh |
| 81 | H | CH$_2$=CHCH$_2$ | iBu | 4-ABn HCl | 4-Me$_2$NPh |
| 82 | H | HydCH$_2$ | iBu | 4-ABn HCl | 4-Me$_2$NPh |

TABLE 4

| Example No. | X | R¹ | R² | R³ | Y |
|---|---|---|---|---|---|
| 83 | THP | HydCH$_2$ | iBu | 4-NBn Na | 2-Fu |
| 84 | H | HydCH$_2$ | iBu | 4-NBn Na | 2-Fu |
| 85 | H | Me | iBu | t-Bu | 4-APh HCl |
| 86 | H | CH$_2$=CHCH$_2$ | iBu | t-Bu | 4-APh HCl |
| 87 | THP | 3-Ph(CH$_2$)$_3$ | iBu | t-Bu | 4-APh |
| 88 | H | 3-Ph(CH$_2$)$_3$ | iBu | t-Bu | 4-APh HCl |
| 89 | THP | 2-NaphCH$_2$ | iBu | t-Bu | 4-APh |
| 90 | H | 2-NaphCH$_2$ | iBu | t-Bu | 4-APh HCl |
| 91 | H | 3-Ph(CH$_2$)$_3$ | iBu | 4-NBn Na | 2-Fu |
| 92 | H | Me | iBu | 4-NBn Na | 2-Fu |
| 93 | H | CH$_2$=CHCH$_2$ | iBu | 4-NBn Na | 2-Fu |
| 94 | H | PhtNCH$_2$ | iBu | 4-NBn Na | 2-Thio |
| 95 | H | 3-Ph(CH$_2$)$_3$ | iBu | 4-NBn Na | 2-Thio |
| 96 | H | HydCH$_2$ | iBu | 4-NBn Na | 2-Thio |
| 97 | H | PhtNCH$_2$ | iBu | 4-NBn Na | 2-Pyrr |
| 98 | H | 3-Ph(CH$_2$)$_3$ | iBu | 4-NBn Na | 2-Pyrr |
| 99 | H | HydCH$_2$ | iBu | 4-NBn Na | 2-Pyrr |
| 100 | H | PhtNCH$_2$ | iBu | 4-NBn Na | Ph |
| 101 | H | 3-Ph(CH$_2$)$_3$ | iBu | 4-NBn Na | Ph |
| 102 | H | HydCH$_2$ | iBu | 4-NBn Na | Ph |
| 103 | H | PhtNCH$_2$ | iBu | 4-NBn Na | 4-MeOPh |
| 104 | H | 3-Ph(CH$_2$)$_3$ | iBu | 4-NBn Na | 4-MeOPh |
| 105 | H | HydCH$_2$ | iBu | 4-NBn Na | 4-MeOPh |
| 106 | H | PhtNCH$_2$ | iBu | 4-NBn Na | 4-Me$_2$NPh |
| 107 | H | 3-Ph(CH$_2$)$_3$ | iBu | 4-NBn Na | 4-Me$_2$NPh |
| 108 | H | HydCH$_2$ | iBu | 4-NBn Na | 4-Me$_2$NPh |
| 109 | H | PhtNCH$_2$ | iBu | 4-ABn HCl | 3-Fu |
| 110 | H | 3-Ph(CH$_2$)$_3$ | iBu | 4-ABn HCl | 3-Fu |

TABLE 4-continued

| Example No. | X | R¹ | R² | R³ | Y |
|---|---|---|---|---|---|
| 111 | THP | 2-NaphCH₂ | iBu | Bn | 4-APh |
| 112 | H | 2-NaphCH₂ | iBu | Bn | 4-APh HCl |
| 113 | H | 1-NaphCH₂ | iBu | Bn | 4-APh HCl |
| 114 | H | Bn | iBu | Bn | 4-APh HCl |
| 115 | H | IndoCH₂ | iBu | Bn | 4-APh HCl |
| 116 | THP | 2-NaphCH₂ | iBu | 4-ABn | 2-Fu |
| 117 | H | 2-NaphCH₂ | iBu | 4-ABn HCl | 2-Fu |
| 118 | H | 1-NaphCH₂ | iBu | 4-ABn HCl | 2-Fu |
| 119 | H | Bn | iBu | 4-ABn HCl | 2-Fu |
| 120 | H | IndoCH₂ | iBu | 4-ABn HCl | 2-Fu |
| 121 | THP | 2-NaphCH₂ | iBu | 4-ABn | 2-Thio |
| 122 | H | 2-NaphCH₂ | iBu | 4-ABn HCl | 2-Thio |
| 123 | H | 1-NaphCH₂ | iBu | 4-ABn HCl | 2-Thio |

TABLE 5

| Example No. | X | R¹ | R² | R³ | Y |
|---|---|---|---|---|---|
| 124 | H | Bn | iBu | 4-ABn HCl | 2-Thio |
| 125 | H | IndoCH₂ | iBu | 4-ABn HCl | 2-Thio |
| 126 | THP | 2-NaphCH₂ | iBu | 4-ABn | 2-Pyrr |
| 127 | H | 2-NaphCH₂ | iBu | 4-ABn HCl | 2-Pyrr |
| 128 | H | 1-NaphCH₂ | iBu | 4-ABn HCl | 2-Pyrr |
| 129 | H | Bn | iBu | 4-ABn HCl | 2-Pyrr |
| 130 | H | IndoCH₂ | iBu | 4-ABn HCl | 2-Pyrr |
| 131 | THP | 2-NaphCH₂ | iBu | 4-ABn | Ph |
| 132 | H | 2-NaphCH₂ | iBu | 4-ABn HCl | Ph |
| 133 | H | 1-NaphCH₂ | iBu | 4-ABn HCl | Ph |
| 134 | H | Bn | iBu | 4-ABn HCl | Ph |
| 135 | H | IndoCH₂ | iBu | 4-ABn HCl | Ph |
| 136 | THP | 2-NaphCH₂ | iBu | 4-ABn | 4-MeOPh |
| 137 | H | 2-NaphCH₂ | iBu | 4-ABn HCl | 4-MeOPh |
| 138 | H | 1-NaphCH₂ | iBu | 4-ABn HCl | 4-MeOPh |
| 139 | H | Bn | iBu | 4-ABn HCl | 4-MeOPh |
| 140 | H | IndoCH₂ | iBu | 4-ABn HCl | 4-MeOPh |
| 141 | THP | 2-NaphCH₂ | iBu | 4-ABn | 4-Me₂NPh |
| 142 | H | 2-NaphCH₂ | iBu | 4-ABn HCl | 4-Me₂NPh |
| 143 | H | 1-NaphCH₂ | iBu | 4-ABn HCl | 4-Me₂NPh |
| 144 | H | Bn | iBu | 4-ABn HCl | 4-Me₂NPh |
| 145 | H | IndoCH₂ | iBu | 4-ABn HCl | 4-Me₂NPh |
| 146 | THP | HydCH₂ | iBu | t-Bu | 4-APh |
| 147 | H | HydCH₂ | iBu | t-Bu | 4-APh HCl |
| 148 | H | 1-NaphCH₂ | iBu | t-Bu | 4-APh HCl |
| 149 | H | Bn | iBu | t-Bu | 4-APh HCl |
| 150 | H | IndoCH₂ | iBu | t-Bu | 4-APh HCl |
| 151 | THP | 2-NaphCH₂ | iBu | 4-NBn Na | 2-Fu |
| 152 | H | 2-NaphCH₂ | iBu | 4-NBn Na | 2-Fu |
| 153 | H | 1-NaphCH₂ | iBu | 4-NBn Na | 2-Fu |
| 154 | H | Bn | iBu | 4-NBn Na | 2-Fu |
| 155 | H | IndoCH₂ | iBu | 4-NBn Na | 2-Fu |
| 156 | H | Me | iBu | 4-NBn Na | 2-Thio |
| 157 | H | CH₂=CHCH₂ | iBu | 4-NBn Na | 2-Thio |
| 158 | THP | 2-NaphCH₂ | iBu | 4-NBn Na | 2-Thio |
| 159 | H | 2-NaphCH₂ | iBu | 4-NBn Na | 2-Thio |
| 160 | H | 1-NaphCH₂ | iBu | 4-NBn Na | 2-Thio |
| 161 | H | Bn | iBu | 4-NBn Na | 2-Thio |
| 162 | H | IndoCH₂ | iBu | 4-NBn Na | 2-Thio |
| 163 | H | Me | iBu | 4-NBn Na | 2-Pyrr |
| 164 | H | CH₂=CHCH₂ | iBu | 4-NBn Na | 2-Pyrr |

TABLE 6

| Example No. | X | R¹ | R² | R³ | Y |
|---|---|---|---|---|---|
| 165 | THP | 2-NaphCH₂ | iBu | 4-NBn Na | 2-Pyrr |
| 166 | H | 2-NaphCH₂ | iBu | 4-NBn Na | 2-Pyrr |
| 167 | H | 1-NaphCH₂ | iBu | 4-NBn Na | 2-Pyrr |
| 168 | H | Bn | iBu | 4-NBn Na | 2-Pyrr |
| 169 | H | IndoCH₂ | iBu | 4-NBn Na | 2-Pyrr |
| 170 | H | Me | iBu | 4-NBn Na | Ph |
| 171 | H | CH₂=CHCH₂ | iBu | 4-NBn Na | Ph |
| 172 | THP | 2-NaphCH₂ | iBu | 4-NBn Na | Ph |

TABLE 6-continued

| Example No. | X | R¹ | R² | R³ | Y |
|---|---|---|---|---|---|
| 173 | H | 2-NaphCH₂ | iBu | 4-NBn Na | Ph |
| 174 | H | 1-NaphCH₂ | iBu | 4-NBn Na | Ph |
| 175 | H | Bn | iBu | 4-NBn Na | Ph |
| 176 | H | IndoCH₂ | iBu | 4-NBn Na | Ph |
| 177 | H | Me | iBu | 4-NBn Na | 4-MeOPh |
| 178 | H | CH₂=CHCH₂ | iBu | 4-NBn Na | 4-MeOPh |
| 179 | THP | 2-NaphCH₂ | iBu | 4-NBn Na | 4-MeOPh |
| 180 | H | 2-NaphCH₂ | iBu | 4-NBn Na | 4-MeOPh |
| 181 | H | 1-NaphCH₂ | iBu | 4-NBn Na | 4-MeOPh |
| 182 | H | Bn | iBu | 4-NBn Na | 4-MeOPh |
| 183 | H | IndoCH₂ | iBu | 4-NBn Na | 4-MeOPh |
| 184 | H | Me | iBu | 4-NBn Na | 4-Me₂NPh |
| 185 | H | CH₂=CHCH₂ | iBu | 4-NBn Na | 4-Me₂NPh |
| 186 | THP | 2-NaphCH₂ | iBu | 4-NBn Na | 4-Me₂NPh |
| 187 | H | 2-NaphCH₂ | iBu | 4-NBn Na | 4-Me₂NPh |
| 188 | H | 1-NaphCH₂ | iBu | 4-NBn Na | 4-Me₂NPh |
| 189 | H | Bn | iBu | 4-NBn Na | 4-Me₂NPh |
| 190 | H | IndoCH₂ | iBu | 4-NBn Na | 4-Me₂NPh |
| 191 | H | 3-Ph(CH₂)₃ | iBu | 4-QBn Na | 2-Fu |
| 192 | H | Me | iBu | 4-QBn Na | 2-Fu |
| 193 | H | CH₂=CHCH₂ | iBu | 4-QBn Na | 2-Fu |
| 194 | H | HydCH₂ | iBu | 4-QBn Na | 2-Fu |
| 195 | H | PhtNCH₂ | iBu | 4-QBn Na | 2-Thio |
| 196 | H | 3-Ph(CH₂)₃ | iBu | 4-QBn Na | 2-Thio |
| 197 | H | Me | iBu | 4-QBn Na | 2-Thio |
| 198 | H | CH₂=CHCH₂ | iBu | 4-QBn Na | 2-Thio |
| 199 | H | HydCH₂ | iBu | 4-QBn Na | 2-Thio |
| 200 | THP | 2-NaphCH₂ | iBu | 4-QBn Na | 2-Thio |
| 201 | H | 2-NaphCH₂ | iBu | 4-QBn Na | 2-Thio |
| 202 | H | 1-NaphCH₂ | iBu | 4-QBn Na | 2-Thio |
| 203 | H | Bn | iBu | 4-QBn Na | 2-Thio |
| 204 | H | IndoCH₂ | iBu | 4-QBn Na | 2-Thio |
| 205 | H | PhtNCH₂ | iBu | 4-QBn Na | 2-Pyrr |

TABLE 7

| Example No. | X | R¹ | R² | R³ | Y |
|---|---|---|---|---|---|
| 206 | H | 3-Ph(CH₂)₃ | iBu | 4-QBn Na | 2-Pyrr |
| 207 | H | Me | iBu | 4-QBn Na | 2-Pyrr |
| 208 | H | CH₂=CHCH₂ | iBu | 4-QBn Na | 2-Pyrr |
| 209 | H | HydCH₂ | iBu | 4-QBn Na | 2-Pyrr |
| 210 | THP | 2-NaphCH₂ | iBu | 4-QBn Na | 2-Pyrr |
| 211 | H | 2-NaphCH₂ | iBu | 4-QBn Na | 2-Pyrr |
| 212 | H | 1-NaphCH₂ | iBu | 4-QBn Na | 2-Pyrr |
| 213 | H | Bn | iBu | 4-QBn Na | 2-Pyrr |
| 214 | H | IndoCH₂ | iBu | 4-QBn Na | 2-Pyrr |
| 215 | H | PhtNCH₂ | iBu | 4-QBn Na | Ph |
| 216 | H | 3-Ph(CH₂)₃ | iBu | 4-QBn Na | Ph |
| 217 | H | Me | iBu | 4-QBn Na | Ph |
| 218 | H | CH₂=CHCH₂ | iBu | 4-QBn Na | Ph |
| 219 | H | HydCH₂ | iBu | 4-QBn Na | Ph |
| 220 | THP | 2-NaphCH₂ | iBu | 4-QBn Na | Ph |
| 221 | H | 2-NaphCH₂ | iBu | 4-QBn Na | Ph |
| 222 | H | 1-NaphCH₂ | iBu | 4-QBn Na | Ph |
| 223 | H | Bn | iBu | 4-QBn Na | Ph |
| 224 | H | IndoCH₂ | iBu | 4-QBn Na | Ph |
| 225 | H | PhtNCH₂ | iBu | 4-QBn Na | 4-MeOPh |
| 226 | H | 3-Ph(CH₂)₃ | iBu | 4-QBn Na | 4-MeOPh |
| 227 | H | Me | iBu | 4-QBn Na | 4-MeOPh |
| 228 | H | CH₂=CHCH₂ | iBu | 4-QBn Na | 4-MeOPh |
| 229 | H | HydCH₂ | iBu | 4-QBn Na | 4-MeOPh |
| 230 | THP | 2-NaphCH₂ | iBu | 4-QBn Na | 4-MeOPh |
| 231 | H | 2-NaphCH₂ | iBu | 4-QBn Na | 4-MeOPh |
| 232 | H | 1-NaphCH₂ | iBu | 4-QBn Na | 4-MeOPh |
| 233 | H | Bn | iBu | 4-QBn Na | 4-MeOPh |
| 234 | H | IndoCH₂ | iBu | 4-QBn Na | 4-MeOPh |
| 235 | H | PhtNCH₂ | iBu | 4-QBn Na | 4-Me₂NPh |
| 236 | H | 3-Ph(CH₂)₃ | iBu | 4-QBn Na | 4-Me₂NPh |
| 237 | H | Me | iBu | 4-QBn Na | 4-Me₂NPh |
| 238 | H | CH₂=CHCH₂ | iBu | 4-QBn Na | 4-Me₂NPh |
| 239 | H | HydCH₂ | iBu | 4-QBn Na | 4-Me₂NPh |
| 240 | THP | 2-NaphCH₂ | iBu | 4-QBn Na | 4-Me₂NPh |
| 241 | H | 2-NaphCH₂ | iBu | 4-QBn Na | 4-Me₂NPh |

TABLE 7-continued

| Example No. | X | R¹ | R² | R³ | Y |
|---|---|---|---|---|---|
| 242 | H | 1-NaphCH₂ | iBu | 4-QBn Na | 4-Me₂NPh |
| 243 | H | Bn | iBu | 4-QBn Na | 4-Me₂NPh |
| 244 | H | IndoCH₂ | iBu | 4-QBn Na | 4-Me₂NPh |
| 245 | H | HydCH₂ | iBu | Bn | 5-L-2-Fu |
| 246 | H | 3-Ph(CH₂)₃ | iBu | Bn | 5-L-2-Fu |

TABLE 8

| Example No. | X | R¹ | R² | R³ | Y |
|---|---|---|---|---|---|
| 247 | H | HydCH₂ | iBu | 4-ABn HCl | 3-Fu |
| 248 | H | 2-NaphCH₂ | iBu | 4-ABn HCl | 3-Fu |
| 249 | H | IndoCH₂ | iBu | 4-ABn HCl | 3-Fu |
| 250 | H | PhtNCH₂ | iBu | 4-NBn Na | 3-Fu |
| 251 | H | 3-Ph(CH₂)₃ | iBu | 4-NBn Na | 3-Fu |
| 252 | H | HydCH₂ | iBu | 4-NBn Na | 3-Fu |
| 253 | H | 2-NaphCH₂ | iBu | 4-NBn Na | 3-Fu |
| 254 | H | IndoCH₂ | iBu | 4-NBn Na | 3-Fu |
| 255 | H | PhtNCH₂ | iBu | 4-QBn Na | 3-Fu |
| 256 | H | 3-Ph(CH₂)₃ | iBu | 4-QBn Na | 3-Fu |
| 257 | H | HydCH₂ | iBu | 4-QBn Na | 3-Fu |
| 258 | H | 2-NaphCH₂ | iBu | 4-QBn Na | 3-Fu |
| 259 | H | IndoCH₂ | iBu | 4-QBn Na | 3-Fu |
| 260 | H | PhtNCH₂ | iBu | 4-ABn HCl | 2-Thia |
| 261 | H | 2-NaphCH₂ | iBu | 4-ABn HCl | 2-Thia |
| 262 | H | IndoCH₂ | iBu | 4-ABn HCl | 2-Thia |
| 263 | H | PhtNCH₂ | iBu | 4-NBn Na | 2-Thia |
| 264 | H | 2-NaphCH₂ | iBu | 4-NBn Na | 2-Thia |
| 265 | H | IndoCH₂ | iBu | 4-NBn Na | 2-Thia |
| 266 | H | PhtNCH₂ | iBu | 4-QBn Na | 2-Thia |
| 267 | H | 2-NaphCH₂ | iBu | 4-QBn Na | 2-Thia |
| 268 | H | IndoCH₂ | iBu | 4-QBn Na | 2-Thia |
| 269 | H | PhtNCH₂ | iBu | 4-ABn HCl | 3-Py |
| 270 | H | 3-Ph(CH₂)₃ | iBu | 4-ABn HCl | 3-Py |
| 271 | H | HydCH₂ | iBu | 4-ABn HCl | 3-Py |
| 272 | H | 2-NaphCH₂ | iBu | 4-ABn HCl | 3-Py |
| 273 | H | IndoCH₂ | iBu | 4-ABn HCl | 3-Py |
| 274 | H | PhtNCH₂ | iBu | 4-NBn Na | 3-Py |
| 275 | H | 3-Ph(CH₂)₃ | iBu | 4-NBn Na | 3-Py |
| 276 | H | HydCH₂ | iBu | 4-NBn Na | 3-Py |
| 277 | H | 2-NaphCH₂ | iBu | 4-NBn Na | 3-Py |
| 278 | H | IndoCH₂ | iBu | 4-NBn Na | 3-Py |
| 279 | H | PhtNCH₂ | iBu | 4-QBn Na | 3-Py |
| 280 | H | 3-Ph(CH₂)₃ | iBu | 4-QBn Na | 3-Py |
| 281 | H | HydCH₂ | iBu | 4-QBn Na | 3-Py |
| 282 | H | 2-NaphCH₂ | iBu | 4-QBn Na | 3-Py |
| 283 | H | IndoCH₂ | iBu | 4-QBn Na | 3-Py |
| 284 | H | PhtNCH₂ | iBu | Bn | 4-UPh Na |
| 285 | H | 3-Ph(CH₂)₃ | iBu | Bn | 4-UPh Na |
| 286 | H | HydCH₂ | iBu | Bn | 4-UPh Na |
| 287 | H | 2-NaphCH₂ | iBu | Bn | 4-UPh Na |

TABLE 9

| Example No. | X | R¹ | R² | R³ | Y |
|---|---|---|---|---|---|
| 288 | H | IndoCH₂ | iBu | Bn | 4-UPh Na |
| 289 | H | PhtNCH₂ | iBu | Bn | 4-VPh Na |
| 290 | H | 3-Ph(CH₂)₃ | iBu | Bn | 4-VPh Na |
| 291 | H | HydCH₂ | iBu | Bn | 4-VPh Na |
| 292 | H | 2-NaphCH₂ | iBu | Bn | 4-VPh Na |
| 293 | H | IndoCH₂ | iBu | Bn | 4-VPh Na |
| 294 | H | PhtNCH₂ | iBu | Bn | 4-WPh Na |
| 295 | H | 3-Ph(CH₂)₃ | iBu | Bn | 4-WPh Na |
| 296 | H | HydCH₂ | iBu | Bn | 4-WPh Na |
| 297 | H | 2-NaphCH₂ | iBu | Bn | 4-WPh Na |
| 298 | H | IndoCH₂ | iBu | Bn | 4-WPh Na |
| 299 | H | PhtNCH₂ | iBu | Bn | 5-X-2-Fu Na |
| 300 | H | 3-Ph(CH₂)₃ | iBu | Bn | 5-X-2-Fu Na |
| 301 | H | HydCH₂ | iBu | Bn | 5-X-2-Fu Na |
| 302 | H | 2-NaphCH₂ | iBu | Bn | 5-X-2-Fu Na |
| 303 | H | IndoCH₂ | iBu | Bn | 5-X-2-Fu Na |

TABLE 9-continued

| Example No. | X | R¹ | R² | R³ | Y |
|---|---|---|---|---|---|
| 304 | H | PhtNCH₂ | iBu | Bn | 5-Y-2-Fu Na |
| 305 | H | 3-Ph(CH₂)₃ | iBu | Bn | 5-Y-2-Fu Na |
| 306 | H | HydCH₂ | iBu | Bn | 5-Y-2-Fu Na |
| 307 | H | 2-NaphCH₂ | iBu | Bn | 5-Y-2-Fu Na |
| 308 | H | IndoCH₂ | iBu | Bn | 5-Y-2-Fu Na |
| 309 | H | PhtNCH₂ | iBu | Bn | 5-Z-2-Fu Na |
| 310 | H | 3-Ph(CH₂)₃ | iBu | Bn | 5-Z-2-Fu Na |
| 311 | H | HydCH₂ | iBu | Bn | 5-Z-2-Fu Na |
| 312 | H | 2-NaphCH₂ | iBu | Bn | 5-Z-2-Fu Na |
| 313 | H | IndoCH₂ | iBu | Bn | 5-Z-2-Fu Na |

TABLE 10

| Example No. | X | R¹ | R² | R³ | Y |
|---|---|---|---|---|---|
| 314 | H | PhtNCH₂ | iBu | 4-UBn Na | 2-Fu |
| 315 | H | 3-Ph(CH₂)₃ | iBu | 4-UBn Na | 2-Fu |
| 316 | H | HydCH₂ | iBu | 4-UBn Na | 2-Fu |
| 317 | H | 2-NaphCH₂ | iBu | 4-UBn Na | 2-Fu |
| 318 | H | IndoCH₂ | iBu | 4-UBn Na | 2-Fu |
| 319 | H | PhtNCH₂ | iBu | 4-VBn Na | 2-Fu |
| 320 | H | 3-Ph(CH₂)₃ | iBu | 4-VBn Na | 2-Fu |
| 321 | H | HydCH₂ | iBu | 4-VBn Na | 2-Fu |
| 322 | H | 2-NaphCH₂ | iBu | 4-VBn Na | 2-Fu |
| 323 | H | IndoCH₂ | iBu | 4-VBn Na | 2-Fu |

Me:methyl, iBu:isobutyl, tBu:tert-butyl, Bn:benzyl, Ph:phenyl, THP:2-tetrahydropyranyl, PhtNCH₂:phthalimidomethyl, HydCH₂:(2,5-dioxo-3,4,4-trimethyl-1-imidazolidinyl)methyl, 1-NaphCH₂:1-naphthylmethyl, 2-NaphCH₂:2-naphthylmethyl, IndoCH₂:1-oxoisoindolin-2-ylmethyl, PhSCH₂:phenylthiomethyl, 3-Ph(CH₂)₃:3-phenylpropyl, CH₂=CHCH₂:2-propenyl, 4-NH₂Bn HCl:4-aminobenzyl hydrochloride, 4-ABn HCl:4-(2-dimethylaminoethoxy)benzyl hydrochloride, 4-ABn:4-(2-dimethylaminoethoxy)benzyl, 4-BBn HCl:4-guanidinobenzyl hydrochloride, 4-NBn Na:4-(hydroxysulfonyloxy)benzyl sodium salt, 4-QBn Na:4-sulfobenzyl sodium salt, 2-PyCH₂ HCl:2-pyridylmethyl hydrochloride, 3-PyCH₂ HCl:3-pyridylmethyl hydrochloride, 3-BnOPh:3-benzyloxyphenyl, 3-APh HCl:3-(2-dimethylaminoethoxy)phenyl hydrochloride, 4-BnOPh:4-benzyloxyphenyl, 4-MeOPh:4-methoxyphenyl, 4-Me₂NPh:4-dimethylaminophenyl, 4-APh HCl:4-(2-dimethylaminoethoxy)phenyl hydrochloride, 4-APh:4-(2-dimethylaminoethoxy)phenyl, 4-CPh 2HCl:4-[2-[1-(4-methyl)piperazinyl]ethoxy]phenyl dihydrochloride, 4-DPh HCl:4-(2-morpholinoethoxy)phenyl hydrochloride, 4-EPh HCl:4-[2-(2-pyridyl)ethoxy]phenyl hydrochloride, 4-FPh HCl:4-(3-dimethylaminopropoxy)phenyl hydrochloride, 4-GPh HCl:4-[2-(1-pyrrolidinyl)ethoxy]phenyl hydrochloride, 4-HPh HCl:4-(2-piperidinoethoxy)phenyl hydrochloride, 4-HPh:4-(2-piperidinoethoxy)phenyl, 4-IPh 2HCl:4-[2-[2-[1-(4-methyl)piperazinyl]ethoxy]ethoxy]phenyl dihydrochloride, 2-Fu:2-furyl, 5-J-2-Fu HCl:2-(5-dimethylaminomethyl)furyl hydrochloride, 5-K-2-Fu:2-(5-benzyloxymethyl)furyl, 5-L-2-Fu:2-(5-hydroxymethyl)furyl, 5-M-2-Fu HCl:2-[5-(2-dimethylaminoethoxy)methyl]furyl hydrochloride, 3-Fu:3-furyl, 2-Thio:2-thienyl, 2-Pyrr:2-pyrrolyl, 2-Thia:2-thiazolyl, 3-Py:3-pyridyl, 4-UPh Na:4-[2-(hydroxysulfonyloxy)ethoxy]phenyl sodium salt, 4-VPh Na:4-(2-sulfoethoxy)phenyl sodium salt, 4-WPh Na:4-(carboxymethoxy)phenyl sodium salt, 5-X-2-Fu Na:2-[5-[2-(hydroxysulfonyloxy)ethoxy]methyl]furyl sodium salt, 5-Y-2-Fu Na:2-[5-(2-sulfoethoxy)methyl]furyl sodium salt, 5-Z-2-Fu Na:2-(5-carboxymethoxy)furyl sodium salt, 4-UBn Na:4-[2-(hydroxysulfonyloxy)ethoxy]benzyl sodium salt, 4-VBn Na:4-(2-sulfoethoxy)benzyl sodium salt.

Of these compounds, the $^1$H-NMR spectrum data of the representative compounds are shown in the following.

Example 12

3(R)-[2-(4-Aminophenyl)-1(S)-(2-furyl)carbonyl]ethylcarbamoyl-5-methyl-2(R or S)-phthalimidomethylhexanohydroxamic Acid Hydrochloride $^1$H-NMR (300 MHz, DMSO-d$_6$) δ 10.39 (br s, 1H), 8.74 (d, J=8.0 Hz, 1H), 8.05–7.95 (m, 1H), 7.90–7.75 (m, 4H), 7.55 (d, J=3.6 Hz, 1H), 7.37 (d, J=8.0 Hz, 2H), 7.07 (d, J=8.0 Hz, 2H), 6.75–6.68 (m, 1H), 5.35–5.22 (m, 1H), 3.75–3.60 (m, 1H), 3.09 (dd, J=13.9, 5.3 Hz, 1H), 2.92 (dd, J=13.9, 9.4 Hz, 1H), 2.86–2.75 (m, 1H), 2.68–2.50 (m, 2H), 1.47–1.32 (m, 1H), 1.25–1.10 (m, 1H), 0.90–0.75 (m, 1H), 0.77 (d, J=6.4 Hz, 3H), 0.68 (d, J=6.4 Hz, 3H).

Example 17

2-Tetrahydropyranyl 5-Methyl-3(R)-[2-phenyl-1(S)-[4-(2-piperidinoethoxy)benzoyl]]ethylcarbamoyl-2(R or S)-phthalimidomethylhexanohydroxamate $^1$H-NMR (300 MHz, DMSO-d$_6$) δ 11.00–10.80 (m, 1H), 8.70–8.60 (m, 1H), 7.99 (dd, J=8.7, 2.0 Hz, 2H), 7.90–7.78 (m, 4H), 7.35 (d, J=7.5 Hz, 2H), 7.09 (t, J=7.6 Hz, 2H), 7.01 (d, J=8.7 Hz, 2H), 6.81 (t, J=7.4 Hz, 1H), 5.70–5.55 (m, 1H), 4.55–4.30 (m, 1H), 4.10 (t, J=5.3 Hz, 2H), 3.75–3.25 (m, 2H), 3.12 (dd, J=14.0, 4.5 Hz, 1H), 3.08–2.65 (m, 1H), 2.87 (dd, J=14.0, 10.7 Hz, 1H), 2.65–2.30 (m, 8H), 2.20–2.05 (m, 1H), 1.60–1.20 (m, 13H), 1.10–0.90 (m, 1H), 0.85–0.70 (m, 1H), 0.63 (d, J=6.4 Hz, 3H), 0.60 (d, J=6.4 Hz, 3H).

Example 18

5-Methyl-3(R)-[2-phenyl-1(S)-[4-(2-piperidinoethoxy)benzoyl]]-ethylcarbamoyl-2(R or S)-phthalimidomethylhexanohydroxamic Acid Hydrochloride $^1$H-NMR (300 MHz, DMSO-d$_6$) δ 10.33 (br s, 1H), 10.10–9.90 (br, 1H), 8.70–8.50 (br, 1H), 8.64 (d, J=8.6 Hz, 1H), 8.06 (d, J=8.9 Hz, 2H), 7.95–7.80 (m, 4H), 7.36 (d, J=7.4 Hz, 2H), 7.10 (d, J=8.9 Hz, 2H), 7.08 (t, J=7.6 Hz, 2H), 6.78 (t, J=7.2 Hz, 1H), 5.75–5.60 (m, 1H), 4.55–4.40 (m, 2H), 3.60–3.25 (m, 5H), 3.11 (dd, J=14.2, 4.4 Hz, 1H), 3.10–2.90 (m, 2H), 2.86 (dd, J=14.2, 10.4 Hz, 1H), 2.60–2.40 (m, 2H), 2.25–2.12 (m, 1H), 1.90–1.63 (m, 5H), 1.50–1.25 (m, 2H), 1.10–0.90 (m, 1H), 0.85–0.70 (m, 1H), 0.68 (d, J=6.4 Hz, 3H), 0.62 (d, J=6.4 Hz, 3H).

Example 23

3(R)-[1(S)-[2-(5-Dimethylaminomethyl)furyl]carbonyl-2-phenyl]ethylcarbamoyl-5-methyl-2(R or S)-phthalimidomethylhexanohydroxamic Acid Hydrochloride $^1$H-NMR (300 MHz, DMSO-d$_6$) δ 10.65–10.40 (br, 1H), 10.34 (br s, 1H), 8.70 (d, J=8.7 Hz, 1H), 8.70–8.50 (br, 1H), 7.90–7.80 (m, 4H), 7.68 (d, J=3.6 Hz, 1H), 7.37 (d, J=7.2 Hz, 2H), 7.09 (t, J=7.7 Hz, 2H), 6.95 (d, J=3.6 Hz, 1H), 6.79 (t, J=7.4 Hz, 1H), 5.48–5.35 (m, 1H), 4.50 (s, 2H), 3.55–3.25 (m, 1H), 3.14 (dd, J=13.5, 4.2 Hz, 1H), 2.87 (dd, J=13.5, 11.1 Hz, 1H), 2.76 (s, 6H), 2.65–2.40 (m, 2H), 2.25 (dd, J=13.2, 3.9 Hz, 1H), 1.46–1.32 (m, 1H), 1.25–1.10 (m, 1H), 0.90–0.75 (m, 1H), 0.78 (d, J=6.5 Hz, 3H), 0.69 (d, J=6.5 Hz, 3H).

Example 24

2-Tetrahydropyranyl 3(R)-[2-[4-(2-Dimethylaminoethoxy)phenyl]-1(S)-(2-furyl)carbonyl]ethylcarbamoyl-5-methyl-2(R or S)-phthalimidomethylhexanohydroxamate $^1$H-NMR (300 MHz, DMSO-d$_6$) δ 10.91–10.78 (m, 1H), 8.70–8.50 (m, 1H), 8.10–8.00 (m, 1H), 7.90–7.80 (m, 4H), 7.80–7.65 (m, 1H), 7.32–7.18 (m, 2H), 6.80–6.70 (m, 1H), 6.63–6.50 (m, 2H), 5.50–5.33 (m, 1H), 4.60–4.30 (m, 1H), 3.74–3.40 (m, 4H), 3.10–2.94 (m, 1H), 2.80–2.20 (m, 4H), 1.93 (s, 6H), 1.83 (t, J=6.1 Hz, 2H), 1.60–1.00 (m, 8H), 0.85–0.60 (m, 7H).

Example 25

3(R)-[2-[4-(2-Dimethylaminoethoxy)phenyl]-1(S)-(2-furyl)carbonyl]ethylcarbamoyl-5-methyl-2(R or S)-phthalimidomethylhexanohydroxamic Acid Hydrochloride $^1$H-NMR (300 MHz, DMSO-d$_6$) δ 10.38–10.26 (m, 1H), 10.05 (br s, 1H), 8.90–8.37 (m, 2H), 8.10–8.02 (m, 1H), 7.92–7.80 (m, 4H), 7.70–7.60 (m, 1H), 7.30 (d, J=8.6 Hz, 2H), 6.74 (dd, J=3.6, 1.6 Hz, 1H), 6.71 (d, J=8.6 Hz, 2H), 5.45–5.30 (m, 1H), 3.86 (t, J=5.1 Hz, 2H), 3.50–3.40 (m, 1H), 3.05 (dd, J=13.9, 4.7 Hz, 1H), 2.95–2.39 (m, 11H), 2.25–2.11 (m, 1H), 1.48–1.30 (m, 1H), 1.22–1.02 (m, 1H), 0.88–0.59 (m, 7H).

Example 27

3(R)-[1(S)-[2-(5-Hydroxymethyl)furyl]carbonyl-2-phenyl]ethylcarbamoyl-5-methyl-2(R or S)-phthalimidomethylhexanohydroxamic Acid $^1$H-NMR (300 MHz, DMSO-d$_6$) δ 10.33 (br s, 1H), 8.65 (d, J=8.3 Hz, 1H), 8.61 (br s, 1H), 7.90–7.80 (m, 4H), 7.60 (d, J=3.5 Hz, 1H), 7.36 (d, J=7.4 Hz, 2H), 7.08 (t, J=7.6 Hz, 2H), 6.78 (t, J=7.4 Hz, 1H), 6.54 (t, J=3.5 Hz, 1H), 5.54 (t, J=5.8 Hz, 1H), 5.42–5.30 (m, 1H), 4.50 (d, J=5.8 Hz, 2H), 3.47 (dd, J=13.2, 10.9 Hz, 1H), 3.09 (dd, J=13.8, 4.4 Hz, 1H), 2.85 (dd, J=13.8, 10.5 Hz, 1H), 2.60–2.40 (m, 2H), 2.25 (dd, J=13.2, 3.9 Hz, 1H), 1.48–1.35 (m, 1H), 1.30–1.10 (m, 1H), 0.90–0.75 (m, 1H), 0.78 (d, J=6.5 Hz, 3H), 0.69 (d, J=6.5 Hz, 3H).

Example 33

2(R or S),5-Dimethyl-3(R)-[1(S)-[4-(2-dimethylaminoethoxy)benzoyl]-2-phenyl]ethylcarbamoylhexanohydroxamic Acid Hydrochloride $^1$H-NMR (300 MHz, DMSO-d$_6$) δ 10.40–10.30 (m, 1H), 10.02 (br s, 1H), 8.52 (d, J=8.3 Hz, 1H), 8.03 (d, J=8.8 Hz, 2H), 7.39–7.13 (m, 5H), 7.11 (d, J=8.8 Hz, 2H), 5.65–5.48 (m, 1H), 4.50–4.35 (m, 2H), 3.60–3.48 (m, 2H), 3.12–3.02 (m, 1H), 2.92–2.78 (m, 7H), 2.42–2.23 (m, 1H), 2.05–1.90 (m 1H), 1.36–1.20 (m, 1H), 1.07–0.92 (m, 1H), 0.80–0.40 (m, 10H).

Example 34

2-Tetrahydropyranyl 3(R)-[1(S)-[4-(2-Dimethylaminoethoxy)benzoyl]-2-phenyl]ethylcarbamoyl-5-methyl-2(R or S)-(3-phenylpropyl)hexanohydroxamate $^1$H-NMR (300 MHz, DMSO-d$_6$) δ 11.10–11.00 (m, 1H), 8.60–8.50 (m, 1H), 8.02–7.90 (m, 2H), 7.40–6.98 (m, 12H), 5.65–5.50 (m, 1H), 4.85–4.70 (m, 1H), 4.20–4.07 (m, 2H), 4.00–3.80 (m, 1H), 3.50–3.32 (m, 1H), 3.17–3.00 (m, 1H), 2.90–2.76 (m, 1H), 2.70–2.58 (m, 2H), 2.43–1.94 (m, 10H), 1.70–1.39 (m, 6H), 1.39–1.08 (m, 5H), 1.08–0.90 (m, 1H), 0.88–0.72 (m, 1H), 0.70–0.50 (m, 6H).

Example 35

3(R)-[1(S)-[4-(2-Dimethylaminoethoxy)benzoyl]-2-phenyl]ethylcarbamoyl-5-methyl-2(R or S)-(3-phenylpropyl)hexanohydroxamic Acid Hydrochloride $^1$H-NMR (300 MHz, DMSO-d$_6$) δ 10.46–10.38 (m, 1H), 10.15–9.98 (m, 1H), 8.54 (d, J=8.3 Hz, 1H), 8.04 (d, J=8.8 Hz, 2H), 7.40–7.00 (m, 12H), 5.65–5.50 (m, 1H), 4.50–4.31 (t, J=4.9 Hz, 2H), 3.60–3.47 (m, 2H), 3.10–2.98 (m, 1H), 2.90–2.73 (m, 7H), 2.40–1.85 (m, 4H), 1.36–0.90 (m, 6H), 0.83–0.55 (m, 7H).

Example 36

2-Tetrahydropyranyl 3(R)-[1(S)-[4-(2-Dimethylaminoethoxy)benzoyl]-2-phenyl]ethylcarbamoyl-5-methyl-2(R or S)-(2,5-dioxo-3,4,4-trimethyl-1-imidazolidinyl)methylhexanohydroxamate $^1$H-NMR (300 MHz, DMSO-d$_6$) δ 11.00–10.80 (m, 1H), 8.65–8.50 (m, 1H), 8.08–7.95 (m, 2H), 7.40–6.90 (m, 7H), 5.70–5.45 (m, 1H), 4.80–4.55 (m, 1H), 4.20–4.05 (m, 2H), 3.95–3.70 (m, 1H), 3.50–3.20 (m, 2H), 3.10 (dd, J=13.9, 4.2 Hz, 1H), 2.92–2.78 (m, 1H), 2.86 (s, 3H), 2.69–2.60 (m, 2H), 2.55–2.30 (m, 2H), 2.21 (s, 6H), 2.08–1.90 (m, 1H), 1.70–1.15 (m, 7H), 1.24 (s, 6H), 1.07–0.89 (m, 1H), 0.80–0.65 (m, 1H), 0.63 (d, J=6.5 Hz, 3H), 0.60 (d, J=6.5 Hz, 3H).

Example 37

3(R)-[1(S)-[4-(2-Dimethylaminoethoxy)benzoyl]-2-phenyl]ethylcarbamoyl-5-methyl-2(R or S)-(2,5-dioxo-3,4,4-trimethyl-1-imidazolidinyl)methylhexanohydroxamic Acid Hydrochloride $^1$H-NMR (500 MHz, DMSO-d$_6$) δ 10.31 (br s, 1H), 10.00–9.90 (br, 1H), 8.64 (br s, 1H), 8.57 (d, J=8.6 Hz, 1H), 8.06 (d, J=8.9 Hz, 2H), 7.35 (d, J=7.2 Hz, 2H), 7.13 (t, J=7.5 Hz, 2H), 7.11 (d, J=8.9 Hz, 2H), 6.98 (t, J=7.4 Hz, 1H), 5.70–5.60 (m, 1H), 4.50–4.35 (m, 2H), 3.60–3.45 (m, 2H), 3.35–3.20 (m, 1H), 3.29 (s, 6H), 2.90–2.80 (m, 1H), 2.76 (s, 3H), 2.55–2.40 (m, 2H), 1.99 (dd, J=13.4, 3.6 Hz, 1H), 1.40–1.30 (m, 1H), 1.24 (s, 3H), 1.23 (s, 3H), 1.05–0.95 (m, 1H), 0.80–0.70 (m, 1H), 0.66 (d, J=6.5 Hz, 3H), 0.61 (d, J=6.5 Hz, 3H).

Example 38

2-Tetrahydropyranyl 3(R)-[2,2-Dimethyl-1(S)-[4-(2-dimethylaminoethoxy)benzoyl]]propylcarbamoyl-5-methyl-2(R or S)-phthalimidomethylhexanohydroxamate $^1$H-NMR (300 MHz, DMSO-d$_6$) δ 11.10–10.93 (m, 1H), 8.41–8.30 (m, 1H), 8.00–7.90 (m, 2H), 7.90–7.75 (m, 4H), 7.10–7.00 (m, 2H), 5.35–5.20 (m, 1H), 4.65–4.40 (m, 1H), 4.20–4.05 (m, 2H), 4.05–2.57 (m, 8H), 2.30–2.17 (m, 6H), 1.66–1.23 (m, 7H), 1.23–1.00 (m, 1H), 1.00–0.57 (m, 16H).

Example 39

3(R)-[2,2-Dimethyl-1(S)-[4-(2-dimethylaminoethoxy)benzoyl]]propylcarbamoyl-5-methyl-2(R or S)-phthalimidomethylhexanohydroxamic Acid Hydrochloride $^1$H-NMR (300 MHz, DMSO-d$_6$) δ 10.50–10.37 (m, 1H), 9.60 (br s, 1H), 8.72–8.60 (m, 1H), 8.40–8.27 (m, 1H), 7.97 (d, J=8.8 Hz, 2H), 7.87–7.75 (m, 4H), 7.09 (d, J=8.8 Hz, 2H), 5.30–5.20 (m, 1H), 4.50–4.31 (m, 2H), 4.10–3.95 (m, 1H), 3.60–3.45 (m, 2H), 3.40–3.36 (m, 1H), 3.00–2.60 (m, 8H), 1.50–1.30 (m, 1H), 1.23–0.55 (m, 17H).

Example 40

3(R)-[1(S)-[4-(2-Dimethylaminoethoxy)benzoyl]-2-phenyl]ethylcarbamoyl-5-methyl-2(R or S)-(2-propenyl)hexanohydroxamic Acid Hydrochloride $^1$H-NMR (500 MHz, DMSO-d$_6$) δ 10.36 (br s, 1H), 9.90–9.70 (br, 1H), 8.75–8.65 (br, 1H), 8.52 (d, J=8.4 Hz, 1H), 8.04 (d, J=8.9 Hz, 2H), 7.35 (d, J=7.3 Hz, 2H), 7.24 (t, J=7.6 Hz, 2H), 7.15 (t, J=7.6 Hz, 1H), 7.11 (d, J=8.9 Hz, 2H), 5.62–5.55 (m, 1H), 5.42–5.30 (m, 1H), 4.81 (d, J=10.3 Hz, 1H), 4.71 (dd, J=17.1, 1.8 Hz, 1H), 4.48–4.35 (m, 2H), 3.60–3.50 (m, 2H), 3.08 (dd, J=14.0, 4.2 Hz, 1H), 2.90–2.80 (m, 1H), 2.86 (s, 6H), 2.36 (ddd, J=10.4, 10.4, 3.1 Hz, 1H), 1.92 (ddd, J=10.8, 10.7, 2.8 Hz, 1H), 1.88–1.75 (m, 1H), 1.32–1.20 (m, 2H), 1.08–0.95 (m, 1H), 0.85–0.75 (m, 1H), 0.67 (d, J=6.5 Hz, 3H), 0.60 (d, J=6.5 Hz, 3H).

Example 83

Sodium Salt of 2-Tetrahydropyranyl 3(R)-[1(S)-(2-Furyl)carbonyl-2-[4-(hydroxysulfonyloxy)phenyl]]ethylcarbamoyl-5-methyl-2(R or S)-(2,5-dioxo-3,4,4-trimethyl-1-imidazolidinyl)methylhexanohydroxamic Acid $^1$H-NMR (300 MHz, DMSO-d$_6$) δ 10.96 (br s, 1H), 8.70–8.55 (m, 1H), 8.07–7.98 (m, 1H), 7.65–7.55 (m, 1H), 7.20 (d, J=8.3 Hz, 2H), 6.98–6.88 (m, 2H), 6.75–6.70 (m, 1H), 5.35–5.10 (m, 1H), 4.80–4.50 (m, 1H), 4.00–3.25 (m, 3H), 3.02 (dd, J=14.3, 4.8 Hz, 1H), 2.92–2.68 (m, 4H), 2.62–2.30 (m, 2H), 1.70–1.05 (m, 8H), 1.26 (s, 3H), 1.25 (s, 3H), 0.90–0.70 (m, 1H), 0.75 (d, J=6.3 Hz, 3H), 0.67 (d, J=6.3 Hz, 3H).

Example 84

Sodium Salt of 3(R)-[1(S)-(2-Furyl)carbonyl-2-[4-(hydroxysulfonyloxy)phenyl]]ethylcarbamoyl-5-methyl-2(R or S)-(2,5-dioxo-3,4,4-trimethyl-1-imidazolidinyl)methylhexanohydroxamic Acid $^1$H-NMR (300 MHz, DMSO-d$_6$) δ 10.37 (br s, 1H), 8.67 (br s, 1H), 8.63 (d, J=8.1 Hz, 1H), 8.02 (d, J=1.7 Hz, 1H), 7.60 (d, J=3.6 Hz, 1H), 7.20 (d, J=8.5 Hz, 2H), 6.93 (d, J=8.5 Hz, 2H), 6.72 (dd, J=3.6, 1.7 Hz, 1H), 5.35–5.20 (m, 1H), 3.50–3.20 (m, 1H), 3.01 (dd, J=13.8, 4.9 Hz, 1H), 2.82 (dd, J=13.8, 10.2 Hz, 1H), 2.74 (s, 3H), 2.65–2.40 (m, 2H), 2.35–2.20 (m, 1H), 1.50–1.30 (m, 1H), 1.30–1.05 (m, 1H), 1.25 (s, 3H), 1.24 (s, 3H), 0.90–0.70 (m, 1H), 0.75 (d, J=6.5 Hz, 3H), 0.67 (d, J=6.5 Hz, 3H).

Example 147

3(R)-[2,2-Dimethyl-1(S)-[4-(2-dimethylaminoethoxy)benzoyl]]propylcarbamoyl-5-methyl-2(R or S)-(2,5-dioxo-3,4,4-trimethyl-1-imidazolidinyl)methylhexanohydroxamic Acid Hydrochloride $^1$H-NMR (300 MHz, DMSO-d$_6$) δ 10.72 (br s, 1H), 10.47 (s, 1H), 8.72 (br s, 1H), 8.30 (d, J=7.6 Hz, 1H), 8.01 (d, J=8.6 Hz, 2H), 7.11 (d, J=8.7 Hz, 2H), 5.29 (d, J=7.6 Hz, 1H), 4.47 (br s, 2H), 3.86 (dd, J=12.3, 12.1 Hz, 1H), 3.53 (br s, 2H), 3.10 (dd, J=12.8, 4.2 Hz, 1H), 2.93–2.79 (m, 1H), 2.84 (s, 6H), 2.76 (s, 3H), 2.65 (ddd, J=10.7, 10.7, 4.2 Hz, 1H), 1.44–1.31 (m, 1H), 1.25 (s, 6H), 1.18–1.05 (m, 1H), 0.93 (s, 9H), 0.89–0.79 (m, 1H), 0.76 (d, J=6.3 Hz, 3H), 0.64 (d, J=6.5 Hz, 3H).

Example 245

3(R)-[1(S)-[2-(5-Hydroxymethyl)furyl]carbonyl-2-phenyl]ethylcarbamoyl-5-methyl-2(R or S)-(2,5-dioxo-3,4,4-trimethyl-1-imidazolidinyl)methylhexanohydroxamic Acid $^1$H-NMR (300 MHz, DMSO-$d_6$) δ 10.35 (br s, 1H), 8.75–8.60 (br, 1H), 8.60 (d, J=8.4 Hz, 1H), 7.59 (d, J=3.6 Hz, 1H), 7.36 (d, J=7.3 Hz, 2H), 7.13 (t, J=7.6 Hz, 2H), 6.99 (t, J=7.4 Hz, 1H), 6.54 (d, J=3.6 Hz, 1H), 5.70–5.40 (br, 1H), 5.40–5.28 (m, 1H), 4.49 (s, 2H), 3.40–3.20 (m, 1H), 3.07 (dd, J=13.7, 4.5 Hz, 1H), 2.83 (dd, J=13.7, 10.8 Hz, 1H), 2.75 (s, 3H), 2.60–2.35 (m, 2H), 2.03 (dd, J=13.3, 3.8 Hz, 1H), 1.45–1.30 (m, 1H), 1.30–1.10 (m, 1H), 1.24 (s, 3H), 1.22 (s, 3H), 0.85–0.70 (m, 1H), 0.76 (d, J=6.5 Hz, 3H), 0.68 (d, J=6.5 Hz, 3H).

Experimental Example 1

Inhibitory Activity of TNF α Release

The inhibitory effect of each compound (compounds of Examples 1, 2, 3, 6, 35, 39 and 44) on the release of TNF α from THP-1 cells which are monocyte cultured cells [see Nature 370, 218–220 (1994)] was investigated.

The THP-1 cells were suspended to a concentration of 1×10$^6$ cells/ml in RPMI1640 medium supplemented with 10% fetal calf serum (FCS) and dispensed by 100 μl. A 2 μg/ml LPS was prepared with RPMI1640 medium supplemented with 10% FCS. Each compound (dissolved in dimethyl sulfoxide) was diluted 500-fold with the LPS solution.

The diluted solutions of these compounds were added to the dispensed cell suspensions by 100 μl and allowed for 3 hr to react under the conditions of 37° C., 5% $CO_2$. After the completion of the reaction, the reaction mixture was centrifuged and the culture supernatant was collected. The TNF α amount was quantitatively measured by ELISA (enzyme-linked immunosorbent assay). The TNF α release inhibitory effect by each compound was calculated from the proportion of released TNF α amount of the compound addition group relative to that of the compound non-addition group.

TABLE 11

| Test substance (Example No.) | Inhibitory activity of TNF α release, $IC_{50}$ (μM) |
| --- | --- |
| 1 | 0.27 |
| 2 | 0.20 |
| 3 | 0.19 |
| 6 | 0.66 |
| 35 | 0.14 |
| 39 | 0.30 |
| 44 | 0.42 |

Experimental Example 2

Inhibitory Activity of TNF α Release

The inhibitory effect of each compound (compounds of Examples 2, 6, 7, 10, 11, 37, 147, 231 and 245) on the release of TNF α from LPS treated human whole blood [see: Lymphokine Res 8, 141–146 (1989)] was investigated.

Human whole blood was diluted 4-fold with RPMI1640 medium supplemented with 10% FCS. The diluted blood was dispensed to a 96 multi-well plate by 100 μl and equilibrated under the conditions of 37° C., 5% $CO_2$. LPS (2 μg/ml) was prepared with RPMI1640 medium supplemented with 10% FCS and a culture broth prepared by dissolving each compound (dissolved in dimethyl sulfoxide) in the LPS solution was added by 100 μl/well (final concentrated of dimethyl sulfoxide 0.1%), which was followed by incubation for 24 hr (37° C., 5% $CO_2$). After the incubation, the reaction mixture was centrifuged (1,500 rpm, 5 min). The culture supernatant (40 μl/well) was collected, and TNF α amount in the supernatant was quantitatively measured by ELISA. The TNF α release inhibitory effect by each compound was calculated from the proportion of release TNF α amount of the compound addition group relitive to that of the compound non-addition group.

TABLE 12

| Test substance (Example No.) | Inhibitory activity of TNF α release, $IC_{50}$ (μM) |
| --- | --- |
| 2 | 0.65 |
| 6 | 1.39 |
| 7 | 2.46 |
| 10 | 1.70 |
| 11 | 1.73 |
| 37 | 3.47 |
| 147 | 2.29 |
| 231 | 5.45 |
| 245 | 3.74 |

It is evident from the above experimental results that the hydroxamic acid derivative of the present invention inhibits the production of TNF α.

Experimental Example 3

Solubility

The solubility of the Example compounds of the present invention in saline (0.9% aqueous sodium chloride solution) at 25° C. was measured. The results are shown in Table 13.

TABLE 13

| Example No. | Solubility, saline, mg/ml |
| --- | --- |
| 1 | >10 |
| 2 | >5 |
| 5 | >20 |
| 6 | >20 |
| 7 | >20 |
| 8 | >20 |
| 9 | >20 |
| 10 | 10 |
| 11 | >20 |
| 19 | >20 |
| 35 | >20 |
| 37 | >20 |
| 39 | >20 |
| 84 | >20 |
| 88 | 5 |
| 147 | >20 |

Formulation Example 1

Tablets having the following composition were produced by a conventioal method.

| Ingrdients | per tablet |
|---|---|
| compound of Example 2 | 10 mg |
| lactose | 125 mg |
| corn starch | 75 mg |
| talc | 4 mg |
| magnesium stearate | 1 mg |
| total weight | 215 mg |

Formulation Example 2

Capsules having the following composition were produced by a conventional method.

| Ingrdients | per capsule |
|---|---|
| compound of Example 2 | 10 mg |
| lactose | 165 mg |
| corn starch | 20 mg |
| talc | 5 mg |
| weight per capsule | 200 mg |

Formulation Example 3

Ointment having the following composition was produced by a conventional method.

| Ingrdients | dose |
|---|---|
| compound of Example 2 | 0.2 g |
| white petrolatum | 97.8 g |
| liquid paraffin | 2 g |
| total weight | 100 g |

Formulation Example 4

Injections having the following composition were produced by a conventional method.

| Ingrdients | dose |
|---|---|
| compound of Example 6 | 0.2 g |
| sodium chloride | 0.9 g |
| distilled water for injection | appropriate amount |
| total weight | 100 g |

Formulation Example 5

Eye drops having the following composition were produced by a conventional method.

| Ingrdients | |
|---|---|
| compound of Example 6 | 0.1 g |
| sodium chloride | 0.3 g |
| sterile purified water | appropriate amount |
| total weight | 100 g |

Industrial Applicability

The hydroxamic acid derivative and a pharmacologically acceptable salt thereof of the present invention have an inhibitory activity of TNF α production and are useful for the prophylaxis and treatment of the diseases such as autoimmune diseases and inflammatory diseases (e.g., sepsis, MOF, rheumatoid arthritis, Crohn's disease, cachexia, myasthenia gravis, systemic lupus erythematosus, asthma, I type diabetes, psoriasis and the like), and the like.

This application is based on application No. 141304/1998 filed in Japan, the contents of which are incorporated hereinto by reference.

What is claimed is:

1. A hydroxamic acid compound of the formula (I):

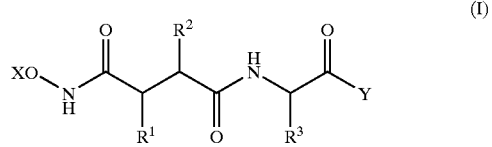

wherein
X is hydrogen or hydroxy-protecting group;
$R^1$ is hydrogen, alkyl, arylalkyl, heteroarylthioalkyl, arylthioalkyl, alkylthioalkyl, arylalkylthioalkyl, phthalimidoalkyl, alkenyl, or —(CH$_2$)$_l$—A
wherein l is an integer of 1 to 4 and A is a 5- or 6-membered N-heterocycle
(a) which is bonded by N atom,
(b) which optionally has at least one atom selected from N, O and S as an additional heteroatom at a position not adjacent to the bonded N atom,
(c) in which one or both C atom(s) adjacent to said bonded N atom is(are) substituted by oxo, and
(d) which is benzo-fused, or one or more other C atom(s) is(are) substituted by lower alkyl or oxo, and/or a different N atom is optionally substituted by lower alkyl or phenyl;
$R^2$ is hydrogen, alkyl, arylalkyl, heteroarylalkyl, cycloalkyl, cycloalkylalkyl or aryl;
$R^3$ is hydrogen, alkyl or a group of the formula

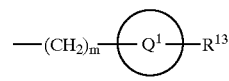

wherein $Q^1$ is an aromatic hydrocarbon ring or an aromatic heterocycle, m is an integer of 0 to 3, and $R^{13}$ is hydrogen, halogen, hydroxy, nitro, cyano, trifluoromethyl, lower alkyl, alkoxy, alkylthio, formyl, acyloxy, phenyl, arylalkyl, carboxy, —COORa wherein Ra is lower alkyl, arylalkyl or aryl, carbamoyl, guanidino, hydroxysulfonyloxy, sulfo, arylalkyloxyalkyl or a group selected from

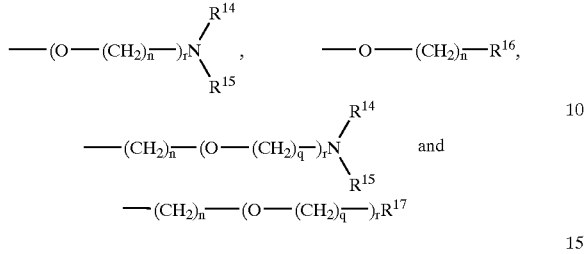

wherein n and q are the same or different and each is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, $R^{16}$ is aryl, heteroaryl, hydroxysulfonyloxy or sulfo and $R^{17}$ is hydroxy, hydroxysulfonyloxy, sulfo or carboxy; and Y is a group of the formula

wherein $Q^2$ is an aromatic heterocycle, and $R^{18}$ is hydrogen, halogen, hydroxy, nitro, cyano, trifluoromethyl, lower alkyl, alkoxy, alkylthio, formyl, acyloxy, phenyl, arylalkyl, carboxy, —COORa wherein Ra is lower alkyl, arylalkyl or aryl, carbamoyl, guanidino, hydroxysulfonyloxy, sulfo, arylalkyloxyalkyl or a group selected from

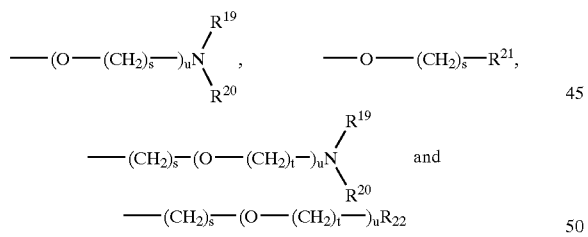

wherein s and t are the same or different and each is an integer of 1 to 5, u is an integer of 0 to 2, $R^{19}$ and $R^{20}$ are the same or different and each is hydrogen, alkyl, arylalkyl, heteroarylalkyl or aryl, or $R^{19}$ and $R^{20}$ may form, together with the adjacent nitrogen atom, an optionally substituted heterocycle, $R^{21}$ is aryl, heteroaryl, hydroxysulfonyloxy, sulfo or carboxy, and $R^{22}$ is hydroxy, hydroxysulfonyloxy, sulfo or carboxy;

provided that when (i) $R^3$ is a group other than a group of the formula (A)

(A)

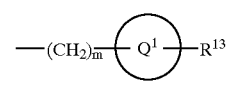

wherein $Q^1$ is a benzene ring, m is an integer of 0 to 3, and $R^{13}$ is guanidino, hydroxysulfonyloxy, sulfo or a group selected from

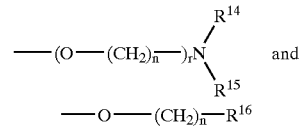

wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, then (ii) Y should be a group of the formula (B)

(B)

wherein $Q^2$ is a furan ring, and $R^{18}$ is arylalkyloxyalkyl or a group selected from

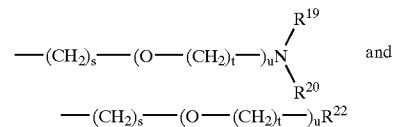

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy, wherein the aforementioned arylalkyl, heteroarylthioalkyl, arylthioalkyl, arylalkylthioalkyl, phthalimidoalkyl, aryl, heteroaryl and heteroarylalkyl may have a substituent, or a pharmacologically acceptable salt thereof.

2. The hydroxamic acid compound of claim 1, wherein (i) $R^3$ is a group of the formula (A)

(A)

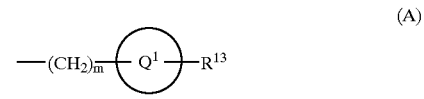

wherein $Q^1$ is a benzene ring, m is an integer of 0 to 3, and $R^{13}$ is guanidino, hydroxysulfonyloxy, sulfo or a group selected from

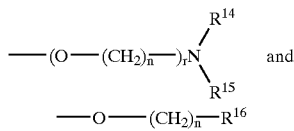

wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, and Y is furyl, thienyl, pyrrolyl, pyridyl, or thiazolyl, or (ii) $R^3$ is alkyl or a group of the formula

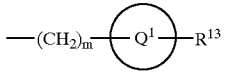

wherein $Q^1$ is a benzene ring, m is an integer of 0 to 3, and $R^{13}$ is hydrogen, and Y is a group of the formula (B)

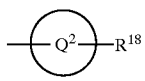

(B)

wherein $Q^2$ is a furan ring, and $R^{18}$ is arylalkyloxyalkyl or a group selected from

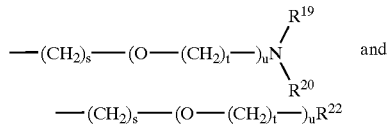

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy, or a pharmacologically acceptable salt thereof.

3. The hydroxamic acid compound of claim 2, wherein $R^{13}$ in the formula (A) is guanidino, hydroxysulfonyloxy or a group of the formula

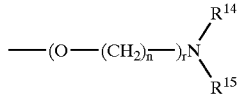

wherein each symbol is as defined in claim 2, or a pharmacologically acceptable salt thereof.

4. The hydroxamic acid compound of claim 2 or a pharmacologically acceptable salt thereof, which is a member selected from the group consisting of 3(R)-[1(S)-(2-furyl)carbonyl-2-(4-guanidinophenyl)] ethylcarbamoyl-5-methyl-2(R or S)-phthalimidomethylhexanohydroxamic acid hydrochloride, 3(R)-[1(S)-[2-[5-(2-dimethylaminoethoxy)methyl]furyl]carbonyl-2-phenyl]ethylcarbamoyl-5-methyl-2(R or S)-phthalimidomethylhexanohydroxamic acid hydrochloride, 3(R)-[2-[4-(2-dimethylaminoethoxy)phenyl]-1(S)-(2-furyl)carbonyl]ethylcarbamoyl-5-methyl-2-(R or S)-(2,5-dioxo-3,4,4-trimethyl-1-imidazolidinyl)methylhexanohydroxamic acid hydrochloride, sodium salt of 3(R)-[1(S)-(2-furyl)carbonyl-2-[4-(hydroxysulfonyloxy)phenyl]]ethylcarbamoyl-5-methyl-2(R or S)-phthalimidomethylhexanohydroxamic acid, sodium salt of 3(R)-[1(S)-(2-furyl)carbonyl-2-(4-sulfophenyl)ethylcarbamoyl]-5-methyl-2(R or S)-(2-naphthylmethyl)hexanohydroxamic acid, sodium salt of 3(R)-[1(S)-(2-furyl)carbonyl-2-(4-sulfophenyl)ethylcarbamoyl]-5-methyl-2(R or S)-(1-naphthylmethyl)hexanohydroxamic acid, sodium salt of 2(R or S)-benzyl-3(R)-[1(S)-(2-furyl)carbonyl-2-(4-sulfophenyl)ethylcarbamoyl]-5-methylhexanohydroxamic acid, sodium salt of 3(R)-[1(S)-(2-furyl)carbonyl-2-(4-sulfophenyl)ethylcarbamoyl]-5-methyl-2(R or S)-phthalimidomethylhexanohydroxamic acid, sodium salt of 3(R)-[1(S)-(2-furyl)carbonyl-2-(4-sulfophenyl)ethylcarbamoyl]-5-methyl-2(R or S)-(1-oxoisoindolin-2-ylmethyl)hexanohydroxamic acid, 3(R)-[2-(4-aminophenyl)-1(S)-(2-furyl)carbonyl] ethylcarbamoyl-5-methyl-2(R or S)-phthalimidomethylhexanohydroxamic acid hydrochloride, 3(R)-[1(S)-[2-(5-dimethylaminomethyl)furyl]carbonyl-2-phenyl]ethylcarbamoyl-5-methyl-2(R or S)-phthalimidomethylhexanohydroxamic acid hydrochloride, 3(R)-[2-[4-(2-dimethylaminoethoxy)phenyl]-1(S)-(2-furyl)carbonyl]ethylcarbamoyl-5-methyl-2(R or S)-phthalimidomethylhexanohydroxamic acid hydrochloride, 3(R)-[1(S)-[2-(5-hydroxymethyl)furyl]carbonyl-2-phenyl]ethylcarbamoyl-5-methyl-2(R or S)-phthalimidomethylhexanohydroxamic acid, 3(R)-[2-[4-(2-dimethylaminoethoxy)phenyl]-1(S)-(2-furyl)carbonyl]ethylcarbamoyl-5-methyl-2(R or S)-(3-phenylpropyl)hexanohydroxamic acid hydrochloride, sodium salt of 3(R)-[1(S)-(2-furyl)carbonyl-2-[4-(hydroxysulfonyloxy)phenyl]]ethylcarbamoyl-5-methyl-2(R or S)-(2,5-dioxo-3,4,4-trimethyl-1-imidazolidinyl)methylhexanohydroxamic acid, sodium salt of 3(R)-[1(S)-(2-furyl)carbonyl-2-[4-(hydroxysulfonyloxy)phenyl]]ethylcarbamoyl-5-methyl-2(R or S)-(3-phenylpropyl)hexanohydroxamic acid, 3(R)-[2-[4-(2-dimethylaminoethoxy)phenyl]-1(S)-(2-furyl)carbonyl]ethylcarbamoyl-5-methyl-2(R or S)-(2-naphthylmethyl)hexanohydroxamic acid hydrochloride, 3(R)-[2-[4-(2-dimethylaminoethoxy)phenyl]-1(S)-(2-furyl)carbonyl]ethylcarbamoyl-5-methyl-2(R or S)-(1-oxoisoindolin-2-ylmethyl)hexanohydroxamic acid hydrochloride, sodium salt of 3(R)-[1(S)-(2-furyl)carbonyl-2-[4-(hydroxysulfonyloxy)phenyl]]ethylcarbamoyl-5-methyl-2(R or S)-(2-naphthylmethyl)hexanohydroxamic acid, sodium salt of 3(R)-[1(S)-(2-furyl)carbonyl-2-[4-(hydroxysulfonyloxy)phenyl]]ethylcarbamoyl-5-methyl-2(R or S)-(1-oxoisoindolin-2-ylmethyl) hexanohydroxamic acid, sodium salt of 3(R)-[1(S)-(2-furyl)carbonyl-2-(4-sulfophenyl)ethylcarbamoyl]-5-methyl-2(R or S)-(3-phenylpropyl)hexanohydroxamic acid, sodium salt of 3(R)-[1(S)-(2-furyl)carbonyl-2-(4-sulfophenyl)ethylcarbamoyl]-5-methyl-2(R or S)-(2,5-dioxo-3,4,4-trimethyl-1-imidazolidinyl) methylhexanohydroxamic acid, and 3(R)-[1(S)-[2-(5-hydroxymethyl)furyl]carbonyl-2-phenyl]ethylcarbamoyl-5-methyl-2(R or S)-(2,5-dioxo-3,4,4-trimethyl-1-imidazolidinyl) methylhexanohydroxamic acid.

5. The hydroxamic acid compound of claim 1 or claim 2, wherein $R^1$ is phthalimidomethyl, or a pharmacologically acceptable salt thereof.

6. The hydroxamic acid compound of claim 1 or claim 2, wherein $R^2$ is isobutyl, or a pharmacologically acceptable salt thereof.

7. The hydroxamic acid compound of claim 1 or claim 2, wherein $R^3$ is benzyl optionally substituted by a substituent selected from guanidino, hydroxysulfonyloxy, sulfo,

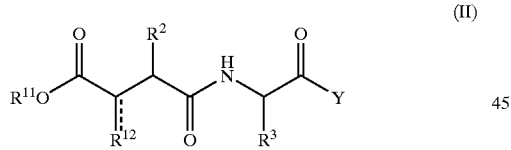

wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, or a pharmacologically acceptable salt thereof.

8. A compound of the formula (II):

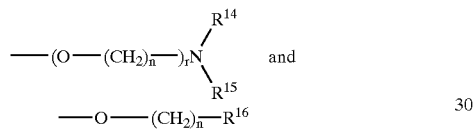

wherein $R^{11}$ is hydrogen, alkyl, arylalkyl, heteroarylalkyl or aryl, $\overline{\phantom{-----}}$ is a single bond or a double bond, when $\overline{\phantom{-----}}$ is a single bond, $R^{12}$ is hydrogen, alkyl, arylalkyl, heteroarylthioalkyl, arylthioalkyl, alkylthioalkyl, arylalkylthioalkyl, phthalimidoalkyl, alkenyl, —(CH₂)$_l$—A wherein l is an integer of 1 to 4, A is a 5- or 6-membered N-heterocycle (a) which is bonded by N atom, (b) which optionally has at least one atom selected from N, O and S as an additional heteroatom at a position not adjacent to the bonded N atom, (c) in which one or both C atom(s) adjacent to said bonded N atom is(are) substituted by oxo, and (d) which is benzo-fused, or one or more other C atom(s) is(are) substituted by lower alkyl or oxo, and/or a different N atom is optionally substituted by lower alkyl or phenyl, or —COOR$^{23}$ wherein $R^{23}$ is hydrogen, alkyl, arylalkyl, heteroarylalkyl or aryl, or when $\overline{\phantom{-----}}$ is a double bond, $R^{12}$ is $CH_2$;

$R^2$ is hydrogen, alkyl, arylalkyl, heteroarylalkyl, cycloalkyl, cycloalkylalkyl or aryl;

$R^3$ is hydrogen, alkyl or a group of the formula

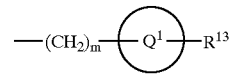

wherein $Q^1$ is an aromatic hydrocarbon ring or an aromatic heterocycle, m is an integer of 0 to 3, and $R^{13}$ is hydrogen, halogen, hydroxy, nitro, cyano, trifluoromethyl, lower alkyl, alkoxy, alkylthio, formyl, acyloxy, phenyl, arylalkyl, carboxy, —COORa wherein Ra is lower alkyl, arylalkyl or aryl, carbamoyl, guanidino, hydroxysulfonyloxy, sulfo, arylalkyloxyalkyl or a group selected from

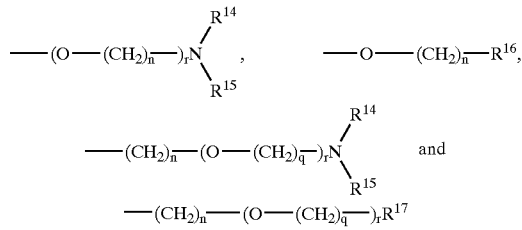

wherein n and q are the same or different and each is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, $R^{16}$ is aryl, heteroaryl, hydroxysulfonyloxy or sulfo, and $R^{17}$ is hydroxy, hydroxysulfonyloxy, sulfo or carboxy;

Y is a group of the formula

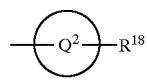

wherein $Q^2$ is an aromatic heterocycle, and $R^{18}$ is hydrogen, halogen, hydroxy, nitro, cyano, trifluoromethyl, lower alkyl, alkoxy, alkylthio, formyl, acyloxy, phenyl, arylalkyl, carboxy, —COORa wherein Ra is lower alkyl, arylalkyl or aryl, carbamoyl, guanidino, hydroxysulfonyloxy, sulfo, arylalkyloxyalkyl or a group selected from

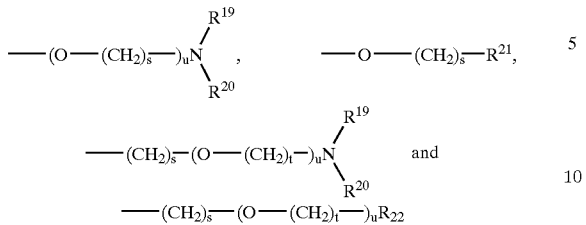

wherein s and t are the same or different and each is an integer of 1 to 5, u is an integer of 0 to 2, $R^{19}$ and $R^{20}$ are the same or different and each is hydrogen, alkyl, arylalkyl, heteroarylalkyl or aryl, or $R^{19}$ and $R^{20}$ may form, together with the adjacent nitrogen atom, an optionally substituted heterocycle, $R^{21}$ is aryl, heteroaryl, hydroxysulfonyloxy, sulfo or carboxy, and $R^{22}$ is hydroxy, hydroxysulfonyloxy, sulfo or carboxy; provided that when (i) $R^3$ is a group other than a group of the formula (A)

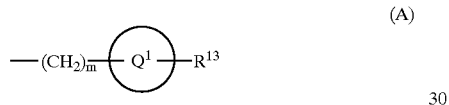

wherein $Q^1$ is a benzene ring, m is an integer of 0 to 3, and $R^{13}$ is guanidino, hydroxysulfonyloxy, sulfo or a group selected from

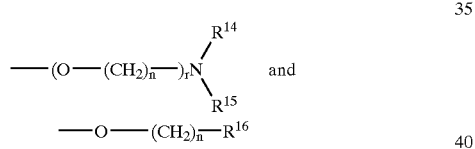

wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, then (ii) Y should be a group of the formula (B)

wherein $Q^2$ is a furan ring, and $R^{18}$ is arylalkyloxyalkyl or a group selected from

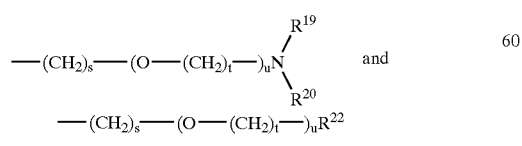

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy, wherein the aforementioned arylalkyl, heteroarylthioalkyl, arylthioalkyl, arylalkylthioalkyl, phthalimidoalkyl, aryl, heteroaryl and heteroarylalkyl may have a substituent.

9. The compound of claim 8 wherein (i) $R^3$ is a group of the formula (A)

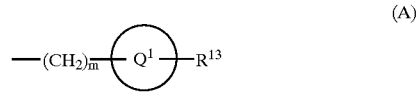

wherein $Q^1$ is a benzene ring, m is an integer of 0 to 3, and $R^{13}$ is guanidino, hydroxysulfonyloxy, sulfo or a group selected from

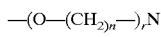

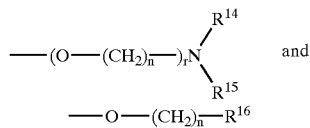

wherein n is an integer of 1 to 5, r is an integer of 0 to 2, $R^{14}$ and $R^{15}$ are the same or different and each is hydrogen, alkyl, arylalkyl, heteroarylalkyl or aryl, or $R^{14}$ and $R^{15}$ may form, together with the adjacent nitrogen atom, an optionally substituted heterocycle, and $R^{16}$ is hydroxysulfonyloxy or sulfo, and Y is furyl, thienyl, pyrrolyl, pyridyl, or thiazolyl, or (ii) $R^3$ is alkyl or a group of

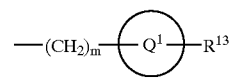

wherein $Q^1$ is a benzene ring, m is an integer of 0 to 3, and $R^{13}$ is hydrogen, and Y is a group of the formula (B)

wherein $Q^2$ is a furan ring, and $R^{18}$ is arylalkyloxyalkyl or a group selected from

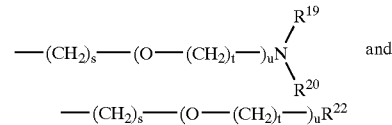

wherein s and t are the same or different and each is an integer of 1 to 5, u is an integer of 0 to 2, $R^{19}$ and $R^{20}$ are the same or different and each is hydrogen, alkyl, arylalkyl, heteroaryl or aryl, or $R^{19}$ and $R^{20}$ may form, together with the adjacent nitrogen atom, an optionally substituted heterocycle, and $R^{22}$ is hydroxy, hydroxysulfonyloxy, sulfo or carboxy.

10. A pharmaceutical composition comprising a hydroxamic acid compound of any of claims 1 to 4 or a pharmacologically acceptable salt thereof, and a pharmacologically acceptable carrier.

11. A pharmaceutical composition comprising a hydroxamic acid compound of claim 5 or a pharmacologically acceptable salt thereof, and a pharmacologically acceptable carrier.

12. A pharmaceutical composition comprising a hydroxamic acid compound of claim 6 or a pharmacologically acceptable salt thereof, and a pharmacologically acceptable carrier.

13. A pharmaceutical composition comprising a hydroxamic acid compound of claim 7 or a pharmacologically acceptable salt thereof, and a pharmacologically acceptable carrier.

* * * * *